US009175348B2

(12) United States Patent
Korlach et al.

(10) Patent No.: US 9,175,348 B2
(45) Date of Patent: Nov. 3, 2015

(54) IDENTIFICATION OF 5-METHYL-C IN NUCLEIC ACID TEMPLATES

(71) Applicants: Pacific Biosciences of California, Inc., Menlo Park, CA (US); University of Chicago, Chicago, IL (US)

(72) Inventors: Jonas Korlach, Newark, CA (US); Chuan He, Chicago, IL (US); Tyson A. Clark, Menlo Park, CA (US); Liang Zhang, Chicago, IL (US); Xingyu Lu, Chicago, IL (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 99 days.

(21) Appl. No.: 13/868,661

(22) Filed: Apr. 23, 2013

(65) Prior Publication Data

US 2014/0004511 A1    Jan. 2, 2014

Related U.S. Application Data

(60) Provisional application No. 61/637,687, filed on Apr. 24, 2012.

(51) Int. Cl.
| C12P 19/34 | (2006.01) |
| C12Q 1/68 | (2006.01) |
| C07H 21/02 | (2006.01) |
| C07H 21/04 | (2006.01) |
| C07H 21/00 | (2006.01) |

(52) U.S. Cl.
CPC ............ *C12Q 1/6883* (2013.01); *C12Q 1/6827* (2013.01); *C12Q 1/6869* (2013.01)

(58) Field of Classification Search
USPC ........... 435/6.1, 6.11, 6.12, 91.1, 91.2, 91.51; 436/94, 501; 536/23.1, 24.3, 24.33, 536/25.3
See application file for complete search history.

(56) References Cited

U.S. PATENT DOCUMENTS

| 5,547,839 | A  | 8/1996  | Dower et al. |
| 6,210,896 | B1 | 4/2001  | Chan |
| 6,235,502 | B1 | 5/2001  | Weissman et al. |
| 6,255,083 | B1 | 7/2001  | Williams |
| 6,555,311 | B1 | 4/2003  | Locarnini et al. |
| 6,787,308 | B2 | 9/2004  | Balasubramanian et al. |
| 7,056,661 | B2 | 6/2006  | Korlach et al. |
| 7,399,614 | B2 | 7/2008  | Zon |
| 7,459,274 | B2 | 12/2008 | Lakey et al. |
| 7,611,869 | B2 | 11/2009 | Fan |
| 8,137,937 | B2 | 3/2012  | Markert-Hahn |
| 8,153,375 | B2 | 4/2012  | Travers et al. |
| 8,486,634 | B2 | 7/2013  | Lim et al. |
| 2002/0102577 | A1 | 8/2002 | Raillard et al. |
| 2003/0096253 | A1 | 5/2003 | Nelson et al. |
| 2003/0190647 | A1 | 10/2003 | Odera |
| 2003/0215862 | A1 | 11/2003 | Parce et al. |
| 2004/0048300 | A1 | 3/2004 | Sood et al. |
| 2004/0152119 | A1 | 8/2004 | Sood et al. |
| 2004/0224319 | A1 | 11/2004 | Sood et al. |
| 2005/0053937 | A1 | 3/2005 | Berlin |
| 2005/0208538 | A1 | 9/2005 | Kurn et al. |
| 2005/0214812 | A1 | 9/2005 | Li et al. |
| 2005/0239085 | A1 | 10/2005 | Busby et al. |
| 2006/0024676 | A1 | 2/2006 | Uhlmann et al. |
| 2006/0063264 | A1 | 3/2006 | Turner et al. |
| 2007/0020640 | A1 | 1/2007 | McCloskey et al. |
| 2008/0207460 | A1 | 8/2008 | Gormley |
| 2009/0012282 | A1 | 1/2009 | Zon |
| 2009/0024331 | A1 | 1/2009 | Tomaney et al. |
| 2009/0269771 | A1 | 10/2009 | Schroeder |
| 2009/0280538 | A1 | 11/2009 | Patel et al. |
| 2009/0298075 | A1 | 12/2009 | Travers et al. |
| 2010/0041057 | A1 | 2/2010 | Dong et al. |
| 2010/0121582 | A1 | 5/2010 | Pan et al. |
| 2010/0190175 | A1 | 7/2010 | Gerard et al. |
| 2010/0221716 | A1 | 9/2010 | Flusberg et al. |
| 2010/0255487 | A1 | 10/2010 | Beechem et al. |
| 2011/0104787 | A1 | 5/2011 | Church et al. |
| 2011/0183320 | A1 | 7/2011 | Flusberg et al. |
| 2011/0201524 | A1 | 8/2011 | Kester |
| 2011/0236894 | A1 | 9/2011 | Rao et al. |
| 2011/0237444 | A1 | 9/2011 | Clancy et al. |
| 2012/0329042 | A1 | 12/2012 | Beechem et al. |
| 2014/0322707 | A1* | 10/2014 | He et al. ...................... 435/6.11 |

FOREIGN PATENT DOCUMENTS

| WO | 9106678 A1 | 5/1991 |
| WO | 9627025 A1 | 9/1996 |
| WO | 9703210 A1 | 1/1997 |
| WO | 9905315 A2 | 2/1999 |
| WO | 2006005064 | 1/2006 |

(Continued)

OTHER PUBLICATIONS

International Search Report and Written Opinion dated Sep. 24, 2013 for related PCT/US2013/037829.
Ahle, J.D. et al. "Sequence determination of nucleic acids containing 5-methyllsocytosine and isoguanine: identification and insight into polymerase replication of the non-natural nucleabases" Nucl Acids Res (2005) 33 (10):3176-3184.
Ananiev, G.E. et al. "Optical mapping discerns geneome wide DNA methylation profiles" BMC Mol Biol (2008) 9:68.
Avvakumov, G.V. et al. "Structural bases for recocgnition of hemi-methylated DNA by the SRA domain of human UHRF1" Nature (2008) 455(7214):822-825.
Banerjee, A. et al, "StructuRe of a repair enzye interrogating undamaged DNA elucidates recognition of damaged DNA" Nature (2005) 434(7033:612-618.

(Continued)

Primary Examiner — Frank Lu
(74) Attorney, Agent, or Firm — Deana A. Arnold

(57) ABSTRACT

A method for identifying a 5-MeC in a template nucleic is provided. The method comprises providing a template having 5-MeC, converting the 5-MeC into a further modification selected from 5-caC and 5-FC. The converted template is then sequenced, and a change in sequencing is detected that is indicative of the further modification, allowing for identifying the 5-MeC in the template nucleic acid.

13 Claims, 33 Drawing Sheets

(56) References Cited

FOREIGN PATENT DOCUMENTS

| WO | 2007068437 A1 | 6/2007 |
|---|---|---|
| WO | 2010068289 A2 | 6/2010 |
| WO | 2010003153 A2 | 7/2010 |

OTHER PUBLICATIONS

Bareyt, S. et al. "Selective Detection of 5-Methylcytosine Sites in DNA" Angew Chem Int Ed Engl (2008) 47 (1)181-184.
Berman, A.J. et al. "Structures of phi29 DNA polymerase complexed with substrate: the mechanism of translocation in B-famiiy polymerases" EMBO J (2007) 26:3494-3505.
Blainey, P.C. et al. "A base-excision DNA-repair protein finds intrahelical leesion bases by fast sliding in contact with DNA" PNAS (2006) 103(15):5752-5757.
Braun, J.V. et al. "Statistical Methods for DNA Sequence Segmentation" Statist Sci (1998) 13(2):142-162.
Brewer, A.C. et al. "A simplified method for in vivo footprinting using DMS" Nucl Acids Res (1990) 18:5574.
Brunner, A.L. et al. "Distinct DNA methylation patterns characterize differentiated human embryonic stem cells and developing human fetal liver" Genome Res (2009) 19:1044-1056.
Colasanti, et al., "Cytosine Methylated DNA Synthesized by Taq Polymerase Used to Assay Methylation Sensitivity of Restriction Endonuclease Hinfl" Nucleic Acids Research (1991) 19(2):391-394.
Cordonnier, A.M. et al. "Impaired transiesion synthesis in Xeroderma Piggmentosum variant extracts" Mol Cell Biol (1999) 19(3):2206-2211.
Eid, J. et al. "Real-time DNA Sequencing from Single Polymerase Molecules" Science (2009) 323:133-138.
Everts "RNA's Outfits The nucleic acid has dozens of chemical costumes" C&EN (2009) 87:36:65-68.
Fellers, J.P. "Genome Filtering Using Methylation-Sensitive Restriction Enzymes with Six Base Pair Recognition Sites" Plant Genome (2008) 1(2):146-152.
Finkel, T. et al. "Oxidants, oxidative stress and the biology of ageing" Nature (2000) 408(6809:239-247.
Flusberg, B.A. et al. "Direct detection of DNA methylation during single-molecule, real-time sequencing" Nat Meth (2010) 7(6):461-467.
Friedberg, E.C. "Suffering in Silence: The Tolerance of DNA Damage" Nat Rev Mol Cell Biol (2005) 6(12.):943-953.
Fromme, J.C. et al. "Base Excision Repair" Adv Protein Chem (2004) 69:1-41.
Hafner, M. et al. "Transcriptome-wide identification of RNA-binding protein and microRNA target sites by PAR-CLIP " Cell (2010) 141(1):129-141.
Hamm, M.L., et al. "Substrate Specificity of Fpg (MutM) and hOGG1, Two Repair Glycoylases" J Am Chem Soc. (2007) 129(25):7724-7725.
Hanes, J.W. et al. "Incorporation and replication of 8-oxo-deoxyguanosine by the human mitochrondrial DNA polymerase" J Biol Chem (2006) 281(47):36241-36248.
Hashimoto, H. et al. "The SRA domain of UHRF1 flaps 5-methylcytosine out of the DNA helix" Nature (2008) 455 (7214):826-829.
Hayatsu, H. "The bisuifite genomic sequencing used in the analysis of epigenetic states, a technique in the emerging environmental genotoxicology research" Mutation Res (2003) 659(1-2):77-82.
Hendrich, B, et al. "Identification and Characterization of a Family of Mammalian Methyl-CpG Binding Proteins" Mol Cell Biol (1998) 18((11):6538-6547.
Herbert, K.M. et al. "Single-Molecule Studies of RNA Polymerase: Motoring Along" Ann Rev Biochem (2008) 77:149-176.
Holmquist et al. "The bypass of DNA lesions by DNA and RNA polymerases" Mutat Res (2002) 510(1-2):1-7.
Horowitz, S. et al. "Mappin of N6-methyladenosine residues in bovine prolactin mRNA" PNAS (1984) 81 (18):5667-5671.
Hsu, G.W. et al. "Error-prone replicatin of oxidatively Damaged DNA by a high-fidelity DNA polymerase" Nature (2004) 431(7005:217-221.

Huang, T. H-M et al. "Identification of DNA Methylation Markers for Human Breast Carcinomas Using the Methylation-sensitive Restriction Fingerprinting Technique" Cancer Res (1997) 57:1030-1034.
Ingolia, N. T. et al. "Genome-Wide Analysis in Vivo of Translation with Nucleotide Resolution Using Ribosome Profiling" Science (2009) 324(5924):218-223.
Jones, P.A. et al. "Cancer epigenetics comes of age" Nat Genet (1999) 21(2):163-167.
Jorgensen, H.F. et al. "Engineering a high-affinity methyl-CpG-binding protein" Nucl Acids Res (2006) 34(13):e96.
Kannouche, P.L. et al. "Interaction of Human DNA Polymerase r with Monoubiquitinated PCNA: A Possible Mechanism for the Polymerase Switch in Response to DNA Damage" Mol Cell (2004) 14(4):491-500.
Kannouche, P.L. et al. Ubiquitination of PCNA and the Polymerase Switch in Human Cells Cell Cycle (2004) 3 (8):1011-1013.
Kilgore, J.A. et al. "Single-molecule and population probing of chromatin structure using DNA methyltransferases" Methods (2007) 41:320-332.
Klungland, A. et al. "Oxidative damage to purines in DNA: Role of Mammalian Ogg1 " DNA Repair (Amst) (2007) 6(4):481-488.
Kriaucionis, S. et al. "The Nuclear DNA Base 5-Hydroxymethylcytosine is Present in Purkinje Neurons and the Brain" Science (2009) 324(5929) :929-930.
Krueger, A.T. et al. "Model Systems for Understanding DNA Base Pairing" Chem & Biol (2009) 16(3):242-248.
Krueger, A.T. et al. "Redesigning the Architecture of the Base Pair: Toward Biochemical and Biological Function of New Genetic Sets" Curr Opin Chem Biol (2007) 11(69):588-594.
Laird, P.W. "The power and the promise of DNA methylation markers" Nat Rev Cancer (2003) 3(4):253-266.
Lehmann, A.R. "Replication of damaged DNA in mammalian cells: new solutions to an old problem" Mutant Res (2002) 509(1-2):23-34.
Lehmann, A.R. "Translesion synthesis in mammalian cells" Exp Cell Res (2006) 312(14):2673-2676.
Lehmann, A.R. et al. "Translesion synthesis: Y-family polymerases and the polymerase switch" DNA Repair (Amst) (2007) 6(7):891-899.
Levene, M.J. et al. "Zero-mode Waveguides for Single-Molecule Analysis at High Concentrations" Science (2003) 299(5607):682-686.
Lindahl, T. "Instability and decay of the primary structures of DNA" Nature (1993) 362(6422):709-715.
Lister, R. et al. "Finding the fifth base: Genome-wide sequencing of cytosine methylation" Genome Res (2009) 19:959-966.
Loakes, D, et al. "Polymerase engineering: towards the encoded synthesis of unnatural biopolymers" Chem Commun (2009) 31:4619-4631.
Ludlum, et al., "Ribonucleic Acid Polymerase Reactions with Methylated Polycytidylic Acid Templates," Journal of Biological Chemistry (1968) 243(10):2750-2753.
Masutani. C. et al. "The XPV (xeroderma pigmentosurn variant gene encodes human DNA polymease" Nature, (1999) 399(6737):700-704.
Matray, T.J. et al. "A specific partner for abasic damage in DNA" Nature (1999) 399:704-708.
McCullough, A.K et al. "Initiation of Base excision repair: glycosylase mechanisms and structures" Ann Rev Biochem (1999) 68-255-285.
Meissner, A. et al. "Genome-scale DNA methylation maps of pluripotents and differentiated cells" Nature (2008) 454:766-770 (+ supplementary information ).
Merino, E.J. et al. "RNA Structure Analysis at Single Nucleotide Resolution by Selective 2'-Hydroxyl Acylation and Primer Extension (SHAPE)" J Am Chem Soc. (2005)127:4223-4231.
Morgan, H.D. et al. "Activation-induced cytidine deaminase deaminates 5-methylcytosine in DNA and is expressed in pluripotent tissues" J Biol Chem (2004) 279:52353-52360.
Morozova, O. et al. "Applications of next generation sequencing technologies in functional genomics" Genomics (2008) 92:255-264. .
Narayan, P. et al. "Unequal Distribution of N6-Methyladenosine in Influenza Virus mRNAs" Mol Cell Biol (1987) 7(4):1572-1575.

(56) References Cited

OTHER PUBLICATIONS

Ohki, I et al. "Solution structures of the methyl-CpG-binding domain of the methylation-dependent transcriptional repressor MBD1" EMBO J (2000) 18(23):6653-6661.

Ohmori, "The Y-Famly of DNA Polymerases" et al. Mol Cell (2001) 8(1):7-8.

Okamoto, A. "5-Methylcytosine-Selective Osmium Oxidation" Nucleosides, Nucleotides. Nucleic Acids (2007) 26(10-12):1601-1604.

Petrov, A.I. et al. "Spin-labeled polyribonucleotids" Nucl Acids Res (1980) 8(18):4221-4234.

Radicella, J.P. et al. "Cloning and characterization of hOGG1, a human homolog of the OGG1 gene of Saccharomyces cerevisiae" PNAS (1997) 94:8010-8015.

Rollins, R.A. et al. "Large-scale structure of genomic methylation patterns" Genome Res (2006) 16-157-163.

Sadri, R. et al. "Rapid analysis of DNA methylation using new restriction enzyme sites created by bisulfite modification" Nucl Acids Res (1996) 24(24):5058-5059.

Seo, Y.J. et al, "Optimization of an Unnatural Base Pair toward Natural-Like Replication" J Am Chem Soc (2009) 131-3246-3252.

Smith, S.S. et al. "Mechanism of human methyl-directed DNA methyltransferase and the fidelity of cytosine methylation" PNAS (1992) 89:4744-4748.

Smolina, I.V. at al, "Pausing of DNA Polymerases on Duplex DNA Templates due to Ligand Binding in Vitro" J Mol Biol (2003) 326:1113-1125.

Tahiliani, M. et al. "Conversion of 5-Methyloytosine to 5-Hydroxymethylcytosine in Mammalian DNA by MLL Partner TET1" Science (2009) 324(5929):930-935.

Tahiliani, M. et al. "Supporting Online Material for Conversion of 5-Methyicytosine to 5-Hydroxymethylcytosine in Mammalian DNA by MLL Partner TET1" Science (2009) 324(5929):930-935.

Tanaka, K. et al. "Direct Labeling of 5-Methylcytosine and its Applications" J Am Chem Soc (2007) 129 (17):5612-5620.

Tijerina, P. et al. "DMS Footprinting of Structured RNAs and RNA-Protein Complexes" Nature Protocols (2007) 2:2608-2623.

Tost, et al., "DNA Methylation Analysis by Pyrosequencing," Nature Protocols (2007) 2(9):2265-2275.

Vidal. A.E. et al. "Mechanism of stimulation of the DNA glycosylase activity of hOGG1 by the major human AP endonuclease: bypass of the AP lyase activity step" Nucl Acids Res (2001) 29(8):1286-1292.

Viguera, E. et al, "Replication slippage involves DNA polymerase pausing and dissociation" EMBO J (2001) 20(10):2587-2595.

Weber, J. et al. "Chromosome wide and promoter-specific analyses identify sites of differential DNA methylation in normal and transformed human cells" Nat Genet (2005) 37:853-862.

Yebra, M.J. et al, "A Cytosine Methyltransferase Converts 5-Methylcytosine in DNA to Thymine" Biochemistry (1995) 34(45)14752-14757.

Zheng, K-W, et al. "Molecular crowding creates an essential environment for the formation of stable G-quadruplexes in long double-stranded DNA" Nucl Acids Res (2010) 38(1):327-338.

Abbotts, J. et al. "Studies on the Mechanism of Escherichia ColiDNA Polymerase I Large Fragment," Journal of Biologicai Chemistry (1988) 263:15094-15103.

Galas, D.J. et al. "DNAase Footprinting: A Simple Method for the Detection of Protein-DNA Binding Specificity" Nucleic Acids Research (1978) 5(9):3157-3170.

Vlassov, V.V. et al. "Extracellular Nucleic Acids" Bioessays (2207) 29(7):654-667.

Clark, T. et al. "Enhanced 5-Methylcytosine Detection in Single-Molecule, Real-Time Sequencing via Tet1 Oxidation" Biology (2013) 11:4, http://biomedcentral.com/1741-7007/11/4, BMC.

International Preliminary Report on Patentability dated Nov. 6, 2014 for related PCT/US2013/037829.

\* cited by examiner

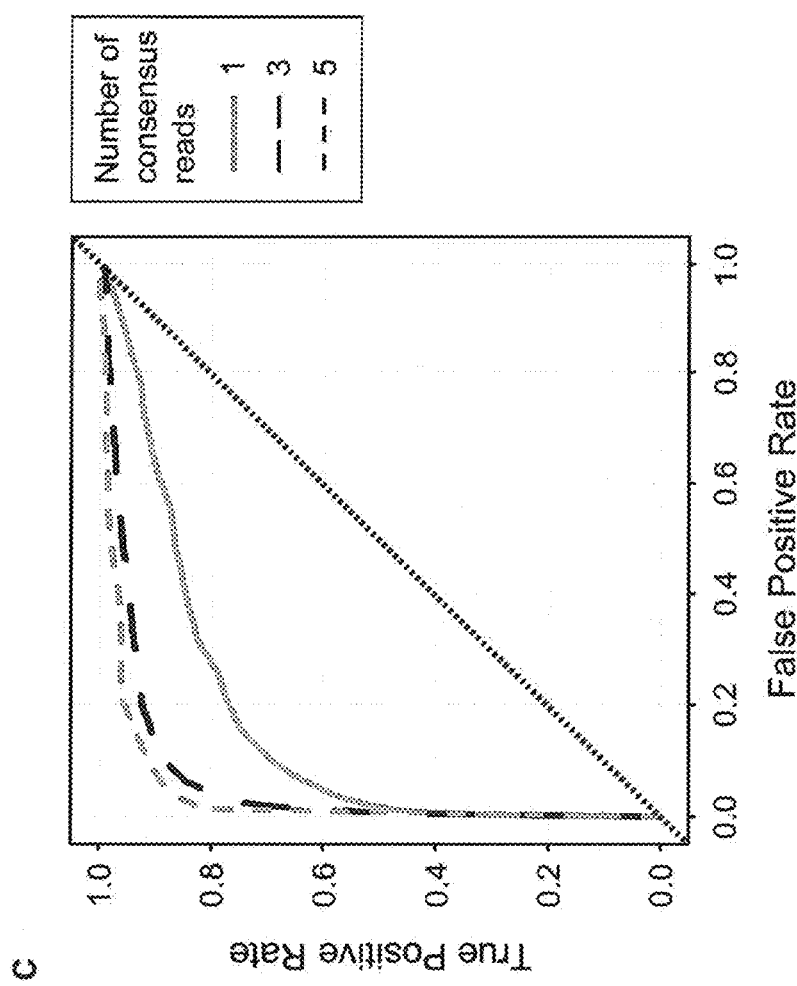
Figure 7, cont.

5-MeC templates

A. HpaII

B. HhaI 5-hmC-glu templates

A. HpaII    B. HhaI 5-caC templates

A. HpaII

B. HhaI

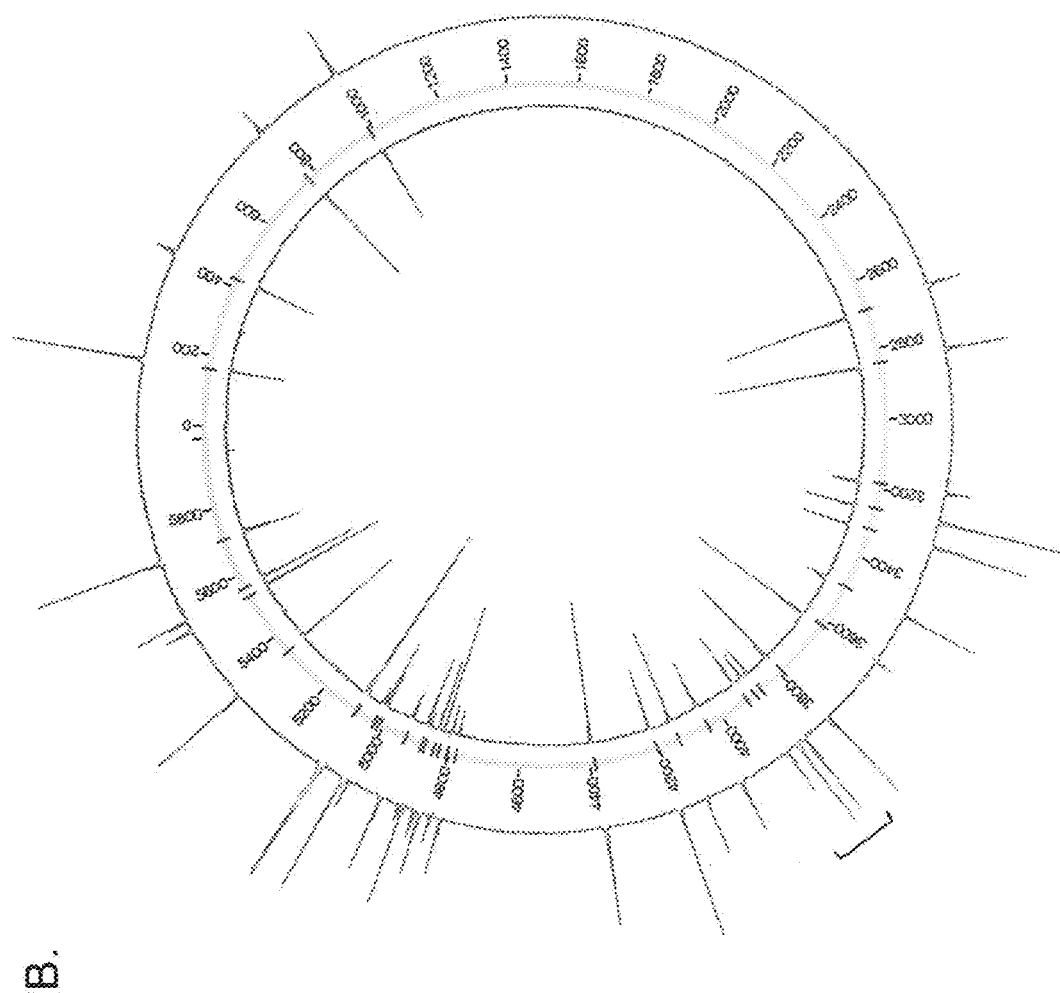
Figure 21, cont.

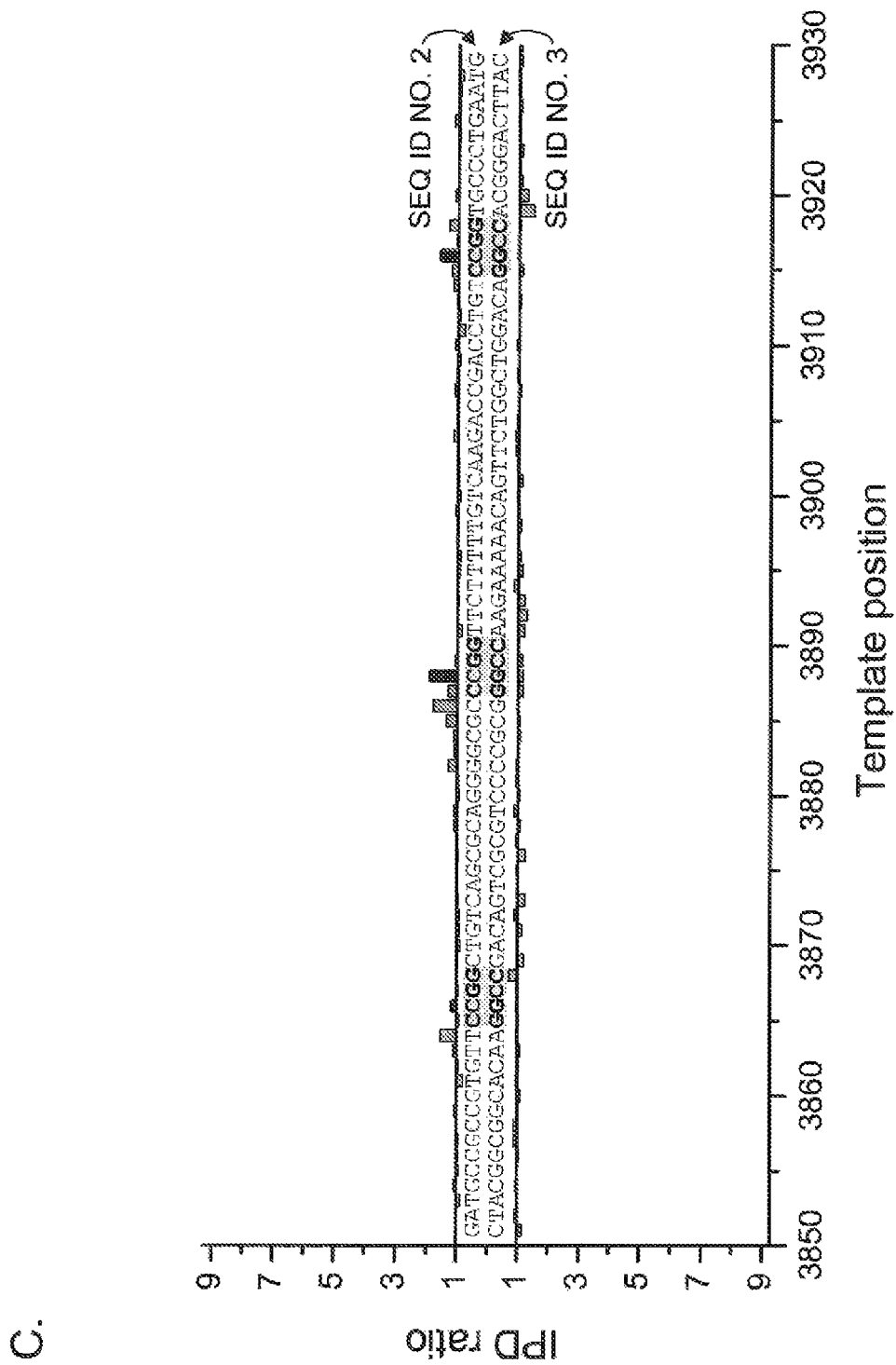
Figure 21, cont.

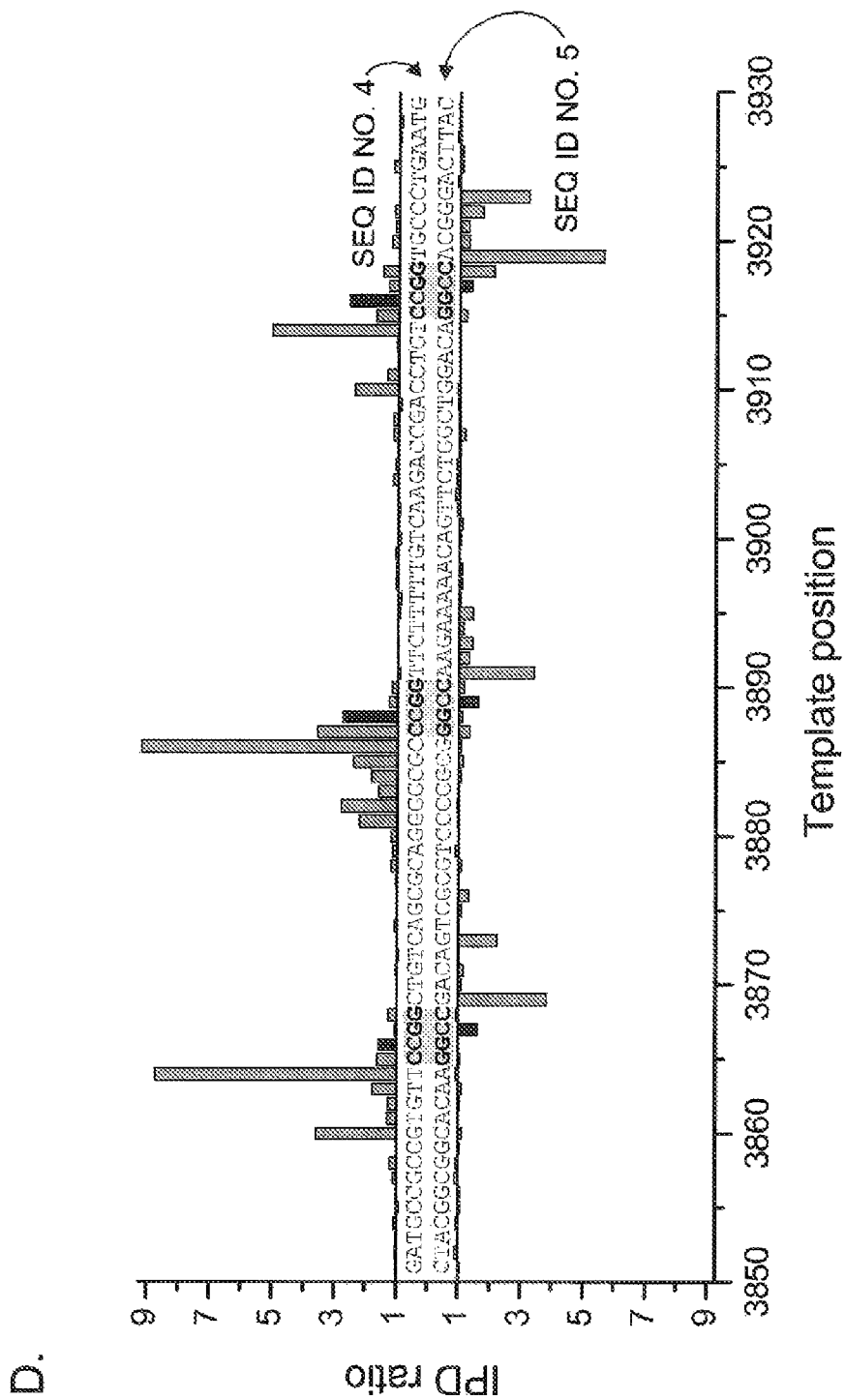
Figure 21, cont.

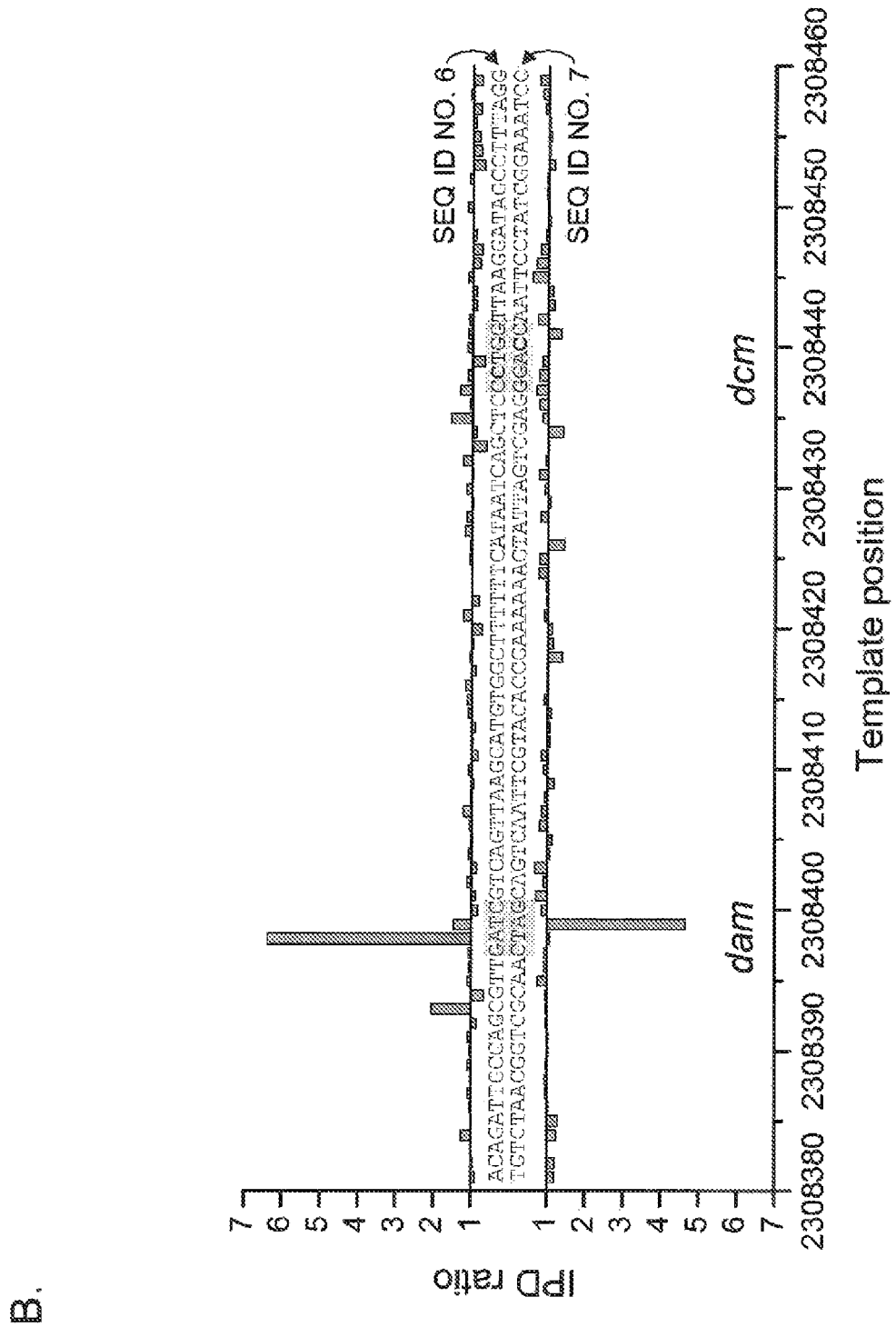
Figure 22, cont.

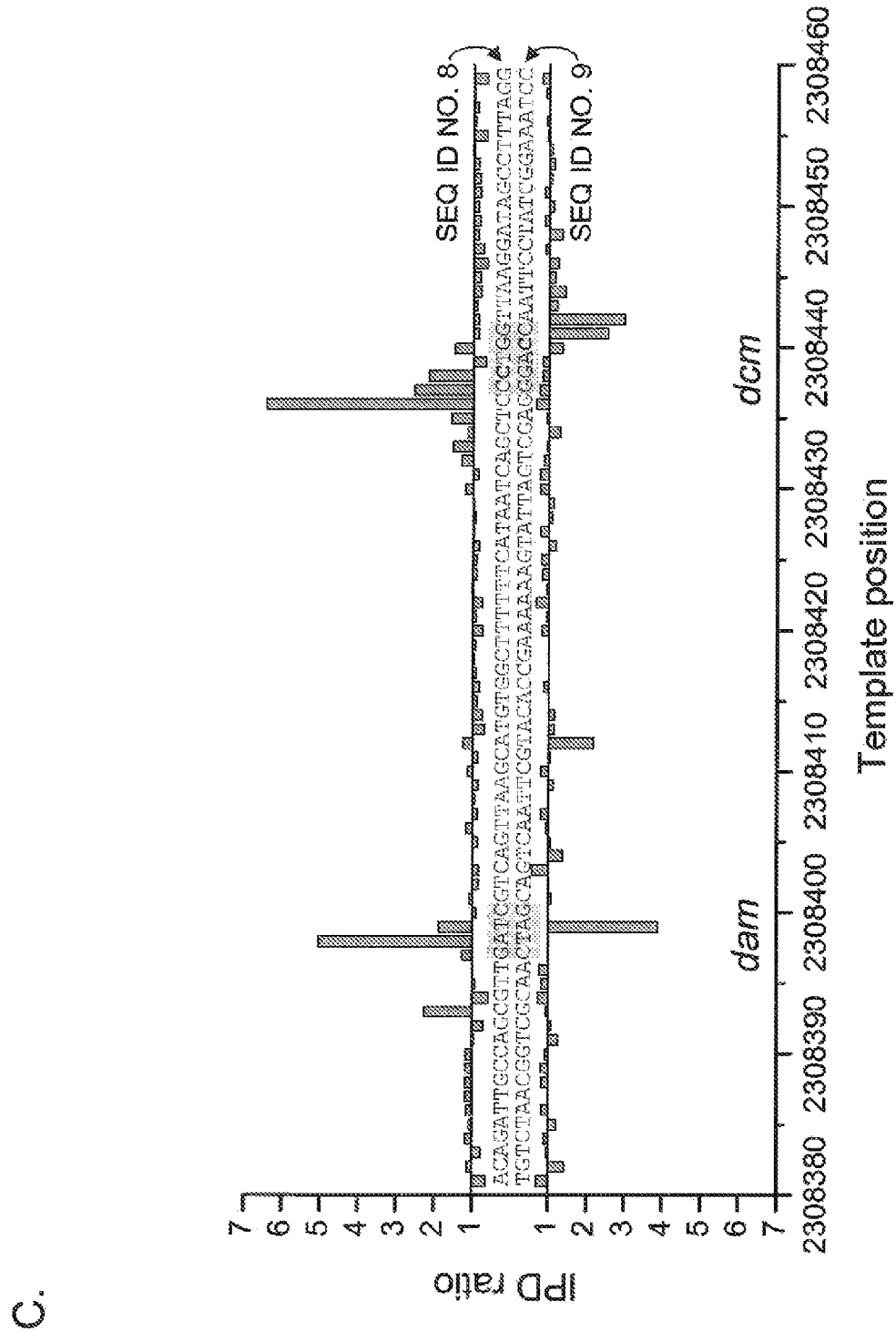
Figure 22, cont.

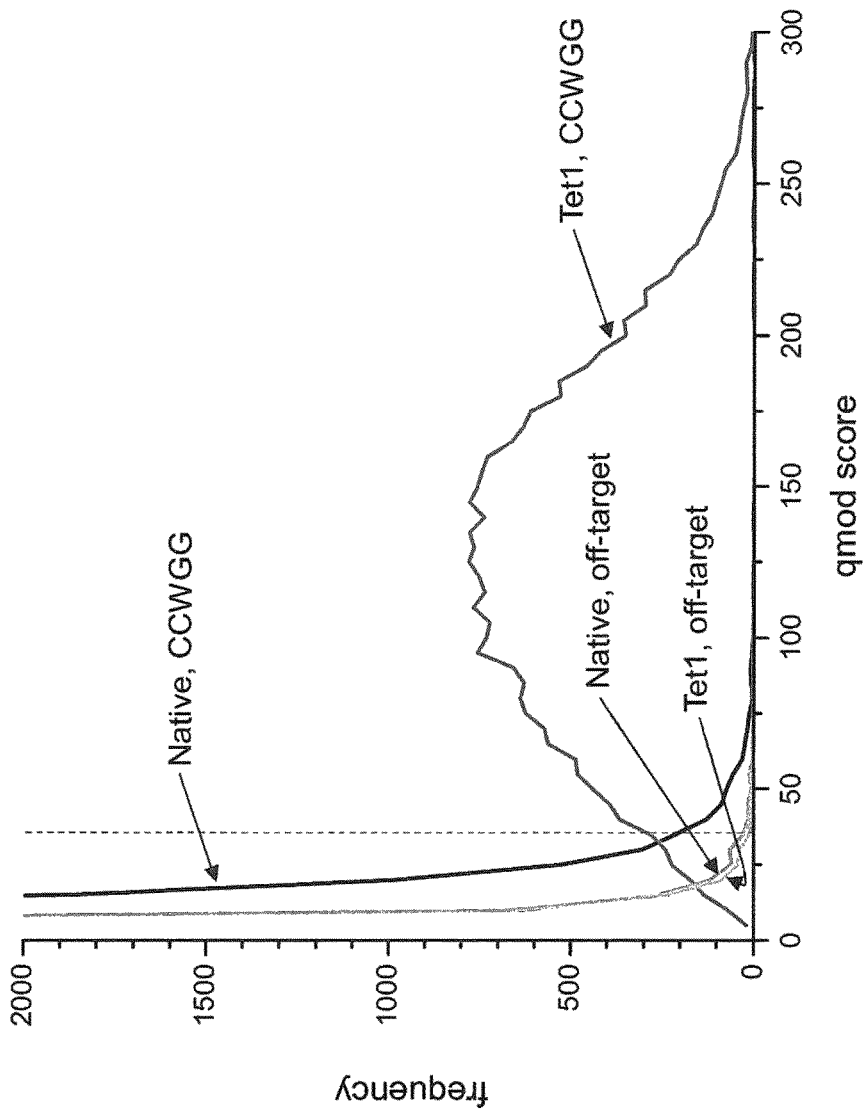
Figure 22, cont.

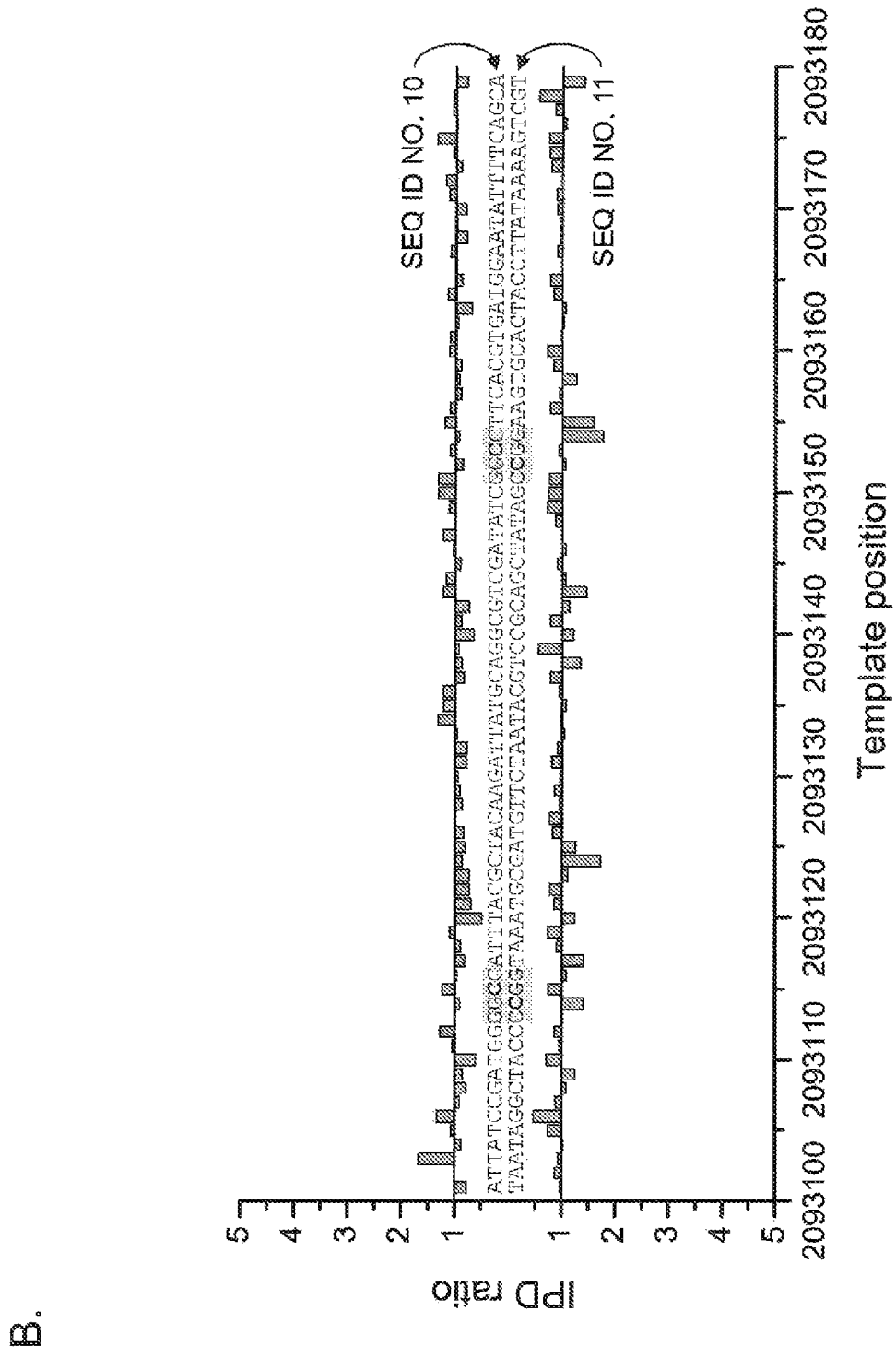
Figure 23, cont.

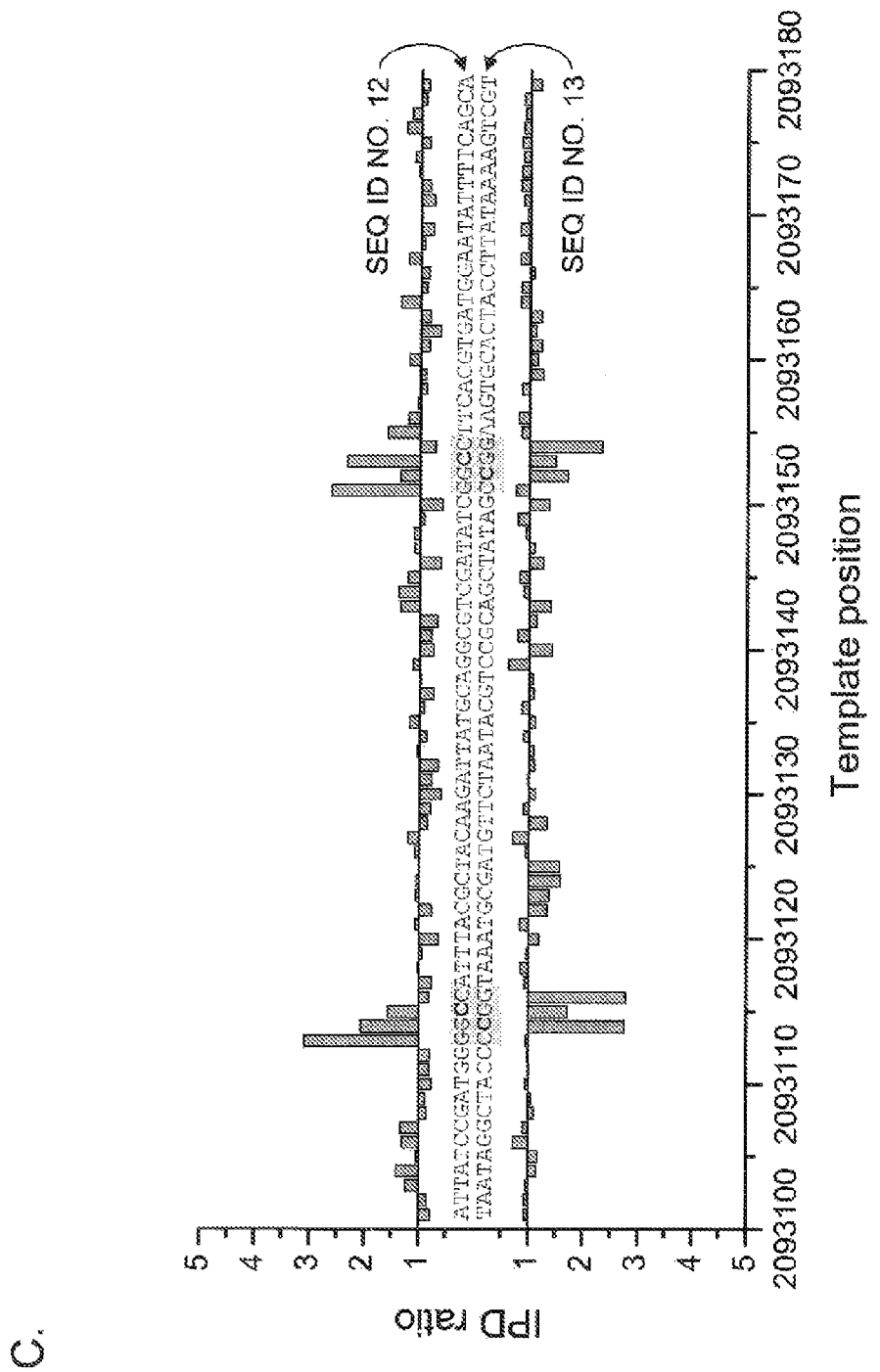
Figure 23, cont.

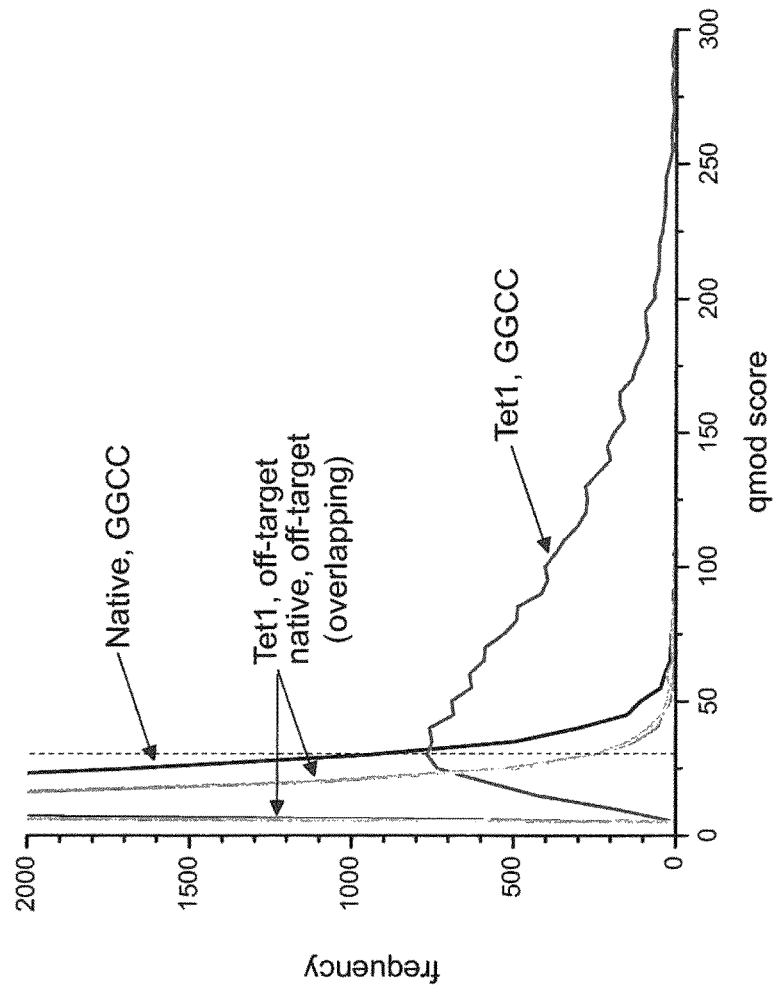
Figure 23, cont.

SEQUENCE LISTING

<160> NUMBER OF SEQ ID NOS: 13

<210> SEQ ID NO 1
<211> LENGTH: 199
<212> TYPE: DNA
<213> ORGANISM: Artificial Sequence
<220> FEATURE:
<223> OTHER INFORMATION: Circular sequencing template
<220> FEATURE:
<221> NAME/KEY: misc_structure
<222> LOCATION: (1)..(199)
<223> OTHER INFORMATION: circular molecule
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (35)..(35)
<223> OTHER INFORMATION: m5c
<220> FEATURE:
<221> NAME/KEY: modified_base
<222> LOCATION: (164)..(164)
<223> OTHER INFORMATION: m5c
<220> FEATURE:
<221> NAME/KEY: modified_base
<222> LOCATION: (183)..(183)
<223> OTHER INFORMATION: m5c

<400> SEQUENCE: 1
aagttccgag cccgacgcat gatctgtact tgatcgaccg tgcaacgcat gatctgtact    60
tgatcgaccg tgcacttctc tctctctttt cctcctcctc cgttgttgtt gttgagagag    120
agaagtgcac ggtcgatcaa gtacagatca tgcgttgcac ggtcgatcaa gtacagatca    180
tgcgtcgggc tcggaacga                                                 199

<210> SEQ ID NO 2
<211> LENGTH: 79
<212> TYPE: DNA
<213> ORGANISM: Artificial Sequence
<220> FEATURE:
<223> OTHER INFORMATION: Sequencing template
<220> FEATURE:
<221> NAME/KEY: modified_base
<222> LOCATION: (16)..(16)
<223> OTHER INFORMATION: m5c
<220> FEATURE:
<221> NAME/KEY: modified_base
<222> LOCATION: (38)..(38)
<223> OTHER INFORMATION: m5c
<220> FEATURE:
<221> NAME/KEY: modified_base
<222> LOCATION: (66)..(66)
<223> OTHER INFORMATION: m5c

<400> SEQUENCE: 2
gatgccgccg tgttccggct gtcagcgcag gggcgcccgg ttcttttttgt caagaccgac    60 ctgtccggtg ccctgaatg                                                 79

<210> SEQ ID NO 3
<211> LENGTH: 79
<212> TYPE: DNA
<213> ORGANISM: Artificial Sequence
<220> FEATURE:
<223> OTHER INFORMATION: Sequencing template
<220> FEATURE:
<221> NAME/KEY: modified_base
<222> LOCATION: (13)..(13)
<223> OTHER INFORMATION: m5c
<220> FEATURE:
<221> NAME/KEY: modified_base

```
<222> LOCATION: (41)..(41)
<223> OTHER INFORMATION: m5c
<220> FEATURE:
<221> NAME/KEY: modified_base
<222> LOCATION: (63)..(63)
<223> OTHER INFORMATION: m5c

<400> SEQUENCE: 3
cattcagggc accggacagg tcggtcttga caaaaagaac cgggcgcccc tgcgctgaca    60
gccggaacac ggcggcatc                                                 79

<210> SEQ ID NO 4
<211> LENGTH: 79
<212> TYPE: DNA
<213> ORGANISM: Artificial Sequence
<220> FEATURE:
<223> OTHER INFORMATION: Sequencing template
<220> FEATURE:
<221> NAME/KEY: modified_base
<222> LOCATION: (16)..(16)
<223> OTHER INFORMATION: 5-carboxycytidine
<220> FEATURE:
<221> NAME/KEY: modified_base
<222> LOCATION: (38)..(38)
<223> OTHER INFORMATION: 5-carboxycytidine
<220> FEATURE:
<221> NAME/KEY: modified_base
<222> LOCATION: (66)..(66)
<223> OTHER INFORMATION: 5-carboxycytidine

<400> SEQUENCE: 4
gatgccgccg tgttccggct gtcagcgcag gggcgcccgg ttcttttttgt caagaccgac   60 ctgtccggtg ccctgaatg                                                 79

<210> SEQ ID NO 5
<211> LENGTH: 79
<212> TYPE: DNA
<213> ORGANISM: Artificial Sequence
<220> FEATURE:
<223> OTHER INFORMATION: Sequencing template
<220> FEATURE:
<221> NAME/KEY: modified_base
<222> LOCATION: (13)..(13)
<223> OTHER INFORMATION: 5-carboxycytidine
<220> FEATURE:
<221> NAME/KEY: modified_base
<222> LOCATION: (41)..(41)
<223> OTHER INFORMATION: 5-carboxycytidine
<220> FEATURE:
<221> NAME/KEY: modified_base
<222> LOCATION: (63)..(63)
<223> OTHER INFORMATION: 5-carboxycytidine

<400> SEQUENCE: 5
cattcagggc accggacagg tcggtcttga caaaaagaac cgggcgcccc tgcgctgaca    60
gccggaacac ggcggcatc                                                 79

<210> SEQ ID NO 6
<211> LENGTH: 79
<212> TYPE: DNA
<213> ORGANISM: Escherichia coli
<220> FEATURE:
<221> NAME/KEY: modified_base
<222> LOCATION: (18)..(18)
<223> OTHER INFORMATION: m6a
<220> FEATURE:
<221> NAME/KEY: modified_base
<222> LOCATION: (58)..(58)
<223> OTHER INFORMATION: m5c
```

<400> SEQUENCE: 6
acagattgcc agcgttgatc gtcagttaag catgtggctt ttttcataat cagctccctg    60
gttaaggata gcctttagg                                                  79

<210> SEQ ID NO 7
<211> LENGTH: 79
<212> TYPE: DNA
<213> ORGANISM: Escherichia coli
<220> FEATURE:
<221> NAME/KEY: modified_base
<222> LOCATION: (20)..(20)
<223> OTHER INFORMATION: m5c
<220> FEATURE:
<221> NAME/KEY: modified_base
<222> LOCATION: (61)..(61)
<223> OTHER INFORMATION: m6a

<400> SEQUENCE: 7
cctaaaggct atccttaacc agggagctga ttatgaaaaa agccacatgc ttaactgacg    60
atcaacgctg gcaatctgt                                                  79

<210> SEQ ID NO 8
<211> LENGTH: 79
<212> TYPE: DNA
<213> ORGANISM: Escherichia coli
<220> FEATURE:
<221> NAME/KEY: modified_base
<222> LOCATION: (18)..(18)
<223> OTHER INFORMATION: m6a
<220> FEATURE:
<221> NAME/KEY: modified_base
<222> LOCATION: (58)..(58)
<223> OTHER INFORMATION: 5-carboxycytidine

<400> SEQUENCE: 8
acagattgcc agcgttgatc gtcagttaag catgtggctt ttttcataat cagctccctg    60
gttaaggata gcctttagg                                                  79

<210> SEQ ID NO 9
<211> LENGTH: 79
<212> TYPE: DNA
<213> ORGANISM: Escherichia coli
<220> FEATURE:
<221> NAME/KEY: modified_base
<222> LOCATION: (20)..(20)
<223> OTHER INFORMATION: 5-carboxycytidine
<220> FEATURE:
<221> NAME/KEY: modified_base
<222> LOCATION: (61)..(61)
<223> OTHER INFORMATION: m6a

<400> SEQUENCE: 9
cctaaaggct atccttaacc agggagctga ttatgaaaaa agccacatgc ttaactgacg    60
atcaacgctg gcaatctgt                                                  79

<210> SEQ ID NO 10
<211> LENGTH: 79
<212> TYPE: DNA
<213> ORGANISM: Bacillus halodurans
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (53)..(53)
<223> OTHER INFORMATION: m5c

```
<400> SEQUENCE: 10
attatccgat ggggccattt acgctacaag attatgcagg cgtcgatatc ggccttcacg      60
tgatggaata ttttcagca                                                   79

<210> SEQ ID NO 11
<211> LENGTH: 79
<212> TYPE: DNA
<213> ORGANISM: Bacillus halodurans
<220> FEATURE:
<221> NAME/KEY: modified_base
<222> LOCATION: (28)..(28)
<223> OTHER INFORMATION: m5c
<220> FEATURE:
<221> NAME/KEY: modified_base
<222> LOCATION: (66)..(66)
<223> OTHER INFORMATION: m5c

<400> SEQUENCE: 11
tgctgaaaat attccatcac gtgaaggccg atatcgacgc ctgcataatc ttgtagcgta      60
aatggcccca tcggataat                                                   79

<210> SEQ ID NO 12
<211> LENGTH: 79
<212> TYPE: DNA
<213> ORGANISM: Bacillus halodurans
<220> FEATURE:
<221> NAME/KEY: modified_base
<222> LOCATION: (15)..(15)
<223> OTHER INFORMATION: 5-carboxycytidine
<220> FEATURE:
<221> NAME/KEY: modified_base
<222> LOCATION: (53)..(53)
<223> OTHER INFORMATION: 5-carboxycytidine

<400> SEQUENCE: 12
attatccgat ggggccattt acgctacaag attatgcagg cgtcgatatc ggccttcacg      60
tgatggaata ttttcagca                                                   79

<210> SEQ ID NO 13
<211> LENGTH: 79
<212> TYPE: DNA
<213> ORGANISM: Bacillus halodurans
<220> FEATURE:
<221> NAME/KEY: modified_base
<222> LOCATION: (28)..(28)
<223> OTHER INFORMATION: 5-carboxycytidine
<220> FEATURE:
<221> NAME/KEY: modified_base
<222> LOCATION: (66)..(66)
<223> OTHER INFORMATION: 5-carboxycytidine

<400> SEQUENCE: 13
tgctgaaaat attccatcac gtgaaggccg atatcgacgc ctgcataatc ttgtagcgta      60
aatggcccca tcggataat                                                   79
```

IDENTIFICATION OF 5-METHYL-C IN NUCLEIC ACID TEMPLATES

CROSS-REFERENCE TO RELATED APPLICATIONS

This application claims the benefit of U.S. Provisional Application No. 61/637,687, filed Apr. 24, 2012, the full disclosure of which is incorporated herein by reference in its entirety for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only 6 KB file (06000101_2013-08-30_SequenceListing.txt).

STATEMENT OF FEDERALLY SPONSORED RESEARCH

This invention was made with government support under Grant GM071440 awarded by the NIH. The government has certain rights in the invention.

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

A stereotypical example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in, the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, reversible methylation of the 5' position of cytosine by methyltransferases is one of the most widely studied epigenetic modifications. In mammals, 5-methylcytosine (5-MeC) frequently occurs at CpG dinucleotides, which often cluster in regions called CpG islands that are at or near transcription start sites. Methylation of cytosine in CpG islands can interfere with transcription factor binding and is associated with transcription repression and gene regulation. In addition, DNA methylation is known to be essential for mammalian development and has been associated with cancer and other disease processes. Recently, a new 5-hydroxymethylcytosine epigenetic marker has been identified in certain cell types in the brain, suggesting that it plays a role in epigenetic control of neuronal function (S. Kriaucionis, et al., *Science* 2009, 324(5929): 929-30, incorporated herein by reference in its entirety for all purposes). Further information on cytosine methylation and its impact on gene regulation, development, and disease processes is provided in the art, e.g., in A. Bird, *Genes Dev* 2002, 16, 6; M. Gardiner-Garden, et al., *J Mol Biol* 1987, 196, 261; S. Saxonov, et al., *Proc Natl Acad Sci USA* 2006, 103, 1412; R. Jaenisch, et al., *Nat Genet.* 2003, 33 *Suppl*, 245; E. Li, et al., *Cell* 1992, 69, 915; A. Razin, et al., *Hum Mol Genet.* 1995, 4 *Spec No*, 1751; P. A. Jones, et al., *Nat Rev Genet.* 2002, 3, 415; P. A. Jones, et al., *Cancer Res* 2005, 65, 11241; P. A. Jones, et al., *Nat Genet.* 1999, 21, 163; K. R. Pomraning, et al., *Methods* 2009, 47, 142; and K. D. Robertson, *Nat Rev Genet.* 2005, 6, 597, all of which are incorporated herein by reference in their entireties for all purposes.

Bisulfite sequencing is the current method of choice for single-nucleotide resolution methylation profiling (S. Beck, et al., *Trends Genet.* 2008, 24, 231; and S. J. Cokus, et al., *Nature* 2008, 452, 215, the disclosures of which are incorporated herein by reference in their entireties for all purposes). Treatment of DNA with bisulfite converts unmethylated cytosine, but not 5-MeC, to uracil (M. Frommer, et al., *Proc Natl Acad Sci USA* 1992, 89, 1827, incorporated herein by reference in its entirety for all purposes). The DNA is then amplified (which converts all uracils into thymines) and subsequently analyzed with various methods, including microarray-based techniques (R. S. Gitan, et al., *Genome Res* 2002, 12, 158, incorporated herein by reference in its entirety for all purposes) or $2^{nd}$-generation sequencing (K. H. Taylor, et al., *Cancer Res* 2007, 67, 8511; and R. Lister, et al., *Cell* 2008, 133, 523, both incorporated herein by reference in their entireties for all purposes). While bisulfite-based techniques have greatly advanced the analysis of methylated DNA, they also have several drawbacks. First, bisulfite sequencing requires a significant amount of sample preparation time (K. R. Pomraning, et al., supra). Second, the harsh reaction conditions necessary for complete conversion of unmethylated cytosine to uracil lead to degradation of DNA (C. Grunau, et al., *Nucleic Acids Res* 2001, 29, E65, incorporated herein by reference in its entirety for all purposes), and thus necessitate large starting amounts of the sample, which can be problematic for some applications. Furthermore, because bisulfite sequencing also suffers from the same limitations as do the microarray or second-generation DNA sequencing technologies upon which it depends. For example, the reduction in sequence complexity caused by bisulfite conversion makes it difficult to design enough unique probes for genome-wide profiling (S. Beck, et al., supra), and the short reads of most second-generation DNA sequencing techniques are difficult to align to highly repetitive genomic regions (K. R. Pomraning, et al., supra), such as the CpG islands that are often methylated. Given these limitations, bisulfite sequencing is also not well suited for de novo methylation profiling (S. Beck, et al., supra).

In another widely used technique, methylated DNA immunoprecipitation (MeDIP), an antibody against 5-MeC is used to enrich for methylated DNA sequences (M. Weber, et al., *Nat Genet.* 2005, 37, 853, incorporated herein by reference in its entirety for all purposes). MeDIP has many advantageous attributes for genome-wide assessment of methylation status, but it does not offer as high base resolution as bisulfite treatment-based methods, and is hampered by the same limitations of current microarray and second-generation sequencing technologies.

Research efforts aimed at increasing our understanding of the human methylome would benefit greatly from the development of a new methylation profiling technology that does not suffer from the limitations described above. Accordingly, there exists a need for improved techniques for detection of modifications in nucleic acid sequences, and particularly nucleic acid methylation.

Typically, modeled biological systems rely on bulk reactions that ascertain general trends of biological reactions and provide indications of how such bulk systems react to different effectors. While such systems are useful as models of bulk reactions in viva, a substantial amount of information is lost in the averaging of these bulk reaction results. In particular, the activity of and effects on individual molecular complexes cannot generally be teased out of such bulk data collection strategies.

Single-molecule real-time analysis of nucleic acid synthesis has been shown to provide powerful advantages over nucleic acid synthesis monitoring that is commonly exploited in sequencing processes. In particular, by concurrently monitoring the synthesis process of nucleic acid polymerases as they work in replicating nucleic acids, one gains advantages of a system that has been perfected over millions of years of evolution. In particular, the natural DNA synthesis processes provide the ability to replicate whole genomes in extremely short periods of time, and do so with an extremely high level of fidelity to the underlying template being replicated.

The present invention is directed to a variety of different single-molecule real-time analyses for monitoring the progress and effectors of biological reactions, and in particular detecting modifications in nucleic acid sequences. For example, the present invention provides a direct methylation sequencing technology that comprises observing the kinetics of single polymerase molecules in real time and with high multiplex. This technique will provide for fast and economical analysis of methylation patterns, even in repetitive genomic regions.

BRIEF SUMMARY OF THE INVENTION

The present invention is generally directed to the detection of modified nucleic acid sequences, and particularly the detection of methylated bases within nucleic acid sequences using a real time direct detection of such methylated sites. The present invention is expected to have a major impact on research aiming to illuminate the role of DNA methylation in human health.

In certain aspects of the invention, methods are provided for identification of a modification in a nucleic acid molecule. In general, a template nucleic acid comprising the modification and an enzyme capable of processing the template are provided. The template nucleic acid is contacted with the enzyme, and the subsequent processing of the template by the enzyme is monitored. A change or perturbation in the processing is detected, and this change is indicative of the presence of the modification in the template. Exemplary modifications that can be detected by the methods of the invention include, but are not limited to methylated bases (e.g., 5-methylcytosine, $N^6$-methyladenosine, etc.), pseudouridine bases, 7,8-dihydro-8-oxoguanine bases, 2'-O-methyl derivative bases, base J, base P, base Z, s4U, s6G, nicks, apurinic sites, apyrimidic sites, and non-canonical bases or base pairs. In preferred embodiments, nucleotides or analogs thereof that are incorporated into a nascent strand synthesized by the enzyme are distinctly labeled to allow identification of a sequence of specific nucleotides or nucleotide analogs so incorporated. In certain preferred embodiments, labels are linked to nucleotides or nucleotide analogs through a phosphate group, e.g., a phosphate group other than the alpha phosphate group. As such, the labels are removed from the nucleotide or nucleotide analog upon incorporation into the nascent strand.

In some embodiments, the template nucleic acid is treated prior to processing by the enzyme, e.g., to alter the modification. The treatment may be chemical or enzymatic, and includes, e.g., glycosylase modification, bisulfite modification, hydroxylation, TET1 modification, and cytidine deaminase modification. In some embodiments, the methods comprise both treatment of the template and incorporation of non-natural nucleotide analogs into the nascent strand.

In certain embodiments, the template nucleic acid comprises regions of internal complementarity (e.g., a double-stranded portion) and at least one single-stranded portion, and preferably the modification is located within at least one of the regions of internal complementarity. In certain embodiments, the template is a circular template. In certain embodiments, the template is a circular template comprising at least two regions of internal complementarity. In certain embodiments, the enzyme is a polymerase, such as a DNA polymerase, and RNA polymerase, a reverse transcriptase, or a derivative or variant thereof. In preferred embodiments, the enzyme is a polymerase enzyme capable of strand displacement. In specific embodiments, the enzyme is a 129 polymerase, optionally comprising at least one mutation at a position selected from the group consisting of K392, K422, I93, M188, K392, V399, T421, K422; S95, Y101, M102; Q99, L123, K124, T189, A190; G191, S388; P127, L384, N387, S388; and L389, Y390, and G391.

Examples of changes in the processing of the template by the enzyme that are monitored in various embodiments of the invention include, but are not limited to, kinetics, processivity, affinity, rate, strand-displacement activity, signal characteristics, error metrics, signal context, and the like. In some embodiments, a change or perturbation of enzyme activity occurs only at the modification, and in other embodiments the change or perturbation occurs at one or more positions proximal to the modification, which may also include the modification position.

In certain aspects, the methods further comprise mapping the modification. In certain preferred embodiments, mapping the modification comprises analyzing a portion of the sequence read that was generated immediately prior to, during, and/or immediately after detecting the change in processing to determine a sequence complementary to the template nucleic acid; determining the complement of the sequence complementary to the template nucleic acid; and mapping the modification at a position in the template nucleic acid that is proximal to the complement of the sequence complementary to the template nucleic acid. Where the template is a double-stranded nucleic acid, the modification can be on or within a strand of the template being used by a polymerase to generate a complementary nascent strand, or can be on or within a strand being displaced by the polymerase during nascent strand synthesis. In either case, a modification can be mapped to a region of the template where such a change or perturbation in processing is observed.

In certain embodiments, a change or perturbation in the processing that is indicative of the modification is a kinetic difference in the processing (e.g., detected as an alteration in one or more of interpulse duration, pulse width, processivity, cessation of processing (e.g., pausing or stalling), etc.) and/or a change in an error metric (e.g., accuracy, an increase in binding events that do not result in incorporation (e.g., cognate or non-cognate sampling), etc.) The change in processing can be indicative of the type of modification present in the template nucleic acid, since different types of modifications have different effects on the activity and/or fidelity of the enzyme resulting in different observed changes or perturbations during the reaction.

In preferred embodiments, the monitoring occurs in real time during the processing of the template by the enzyme. In preferred embodiments, the template nucleic acid and the enzyme form a complex that is immobilized at a reaction site on a substrate, and in more preferred embodiments a plurality of complexes are immobilized at optically resolvable reaction sites on the substrate, wherein a single complex immobilized at one of the reaction sites is optically resolvable from any other of the complexes immobilized at any other of the reaction sites. In certain embodiments, the optically resolvable reaction sites are nanometer-scale apertures in the substrate, and can be optical confinements, such as zero-mode waveguides. In preferred embodiments, the template nucleic acid is plurality of template nucleic acids that are optically resolvable from one another during the monitoring. Preferably, the template nucleic acid is not amplified prior to contacting it with the enzyme.

In certain aspects, the invention provides methods for identifying modifications within nucleic acids molecules comprising introducing a further modification into a template nucleic acid already comprising a modification of interest. An enzyme processes the template nucleic acid, and the processing of the template by the enzyme is monitored. Changes in the processing are indicative of the further modification, and therefore, indirectly, the modification of interest is identified. The modification of interest can be any modification useful for directing or marking the template to facilitate introduction of the further modification. For example, the modification of interest can be chosen from the following: a methylated base, a hydroxymethylated base, HOMedU, β-D-glucosyl-HOMedU, and cytosine-5-methylenesulfonate. In some preferred embodiments, the template nucleic acid comprises a single-stranded portion and a double-stranded portion, and in some cases the double-stranded portion is a result of complementarity between two separate portions of the template nucleic acid. In some embodiments, the template nucleic acid comprises a first polynucleotide region comprising the modification and a second polynucleotide region complementary to the first polynucleotide region, where the first polynucleotide region and the second polynucleotide region are on a single strand of the template nucleic acid, e.g., in different regions of a single-stranded circular template nucleic acid. Typically, the template nucleic acid is subjected to a treatment to introduce the further modification, and such a treatment can comprise exposure to a modifying agent, e.g., a glycosylase, bisulfite, a hydroxylase (e.g., Tet1 protein), and a cytidine deaminase. For example, the treatment can comprise exposure to a Tet1 protein that converts a 5-MeC to a 5-fC base and/or a 5-caC base. The treatment can also comprise addition of a sugar moiety (e.g., sucrose, glucose, maltose, galactose, dextrose, lactose, etc.) or group to a nucleobase comprising the modification. The addition of the sugar moiety serves to increase the response of the enzyme, e.g., polymerase, resulting in a greater change is processing that would occur in the absence of the sugar moiety. For example, the nucleobase can be a hydroxymethylcytosine nucleobase, which is converted to β-glucosyl-5-hydroxymethylcytosine by the addition of the sugar moiety. In certain preferred embodiments, the processing of the template is monitored for kinetic changes or perturbations, which can be indicative of a modification or a further modification. The nucleic acid template can be RNA or DNA, or can comprise both ribo- and deoxyribonucleotides, and is preferably not amplified. The enzyme is preferably a polymerase enzyme, e.g., a DNA polymerase, and RNA polymerase, a reverse transcriptase, or a derivative thereof. Preferably, the processing is a sequencing reaction (e.g., a single-molecule sequencing reaction), and where the template is a closed circular template and the polymerase is capable of strand displacement, the processing can comprise rolling-circle replication of the template, which can generate redundant sequence data for the template. The change in processing can occur at the modification or further modification, or can occur at one or more positions upstream or downstream of the modification or further modification, and can be a kinetic change such as an alteration in interpulse duration or pulse width. The change in processing is preferably indicative of the type of modification and/or further modification present in the template. In certain embodiments, mapping the modification further comprises analyzing a portion of the sequence read that was generated immediately prior to, during, or immediately after the detecting the change in processing to determine a sequence complementary to the template nucleic acid; determining the complement of the sequence complementary to the template nucleic acid; and mapping the modification at a position in the template nucleic acid that is proximal to the complement of the sequence complementary to the template nucleic acid. In preferred embodiments, the monitoring occurs in real time during the processing. In further aspects, the template nucleic acid and enzyme form a complex that is immobilized at a reaction site on a substrate, and a plurality of such complexes can be immobilized at optically resolvable reaction sites on the substrate. Optionally, these optically resolvable reaction sites are nanometer-scale apertures in the substrate, preferably with optical confinement properties, e.g., such as zero-mode waveguides.

In certain aspects, the invention provides methods for identifying modifications that comprise providing both a template nucleic acid comprising the modification and an enzyme (e.g., a polymerase enzyme) capable of processing the template nucleic acid; contacting the template nucleic acid with the enzyme; monitoring processing of the template nucleic acid by the enzyme; and detecting a change in the kinetics of the processing, wherein the change is indicative of the modification, thereby identifying the modification. In certain embodiments, the modification is a methylated cytosine base or a methylated adenine base. In some embodiments, the template nucleic acid comprises a first polynucleotide region comprising the modification and a second polynucleotide region complementary to the first polynucleotide region, where the first polynucleotide region and the second polynucleotide region are on a single strand of the template nucleic acid. Optionally, the template nucleic acid can be subjected to a treatment to alter the modification prior to or coincident with the contacting. In preferred embodiments, the processing results in the synthesis of a nascent nucleic acid strand, and further wherein the monitoring detects incorporation of single nucleotides into the nascent nucleic acid strand to generate a sequence read that is complementary to the template nucleic acid. For example, the single nucleotides can be differentially labeled to be distinguishable from one another during the monitoring, and preferably the single nucleotides can comprise a label linked to a phosphate group, wherein the phosphate group is removed during the processing. The monitoring preferably occurs in real time during the processing such that the monitoring occurs during the process of binding and incorporation. The monitoring typically comprises monitoring both the sequence of bases incorporated, and the kinetics of the incorporation events. Reaction kinetics that can be monitored include, but are not limited to, pulse width, pulse height, interpulse distance/duration, kinetics of cognate or non-cognate sampling, error metrics, rate of incorporation, pausing, and the like. Further, in preferred embodiments, the enzyme is allowed to processively and continuously incorporate bases (e.g., bases that do not comprise a blocking group) into a nascent strand during the monitoring. Where the enzyme is a polymerase, the processing is generally nascent strand synthesis, and in certain embodiments is rolling-circle synthesis of a nascent, nucleic acid strand complementary to the template nucleic acid. In certain embodiments, the template nucleic acid and enzyme form a complex that is immobilized at a reaction site on a substrate, and in some cases a plurality of complexes are immobilized at optically resolvable reaction sites on the substrate, wherein a single complex immobilized at one of the reaction sites is optically resolvable from any other of the complexes immobilized at any other of the reaction sites.

In certain aspects of the invention, methods are provided for identifying a 5-MeC in a template nucleic acid. In preferred embodiments, such methods comprise providing a template nucleic acid comprising the 5-MeC; converting the 5-MeC into a further modification by treating the template nucleic acid with a Tet protein, wherein the further modification is selected from 5-caC and 5-fC; sequencing the template nucleic acid; monitoring the sequencing; and detecting a change in the sequencing that is indicative of the further modification, thereby indentifying the 5-MeC in the template nucleic acid. In some embodiments, the template nucleic acid is a circular nucleic acid, and, optionally, the sequencing comprises rolling-circle synthesis of a nascent nucleic acid strand. Prbe eferably, the template nucleic acid comprises RNA and/or DNA, and in some cases comprises genomic DNA. In certain embodiments, the enzyme is a polymerase enzyme, e.g., which synthesizes a nascent nucleic acid strand during the sequencing reaction, e.g., a single-molecule sequencing reaction. For example, during the monitoring of a single-molecule sequencing reaction, incorporation of single nucleotides into the nascent strand can be monitored to generate a sequence read that is complementary to the template nucleic acid. The aforementioned change preferably occurs at the further modification and/or at one or more positions upstream or downstream of the further modification. Single nucleotides to be used in the incorporation of bases into the nascent strand are preferably differentially labeled to be distinguishable from one another during the monitoring, e.g., via a label linked to a phosphate group that is removed during the processing, e.g., incorporation. In some embodiments, the methods further comprise mapping the 5-MeC within the template nucleic acid. Preferred embodiments of such mapping comprise analyzing a portion of the sequence read that was generated immediately prior to, during, or immediately after the detecting the change in sequencing to determine a sequence complementary to the template nucleic acid; determining the complement of the sequence complementary to the template nucleic acid; and mapping the 5-MeC at a position in the template nucleic acid that is proximal to the complement of the sequence complementary to the template nucleic acid. A change in the sequencing is often a kinetic difference in the processing, e.g., an alteration in the interpulse duration and/or pulse width during the processing. In certain embodiments, the template nucleic acid further comprises a glucose-modified 5-hmC nucleotide, e.g., wherein the method comprises detecting a further change in the sequencing that is indicative of the glucose-modified 5-hmC nucleotide. Detection of the further change is indicative of the glucose-modified 5-hmC nucleotide in the template nucleic acid.

BRIEF DESCRIPTION OF THE DRAWINGS

FIG. 22A presents circos plots for 6-mA and 5-MeC (untreated and treated). FIGS. 22B and 22C show base-resolution IPD ratio views of a section of the genome containing one target site for adenine methylation by dam and one target site for cytosine methylation by dcm. Kinetic score distributions for both on target and off-target sequence motifs before and after mTet1 conversion are plotted in FIG. 22D.

FIG. 23A presents circos plots for 6-mA and 5-MeC (untreated and treated). FIGS. 23B and 23C show base-resolution IPD ratio views of a section of the genome containing two target sites for cytosine methylation. Kinetic score distributions for both on target and off-target sequence motifs before and after mTet1 conversion are plotted in FIG. 23D.

DETAILED DESCRIPTION OF THE INVENTION

I. General

Figure 1:
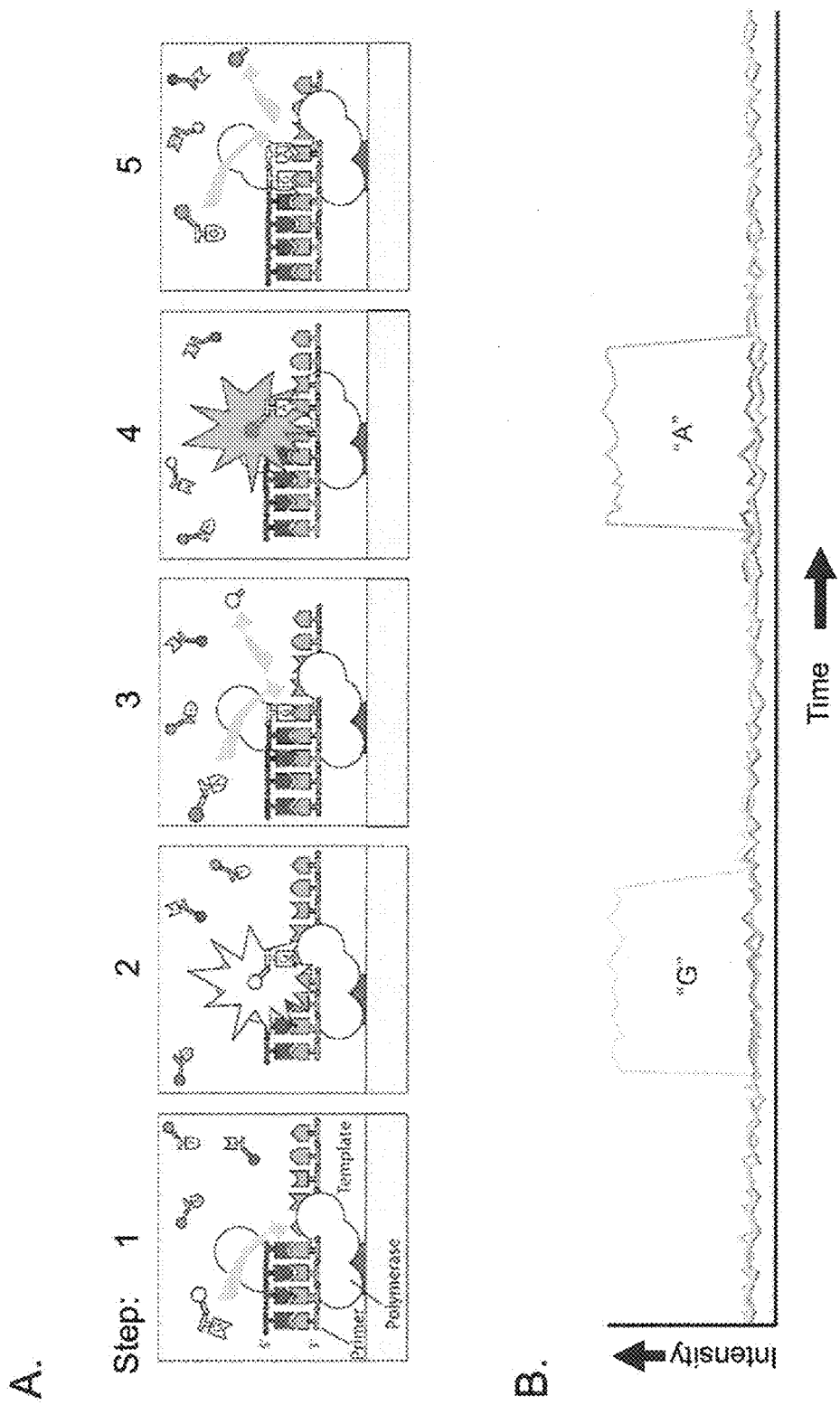
FIGS. 1A and 1B provide an exemplary illustration of single-molecule, real-time (SMRT®) nucleic acid sequencing.

The present invention is generally directed to methods, compositions, and systems for detecting modifications within nucleic acid sequences, and in particularly preferred aspects, methylated nucleotides within sequence templates through the use of single molecule nucleic acid analysis. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

Although certain embodiments of the invention are described in terms of detection of modified nucleotides or other modifications in a single-stranded DNA molecule (e.g., a single-stranded template DNA), various aspects of the invention are applicable to many different types of nucleic acids, including e.g., single- and double-stranded nucleic acids that may comprise DNA (e.g., genomic DNA, mitochondrial DNA, viral DNA, etc.), RNA (e.g., mRNA, siRNA, microRNA, rRNA, tRNA, snRNA, ribozymes, etc.), RNA-DNA hybrids, PNA, LNA, morpholino, and other RNA and/or DNA hybrids, analogs, mimetics, and derivatives thereof, and combinations of any of the foregoing. Nucleic acids for use with the methods, compositions, and systems provided herein may consist entirely of native nucleotides, or may comprise non-natural bases/nucleotides (e.g., synthetic and/or engineered) that may be paired with native nucleotides or may be paired with the same or a different non-natural base/nucleotide. In certain preferred embodiments, the nucleic acid comprises a combination of single-stranded and double-stranded regions, e.g., such as the templates described in U.S. Ser. No. 12/383,855, now U.S. Pat. No. 8,236,499; and Ser. No. 12/413,258, now U.S. Pat. No. 8,153,375, both filed on Mar. 27, 2009 and incorporated herein by reference in their entireties for all purposes. In particular, mRNA modifications are difficult to detect by technologies that require reverse transcriptase PCR amplification because such treatment does not maintain the modification in the amplicons. The present invention provides methods for analyzing modifications in RNA molecules that do not require such amplification. More generally, in certain embodiments, methods are provided that do not require amplification of a modification-containing nucleic acid. In other embodiments, methods are provided for amplification of a modification-containing nucleic acid such that the modifications are maintained in the amplicons.

Generally speaking, the methods of the invention involve monitoring of an analytical reaction to collect "reaction data," wherein the reaction data is indicative of the progress of the reaction. Reaction data includes data collected directly from the reaction, as well as the results of various manipulations of that directly collected data, any or a combination of which can serve as a signal for the presence of a modification in the template nucleic acid. Reaction data gathered during a reaction is analyzed to identify characteristics indicative of the presence of a modification, and typically such data comprises changes or perturbations relative to data generated in the absence of the modification. For example, certain types of reaction data are collected in real time during the course of the reaction, such as metrics related to reaction kinetics, affinity, rate, processivity, signal characteristics, and the like. As used herein, "kinetics," "kinetic signature," "kinetic response," "activity," and "behavior" of an enzyme (or other reaction component, or the reaction as a whole) generally refer to reaction data related to the function/progress of the enzyme (or component or reaction) under investigation and are often used interchangeably herein. Signal characteristics vary depending on the type of analytical reaction being monitored. For example, some reactions use detectable labels to tag one or more reaction components, and signal characteristics for a detectable label include, but are not limited to, the type of signal (e.g., wavelength, charge, etc.) and the shape of the signal (e.g., height, width, curve, etc.). Further, signal characteristics for multiple signals (e.g., temporally adjacent signals) can also be used, including, e.g., the distance between signals during a reaction, the number and/or kinetics of extra signals (e.g., that do not correspond to the progress of the reaction, such as cognate or non-cognate sampling), internal complementarity, and the local signal context (i.e., one or more signal that precede and/or follow a given signal). For example, template-directed sequencing reactions often combine signal data from multiple nucleotide incorporation events to generate a sequence read for a nascent strand synthesized, and this sequence read is used to derive, e.g., by complementarity, the sequence of the template strand. Other types of reaction data are generated from statistical analysis of real time reaction data, including, e.g., accuracy, precision, conformance, etc. In some embodiments, data from a source other than the reaction being monitored is also used. For example, a sequence read generated during a nucleic acid sequencing reaction can be compared to sequence reads generated in replicate experiments, or to known or derived reference sequences from the same or a related biological source. Alternatively or additionally, a portion of a template nucleic acid preparation can be amplified using unmodified nucleotides and subsequently sequenced to provide an experimental reference sequence to be compared to the sequence of the original template in the absence of amplification. Although certain specific embodiments of the use of particular types of reaction data to detect certain kinds of modifications are described at length herein, it is to be understood that the methods, compositions, and systems are not limited to these specific embodiments. Different types of reaction data can be combined to detect various kinds of modifications, and in certain embodiments more than one type of modification can be detected and identified during a single reaction on a single template. Such variations to the detailed embodiments of the invention will be clear to one of ordinary skill based upon the teachings provided herein.

In certain embodiments, redundant sequence information is generated and analyzed to detect one or more modifications in a template nucleic acid. Redundancy can be achieved in various ways, including carrying out multiple sequencing reactions using the same original template, e.g., in an array format, e.g., a ZMW array. In some embodiments in which a lesion is unlikely to occur in all the copies of a given template, reaction data (e.g., sequence reads, kinetics, signal characteristics, signal context, and/or results from further statistical analyses) generated for the multiple reactions can be combined and subjected to statistical analysis to determine a consensus sequence for the template. In this way, the reaction data from a region in a first copy of the template can be supplemented and/or corrected with reaction data from the same region in a second copy of the template. Similarly, a template can be amplified (e.g., via rolling circle amplification) to generate a concatemer comprising multiple copies of the template, and the concatemer can be subjected to sequencing, thereby generating a sequencing read that is internally redundant. As such, the sequence data from a first segment of the concatemer (corresponding to a first region of the template) can be supplemented and/or corrected with sequence data from a second segment of the concatemer also corresponding to the first region of the template. Alternatively or additionally, a template can be subjected to repeated sequencing reactions to generate redundant sequence information that can be analyzed to more thoroughly characterize the modification(s) present in the template. Methods for molecular redundant sequencing are further described in U.S. Pat. No. 7,476,503 and U.S. application Ser. No. 12/383,855 (filed Mar. 27, 2009), now U.S. Pat. No. 8,236,499; Ser. No. 12/413,258 (filed Mar. 27, 2009), now U.S. Pat. No. 8,153,375; Ser. No. 12/413,226 (filed Mar. 27, 2009), now U.S. Pat. No. 8,143,030; and Ser. No. 12/561,221 (filed Sep. 16, 2009), now U.S. Pat. No. 8,383,369, all of which are incorporated herein by reference in their entireties for all purposes.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36):65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem. Soc. 127(5):1424-30; Johnson, et al. (2004) 32(6):1937-41; Kimoto, et al. (2007) Nucleic Acids Res. 35(16):5360-9; Able, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural (e.g., non-standard, synthetic, etc.) base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C—Ag(I)—C, and metallo-homo-basepairs of 2,6-bis(ethylthiomethyl)pyridine nucleobases Spy, 6-amino-5-nitro-3-(1'13-D-2'-deoxyribofuranosyl)-2(1H)-pyridone (dZ), 2-amino-8-(1'-β-D-2'-deoxyribofuranosyl)-imidazo[1,2-a]-1,3,5-triazin-4 (8H)-one (dP), and alkyne-, enamine-, alcohol-, imidazole-, guanidine-, and pyridyl-substitutions to the purine or pyridimine base (Wettig, et al. (2003) J Inorg Biochem 94:94-99; Clever, et al, (2005) Angew Chem Int Ed 117:7370-7374; Schlegel, et al. (2009) Org Biomol Chem 7(3):476-82; Zimmerman, et al. (2004) Bioorg Chem 32(1):13-25; Yanagida, et al. (2007) Nucleic Acids Symp Ser (Oxf) 51:179-80; Zimmerman (2002) J. Am. Chem Soc 124(46):13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; Yang, et al. (2007) Nucleic Acids Res. 35(13):4238-4249; Yang, et al. (2006) Nucleic Acids Res. 34(20:6095-6101; Geyer, et al. (2003) Structure 11: 1485-1498; and Seo, et al. (2009) J Am Chem Soc 131:3246-3252, all incorporated herein by reference in their entireties for all purposes). Other types of modifications include, e.g., a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In certain aspects, methods, compositions, and systems for detection and/or reversal of modifications in a template for single-molecule sequencing are provided, as well as determination of their location (i.e. "mapping") within a nucleic acid molecule. In certain preferred embodiments, high-throughput, real-time, single-molecule, template-directed sequencing assays are used to detect the presence of such modified sites and to determine their location on the DNA template, e.g., by monitoring the progress and/or kinetics of a polymerase enzyme processing the template. For example, when a polymerase enzyme encounters certain types of damage or other modifications in a DNA template, the progress of the polymerase can be temporarily or permanently blocked, e.g., resulting in a paused or dissociated polymerase. As such, the detection of a pause in or termination of nascent strand synthesis is indicative of the presence of such damage or lesion. Similarly, certain types of modifications cause other perturbations in the activity of the polymerase, such as changes in the kinetics of nascent strand synthesis, e.g., changes in pulse width or interpulse duration. Yet further, some modifications cause changes in the enzyme activity that are detectable as changes in the error metrics of the enzyme during template-directed polymerization. By analysis of the sequence reads produced prior to the change or perturbation in activity of the polymerase, and alternatively or additionally after reinitiation of synthesis, one can map the site of the damage or lesion on the template. Since different types of lesions can have different effects on the progress of the polymerase on the substrate, in certain cases the behavior of the polymerase on the template not only informs as to where the lesion occurs, but also what type of lesion is present. These and other aspects of the invention are described in greater detail in the description and examples that follow.

Additional teachings that can be used with the or otherwise complement the teachings herein with respect to analysis of modifications in nucleic acid molecules are provided in PCT Application Publication No. WO 2012/065043, incorporated herein by reference in its entirety for all purposes.

II. Single Molecule Sequencing

In certain aspects of the invention, single molecule real time sequencing systems are applied to the detection of modified nucleic acid templates through analysis of the sequence and/or kinetic data derived from such systems. In particular, modifications in a template nucleic acid strand alter the enzymatic activity of a nucleic acid polymerase in various ways, e.g., by increasing the time for a bound nucleobase to be incorporated and/or increasing the time between incorporation events. In certain embodiments, polymerase activity is detected using a single molecule nucleic acid sequencing technology. In certain embodiments, polymerase activity is detected using a nucleic acid sequencing technology that detects incorporation of nucleotides into a nascent strand in real time. In preferred embodiments, a single molecule nucleic acid sequencing technology is capable of real-time detection of nucleotide incorporation events. Such sequencing technologies are known in the art and include, e.g., the SMRT® sequencing and nanopore sequencing technologies. For more information on nanopore sequencing, see, e.g., U.S. Pat. No. 5,795,782; Kasianowicz, et al. (1996) Proc Natl Acad Sci USA 93(24):13770-3; Ashkenas, et al. (2005) Angew Chem Int Ed Engl 44(9):1401-4; Howorka, et al. (2001) Nat Biotechnology 19(7):636-9; and Astier, et al. (2006) J Am Chem Soc 128(5):1705-10, all of which are incorporated herein by reference in their entireties for all purposes. With regards to nucleic acid sequencing, the term "template" refers to a nucleic acid molecule subjected to template-directed synthesis of a nascent strand. A template may comprise, e.g., DNA, RNA, or analogs, mimetics, derivatives, or combinations thereof, as described elsewhere herein. Further, a template may be single-stranded, double-stranded, or may comprise both single- and double-stranded regions. A modification in a double-stranded template may be in the strand complementary to the newly synthesized nascent strand, or may by in the strand identical to the newly synthesized strand, i.e., the strand that is displaced by the polymerase.

The preferred direct methylation sequencing described herein may generally be carried out using single molecule real time sequencing systems, i.e., that illuminate and observe individual reaction complexes continuously over time, such as those developed for SMRT® DNA sequencing (see, e.g., P. M. Lundquist, et al., *Optics Letters* 2008, 33, 1026, which is incorporated herein by reference in its entirety for all purposes). The foregoing SMRT® sequencing instrument generally detects fluorescence signals from an array of thousands of ZMWs simultaneously, resulting in highly parallel operation. Each ZMW, separated from others by distances of a few micrometers, represents an isolated sequencing chamber.

Detection of single molecules or molecular complexes in real time, e.g., during the course of an analytical reaction, generally involves direct or indirect disposal of the analytical reaction such that each molecule or molecular complex to be detected is individually resolvable. In this way, each analytical reaction can be monitored individually, even where multiple such reactions are immobilized on a single substrate. Individually resolvable configurations of analytical reactions can be accomplished through a number of mechanisms, and typically involve immobilization of at least one component of a reaction at a reaction site. Various methods of providing such individually resolvable configurations are known in the art, e.g., see European Patent No. 1105529 to Balasubramanian, et al.; and Published International Patent Application No. WO 2007/041394, the full disclosures of which are incorporated herein by reference in their entireties for all purposes. A reaction site on a substrate is generally a location on the substrate at which a single analytical reaction is performed and monitored, preferably in real time. A reaction site may be on a planar surface of the substrate, or may be in an aperture in the surface of the substrate, e.g., a well, nanohole, or other aperture. In preferred embodiments, such apertures are "nanoholes," which are nanometer-scale holes or wells that provide structural confinement of analytic materials of interest within a nanometer-scale diameter, e.g., ~1-300 nm. In some embodiments, such apertures comprise optical confinement characteristics, such as zero-mode waveguides, which are also nanometer-scale apertures and are further described elsewhere herein. Typically, the observation volume (i.e., the volume within which detection of the reaction takes place) of such an aperture is at the attoliter ($10^{-18}$ L) to zeptoliter ($10^{-21}$ L) scale, a volume suitable for detection and analysis of single molecules and single molecular complexes.

The immobilization of a component of an analytical reaction can be engineered in various ways. For example, an enzyme (e.g., polymerase, reverse transcriptase, kinase, etc.) may be attached to the substrate at a reaction site, e.g., within an optical confinement or other nanometer-scale aperture. In other embodiments, a substrate in an analytical reaction (for example, a nucleic acid template, e.g., DNA, RNA, or hybrids, analogs, derivatives, and mimetics thereof, or a target molecule for a kinase) may be attached to the substrate at a reaction site. Certain embodiments of template immobilization are provided, e.g., in U.S. patent application Ser. No. 12/562,690, filed Sep. 18, 2009, now U.S. Pat. No. 8,481,264, and incorporated herein by reference in its entirety for all purposes. One skilled in the art will appreciate that there are many ways of immobilizing nucleic acids and proteins into an optical confinement, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

In some embodiments, a nucleic acid template is immobilized onto a reaction site (e.g., within an optical confinement) by attaching a primer comprising a complementary region at the reaction site that is capable of hybridizing with the template, thereby immobilizing it in a position suitable for monitoring. In certain embodiments, an enzyme complex is assembled in an optical confinement, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of an optical confinement of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

In some embodiments, a substrate comprising an array of reaction sites is used to monitor multiple biological reactions, each taking place at a single one of the reaction sites. Various means of loading multiple biological reactions onto an arrayed substrate are known to those of ordinary skill in the art and are described further, e.g., in U.S. Ser. No. 61/072,641, incorporated herein by reference in its entirety for all purposes. For example, basic approaches include: creating a single binding site for a reaction component at the reaction site; removing excess binding sites at the reaction site via catalytic or secondary binding methods; adjusting the size or charge of the reaction component to be immobilized; packaging or binding the reaction component within (or on) a particle (e.g., within a viral capsid), where a single such particle fits into the relevant reaction site (due to size or charge of the particle and/or observation volume); using non-diffusion limited loading; controllably loading the reaction component (e.g., using microfluidic or optical or electrical control); sizing or selecting charges in the reaction sites/observation volumes (e.g., the sizes of optical confinements in an array) to control which reaction components will fit (spatially or electrostatically) into which reaction sites/observation volumes; iterative loading of reaction components, e.g., by masking active sites between loading cycles; enriching the activity of the reaction components that are loaded; using self-assembling nucleic acids to sterically control loading; adjusting the size of the reaction site/observation volume; and many others. Such methods and compositions provide for the possibility of completely loading single-molecule array reaction sites (instead of about 30% of such sites as occurs in "Poisson limited" loading methods) with single reaction components (e.g., molecular complexes).

In preferred aspects, the methods, compositions, and systems provided herein utilize optical confinements to facilitate single molecule resolution of analytical reactions. In preferred embodiments, such optical confinements are configured to provide tight optical confinement so only a small volume of the reaction mixture is observable. Some such optical confinements and methods of manufacture and use thereof are described at length in, e.g., U.S. Pat. Nos. 7,302,146. 7,476,503, 7,313,308, 7,315,019, 7,170,050, 6,917,726, 7,013,054, 7,181,122, and 7,292,742; U.S. Patent Publication Nos. 20080128627, 20080152281, and 200801552280; and U.S. Ser. No. 11/981,740, now abandoned; and Ser. No. 12/560,308, now U.S. Pat. No. 8,471,230, all of which are incorporated herein by reference in their entireties for all purposes.

Where reaction sites are located in optical confinements, the optical confinements can be further tailored in various ways for optimal confinement of an analytical reaction of interest. In particular, the size, shape, and composition of the optical confinement can be specifically designed for containment of a given enzyme complex and for the particular label and illumination scheme used.

In certain preferred embodiments of the invention, single-molecule real-time sequencing systems already developed are applied to the detection of modified nucleic acid templates through analysis of the sequence and kinetic data derived from such systems. As described below, methylated cytosine and other modifications in a template nucleic acid will alter the enzymatic activity of a polymerase processing the template nucleic acid. In certain embodiments, polymerase kinetics in addition to sequence read data are detected using a single molecule nucleic acid sequencing technology, e.g., the SMRT® sequencing technology developed by Pacific Biosciences (Eid, J. et al. (2009) *Science* 2009, 323, 133, the disclosure of which is incorporated herein by reference in its entirety for all purposes). This technique is capable of long sequencing reads and provides high-throughput methylation profiling even in highly repetitive genomic regions, facilitating de novo sequencing of modifications such as methylated bases. SMRT® sequencing systems typically utilize state-of-the-art single-molecule detection instruments, production-line nanofabrication chip manufacturing, organic chemistry, protein mutagenesis, selection and production facilities, and software and data analysis infrastructures.

Certain preferred methods of the invention employ real-time sequencing of single DNA molecules (Eid, et al., supra), with intrinsic sequencing rates of several bases per second and average read lengths in the kilobase range. In such sequencing, sequential base additions catalyzed by DNA polymerase into the growing complementary nucleic acid strand are detected with fluorescently labeled nucleotides. The kinetics of base additions and polymerase translocation are sensitive to the structure of the DNA double-helix, which is impacted by the presence of base modifications, e.g, 5-MeC, 5-hmC, base J, etc., and other perturbations (secondary structure, bound agents, etc.) in the template. By monitoring the activity of DNA polymerase during sequencing, sequence read information and base modifications can be simultaneously detected. Long, continuous sequence reads that are readily achievable using SMRT® sequencing facilitate modification (e.g., methylation) profiling in low complexity regions that are inaccessible to some technologies, such as certain short-read sequencing technologies. Carried out in a highly parallel manner, methylomes can be sequenced directly, with single base-pair resolution and high throughput.

The principle of SMRT® sequencing is illustrated in FIG. 1. Two important technology components of certain embodiments of this process are: (i) optical confinement technology that allows single-molecule detection at concentrations of labeled nucleotides relevant to the enzyme, and (ii) phospholinked nucleotides that enable observation of uninterrupted polymerization.

In preferred embodiments, optical confinements are ZMW nanostructures, preferably in an arrayed format. Typically, ZMWs arrays comprise dense arrays of holes, ~100 nm in diameter, fabricated in a ~100 nm thick metal film deposited on a transparent substrate (e.g., silicon dioxide). These structures are further described in the art, e.g., in M. J. Levene, et al., *Science* 2003, 299, 682; and M. Foquet, et al., *J. Appl. Phys.* 2008, 103, 034301, the disclosures of which are incorporated herein by reference in their entireties for all purposes. Each ZMW becomes a nanophotonic visualization chamber for recording an individual polymerization reaction, providing a detection volume of just 100 zeptoliters ($10^{-21}$ liters). This volume represents a ~1000-fold improvement over diffraction-limited confocal microscopy, facilitating observation of single incorporation events against the background created by the relatively high concentration of fluorescently labeled nucleotides. Polyphosphonate and silane-based surface coatings mediate enzyme immobilization to the transparent floor of the ZMW while blocking non-specific attachments to the metal top and side wall surfaces (Eid, et al., supra; and J. Korlach, et al., *Proc Natl Acad Sci USA* 2008, 105, 1176, the disclosures of which are incorporated herein by reference in their entireties for all purposes). While certain methods described herein involve the use of ZMW confinements, it will be readily understood by those of ordinary skill in the art upon review of the teachings herein that these methods may also be practiced using other reaction formats, e.g., on planar substrates or in nanometer-scale apertures other than zero-mode waveguides. (See, e.g., U.S. Ser. No. 12/560,308, filed Sep. 15, 2009; and U.S. Patent Publication No. 20080128627, incorporated herein supra.)

The second important component is phospholinked nucleotides for which a detectable label (e.g., comprising a fluorescent dye) is attached to the terminal phosphate rather than the base (FIG. 1). (See, e.g., J. Korlach, et al., *Nucleos. Nucleot. Nucleic Acids* 2008, 27, 1072, which is incorporated herein by reference in its entirety for all purposes.) 100% replacement of unmodified nucleotides by phospholinked nucleotides is performed, and the enzyme cleaves away the label as part of the incorporation process, leaving behind a completely natural, double-stranded nucleic acid product. Each of the four different nucleobases is labeled with a distinct detectable label to discriminate base identities during incorporation events, thus enabling sequence determination of the complementary DNA template. During incorporation, the enzyme holds the labeled nucleotide in the ZMW's detection volume for tens of milliseconds, orders of magnitude longer than the average diffusing nucleotide is present. Signal (e.g., fluorescence) is emitted continuously from the detectable label during the duration of incorporation, causing a detectable pulse of increased fluorescence in the corresponding color channel. The pulse is terminated naturally by the polymerase releasing the pyrophosphate-linker-label group. Preferably, the removal of the linker and label during incorporation is complete such that the nucleotide incorporated has no remnants of the linker or label remaining. The polymerase then translocates to the next base, and the process repeats.

As shown in FIG. 1A, single DNA polymerase molecules with bound DNA template are attached to a substrate, e.g., at the bottom of each zero-mode waveguide. Polymerization of the complementary DNA strand is observed in real time by detecting fluorescently labeled nucleotides. Reactions steps involved in SMRT® sequencing are as follows: Step 1: The DNA template/primer/polymerase complex is surrounded by diffusing fluorescently labeled nucleotides which probe the active site. Step 2: A labeled nucleotide makes a cognate binding interaction with the next base in the DNA template that lasts for tens of milliseconds, during which fluorescence is emitted continuously. Step 3: The polymerase incorporates the nucleotide into the growing nucleic acid chain, thereby cleaving the α-β phosphodiester bond, followed by release of the nucleotide. Steps 4-5: The process repeats. A prophetic trace is shown in FIG. 1B that comprises each step shown in 1A. At steps 2 and 4, a fluorescent signal is emitted during binding and incorporation of a nucleotide into the growing nucleic acid chain, and monitoring of these fluorescent signals provides a sequence of nucleotide incorporations that can be used to derive the sequence of the template nucleic acid. For example, a 5'-G-A-3' sequence in the growing chain indicates a 5'-T-C-3' sequence in the complementary template strand.

Figure 2:
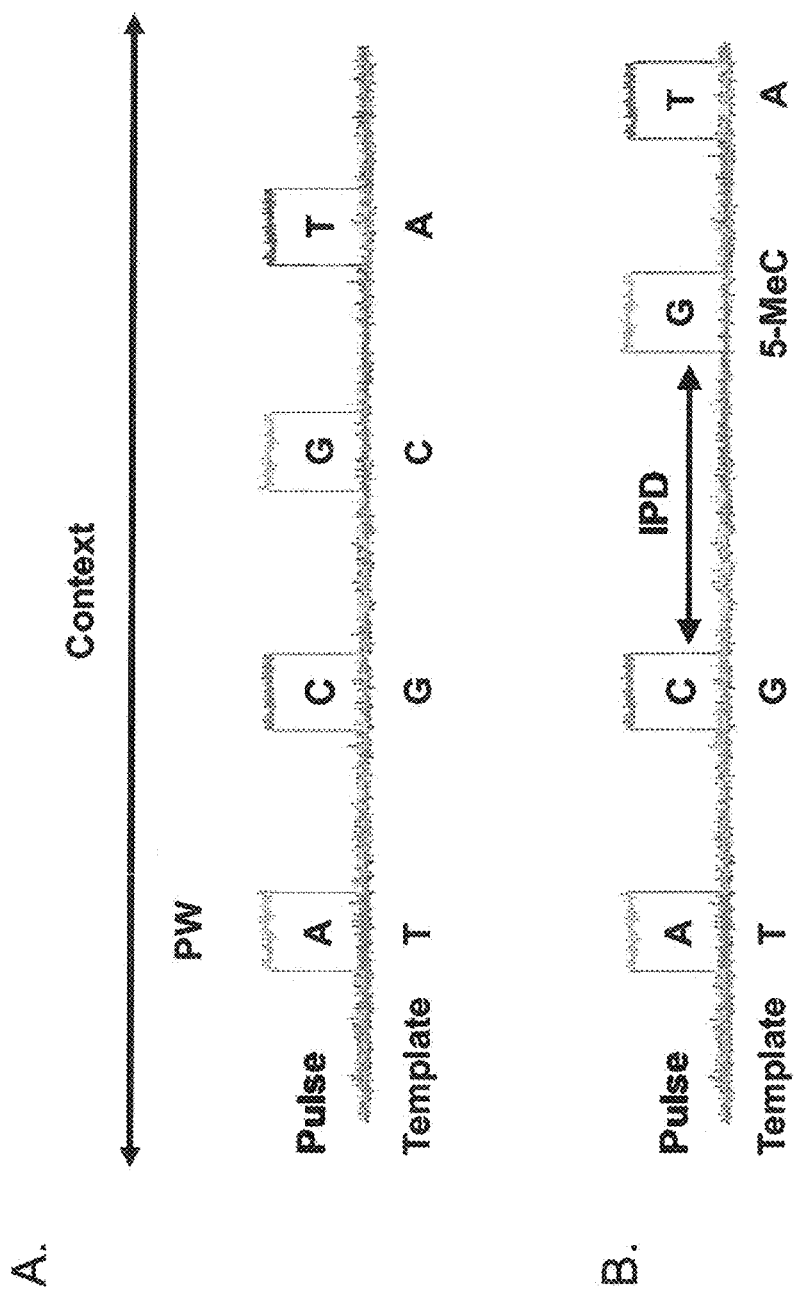
FIGS. 2A and 2B provide illustrative examples of various types of reaction data in the context of a pulse trace.

As described above, reaction data is indicative of the progress of a reaction and can serve as a signal for the presence of a modification in the template nucleic acid. Reaction data in single molecule sequencing reaction reactions using fluorescently labeled bases is generally centered around characterization of detected fluorescence pulses, a series of successive pulses ("pulse trace" or one or more portions thereof), and other downstream statistical analyses of the pulse and trace data. Fluorescence pulses are characterized not only by their spectrum, but also by other metrics including their duration, shape, intensity, and by the interval between successive pulses (see, e.g., Eid, et al., supra; and U.S. Patent Publication No. 20090024331, incorporated herein by reference in its entirety for all purposes). While not all of these metrics are generally required for sequence determination, they add valuable information about the processing of a template, e.g., the kinetics of nucleotide incorporation and DNA polymerase processivity and other aspects of the reaction. Further, the context in which a pulse is detected (i.e., the one or more pulses that precede and/or follow the pulse) can contribute to the identification of the pulse. For example, the presence of certain modifications alters not only the processing of the template at the site of the modification, but also the processing of the template upstream and/or downstream of the modification. For example, the presence of modified bases in a template nucleic acid has been shown to change the width of a pulse and/or the interpulse duration (IPD), at the modified base and/or at one or more positions proximal to it. A change in pulse width may or may not be accompanied by a change in IPD, e.g., the length of time between the fluorescent pulses that indicate nucleotide incorporation. IPD metrics vary between a modified template and a control (e.g., unmodified) template, and are influenced by the type of modification and sequence context around the modification. In addition, the types of nucleotides or nucleotide analogs being incorporated into a nascent strand can also affect the sensitivity and response of a polymerase to a modification. For example, certain nucleotide analogs increase the sensitivity and/or response of the enzyme as compared to that in the presence of native nucleotides or different nucleotide analogs, thereby facilitating detection of a modification. In particular, nucleotide analogs comprising different types of linkers and/or fluorescent dyes have been shown to have different effects on polymerase activity, and can impact the incorporation of a base into a nascent strand opposite a modification, and/or can impact the incorporation kinetics for a polynucleotide region proximal to (e.g., upstream or downstream of) the modification. The region proximal to the modification can, in certain embodiments, correspond to the region of the template complementary to the portion of the nascent strand synthesized while the footprint of the polymerase overlapped the locus of the modification. These analog-based differences in polymerase sensitivity and response can be used in redundant sequencing strategies to further enhance the detection of modifications. For example, exchanging nucleotide analogs between iterations of an iterative sequencing reaction elicits changes in polymerase activity between the iterations. Statistical analysis of the differences in the sequencing reads from each iteration combined with the knowledge of how each type of nucleotide analog affects polymerase activity can facilitate identification of modifications present in the reaction. FIG. 2 provides illustrative examples of various types of reaction data in the context of a pulse trace including IPD, pulse width (PW), pulse height (PH), and context. FIG. 2A illustrates these reaction data on a pulse trace generated on an unmodified template, and FIG. 2B illustrates how the presence of a modification (5-MeC) can elicit a change in one of these reaction data (IPD) to generate a signal (increased IPD) indicative of the presence of the modification.

In yet further embodiments, reaction data is generated by analysis of the pulse and trace data to determine error metrics for the reaction. Such error metrics include not only raw error rate, but also more specific error metrics, e.g., identification of pulses that did not correspond to an incorporation event (e.g., due to "sampling"), incorporations that were not accompanied by a detected pulse, incorrect incorporation events, and the like. Any of these error metrics, or combinations thereof, can serve as a signal indicative of the presence of one or more modifications in the template nucleic acid. In some embodiments, such analysis involves comparison to a reference sequence and/or comparison to replicate sequence information from the same or an identical template, e.g., using a standard or modified multiple sequence alignment. Certain types of modifications cause an increase in one or more error metrics. For example, some modifications can be "paired" with more than one type of incoming nucleotide or analog thereof; so replicate sequence reads for the region comprising the modification will show variable base incorporation opposite such a modification. Such variable incorporation is thereby indicative of the presence of the modification. Certain types of modifications cause an increase in one or more error metrics proximal to the modification, e.g., immediately upstream or downstream. The error metrics at a locus or within a region of a template are generally indicative of the type of modification(s) present at that locus or in that region of the template, and therefore serve as a signal of such modification(s). In preferred embodiments, at least some reaction data is collected in real time during the course of the reaction, e.g., pulse and/or trace characteristics.

Although described herein primarily with regards to fluorescently labeled nucleotides, other types of detectable labels and labeling systems can also be used with the methods, compositions, and systems described herein including, e.g.; quantum dots, surface enhanced Raman scattering particles, scattering metallic nanoparticles, FRET systems, intrinsic fluorescence, non-fluorescent chromophores, and the like. Such labels are generally known in the art and are further described in Provisional U.S. Patent Application No. 61/186, 661, filed Jun. 12, 2009; U.S. Pat. Nos. 6,399,335, 5,866,366, 7,476,503, and 4,981,977; U.S. Patent Pub. No. 2003/ 0124576; U.S. Ser. No. 61/164,567; WO 01/16375; Mujumdar, et al Bioconjugate Chem. 4(2):105-111, 1993; Ernst, et al, Cytometry 10:3-10, 1989; Mujumdar, et al, Cytometry 10:1119, 1989; Southwick, et al, Cytometry 11:418-430, 1990; Hung, et al, Anal. Biochem. 243(1):15-27, 1996; Nucleic Acids Res. 20(10:2803-2812, 1992; and Mujumdar, et al, Bioconjugate Chem. 7:356-362, 1996; Intrinsic Fluorescence of Proteins, vol. 6, publisher: Springer US, ©2001; Kronman, M. J. and Holmes, L. G. (2008) Photochem and Photobio 14(2): 113-134; Yanushevich, Y. G., et al. (2003) Russian J. Bioorganic Chem 29(4) 325-329; and Ray, K., et al. (2008) J. Phys. Chem. C 112(46): 17957-17963, all of which are incorporated herein by reference in their entireties for all purposes. Many such labeling groups are commercially available, e.g., from the Amersham Biosciences division of GE Healthcare, and Molecular Probes/Invitrogen Inc. (Carlsbad, Calif.)., and are described in 'The Handbook—A Guide to Fluorescent Probes and Labeling Technologies, Tenth Edition' (2005) (available from Invitrogen, Inc./Molecular Probes and incorporated herein in its entirety for all purposes). Further, a combination of the labeling strategies described herein and known in the art for labeling reaction components can be used.

Various strategies, methods, compositions, and systems are provided herein for detecting modifications in a nucleic acid, e.g., during real-time nascent strand synthesis. For example, since DNA polymerases can typically bypass 5-MeC in a template nucleic acid and properly incorporate a guanine in the complementary strand opposite the 5-MeC, additional strategies are desired to detect such altered nucleotides in the template. Various such strategies are provided herein, such as, e.g., a) modification of the polymerase to introduce an specific interaction with the modified nucleotide; b) detecting variations in enzyme kinetics, e.g., pausing, retention time, etc.; c) use of a detectable and optionally modified nucleotide analog that specifically base-pairs with the modification and is potentially incorporated into the nascent strand; d) chemical treatment of the template prior to sequencing that specifically alters 5-MeC sites in the template; e) use of a protein that specifically binds to the modification in the template nucleic acid, e.g., delaying or blocking progression of a polymerase during replication; and f) use of sequence context (e.g., the higher frequency of 5-MeC nucleotides in CpG islands) to focus modification detection efforts on regions of the template that are more likely to contain such a modification (e.g., GC-rich regions for 5-MeC detection). These strategies may be used alone or in combination to detect 5-MeC sites in a template nucleic acid during nascent strand synthesis.

III. Polymerase Modifications

Various different polymerases may be used in template-directed sequence reactions, e.g., those described at length, e.g., in U.S. Pat. No. 7,476,503, the disclosure of which is incorporated herein by reference in its entirety for all purposes. In brief, the polymerase enzymes suitable for the present invention can be any nucleic acid polymerases that are capable of catalyzing template-directed polymerization with reasonable synthesis fidelity. The polymerases can be DNA polymerases or RNA polymerases (including, e.g., reverse transcriptases), DNA-dependent or RNA-dependent polymerases, thermostable polymerases or thermally degradable polymerases, and wildtype or modified polymerases. In some embodiments, the polymerases exhibit enhanced efficiency as compared to the wildtype enzymes for incorporating unconventional or modified nucleotides, e.g., nucleotides linked with fluorophores. In certain preferred embodiments, the methods are carried out with polymerases exhibiting a high degree of processivity, i.e., the ability to synthesize long stretches (e.g., over about 10 kilobases) of nucleic acid by maintaining a stable nucleic acid/enzyme complex. In certain preferred embodiments, sequencing is performed with polymerases capable of rolling circle replication. A preferred rolling circle polymerase exhibits strand-displacement activity, and as such, a single circular template can be sequenced repeatedly to produce a sequence read comprising multiple copies of the complement of the template strand by displacing the nascent strand ahead of the translocating polymerase. Since the methods of the invention can increase processivity of the polymerase by removing lesions that block continued polymerization, they are particularly useful for applications in which a long nascent strand is desired, e.g. as in the case of rolling-circle replication. Non-limiting examples of rolling circle polymerases suitable for the present invention include but are not limited to T5 DNA polymerase, T4 DNA polymerase holoenzyme, phage M2 DNA polymerase, phage PRD1 DNA polymerase, Klenow fragment of DNA polymerase, and certain polymerases that are modified or unmodified and chosen or derived from the phages Φ29 (Phi29), PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. In certain preferred embodiments, the polymerase is a modified Phi29 DNA polymerase, e.g., as described in U.S. Patent Publication No. 20080108082, incorporated herein by reference in its entirety for all purposes. Additional polymerases are provided, e.g., in U.S. Ser. No. 11/645,125, filed Dec. 21, 2006; Ser. No. 11/645,135, filed Dec. 21, 2006, now abandoned; Ser. No. 12/384,112, filed Mar. 30, 2009, now U.S. Pat. No. 8,257,954; and 61/094,843, filed Sep. 5, 2008; as well as in U.S. Patent Publication No. 20070196846, the disclosures of which are incorporated herein by reference in their entireties for all purposes.

VI. Chemical Modification of Template

Direct detection of modifications (e.g., methylated bases as described above) without pre-treatment of the DNA sample, has many benefits. Alternatively or additionally, complementary techniques may be employed, such as the use of non-natural or modified nucleotide analogs and/or base pairing described elsewhere herein. In general, such complementary techniques serve to enhance the detection of the modification, e.g., by amplifying a signal indicative of the modification. Further, while the methods described herein focus primarily on detection of 5-MeC nucleotides, it will be clear to those of ordinary skill in the art that these methods can also be extended to detection of other types of nucleotide modifications or damage. In addition, since certain sequencing technologies (e.g., SMRT® sequencing) do not require amplification of the template, e.g., by PCR, other chemical modifications of the 5-MeC or other modifications can be employed to facilitate detection of these modified nucleotides in the template, e.g., by employing modifying agents that introduce additional modifications into the template at or proximal to the modified nucleotides. For example, the difference in redox potential between normal cytosine and 5-MeC can be used to selectively oxidize 5-MeC and further distinguish it from the nonmethylated base. Such methods are further described elsewhere, and include halogen modification (S. Bareyt, et al., *Angew Chem Int Ed Engl* 2008, 47(1), 181) and selective osmium oxidation (A. Okamoto, *Nucleosides Nucleotides Nucleic Acids* 2007, 26(10-12), 1601; and K. Tanaka, et al., *J Am Chem Soc* 2007, 129(17), 5612), and these references are incorporated herein by reference in their entireties for all purposes.

Bisulfite Modification

As described elsewhere herein, methylcytosine has an effect on IPD over a In certain embodiments, the template may be modified by treatment with bisulfite. Bisulfite sequencing is a common method for analyzing CpG methylation patterns in DNA. Bisulfite treatment deaminates unmethylated cytosine in a single-stranded nucleic acid to form uracil (P. W. Laird, *Nat Rev Cancer* 2003, 3(4), 253; and H. Hayatsu, *Mutation Research* 2008, 659, 77, incorporated herein by reference in their entireties for all purposes). In contrast, the modified 5-MeC base is resistant to treatment with bisulfite. As such, pretreatment of template DNA with bisulfite will convert cytosines to uracils, and subsequent sequencing reads will contain guanine incorporations opposite 5-MeC nucleotides in the template and adenine incorporations opposite the uracil (previously unmethylated cytosine) nucleotides. If a nucleic acid to be treated with bisulfite is double-stranded, it is denatured prior to treatment. In conventional methods, amplification, e.g., PCR, typically precedes sequencing, which amplifies the modified nucleic acid, but does not preserve information about the complementary strand. In contrast, certain embodiments of the present invention include use of a template molecule comprising both strands of a double-stranded nucleic acid that can be converted to a single-stranded molecule, e.g., by adjusting pH, temperature, etc. Treatment of the single-stranded molecule with bisulfite is followed by single-molecule sequencing, and because the template retains both strands of the original nucleic acid, sequence information from both is generated. Comparison of the resulting sequence reads for each strand of the double-stranded nucleic acid will identify positions at which an unmethylated cytosine was converted to uracil in the original templates since the reads from the two templates will be non-complementary at that position (A-C mismatch). Likewise, reads from the two templates will be complementary at a cytosine position (G-C match) where the cytosine position was methylated in the original template. In certain preferred embodiments, a circular template is used, preferably having regions of internal complementarity that can hybridize to form a double-stranded region, e.g., as described in U.S. Ser. No. 12/383,855, now U.S. Pat. No. 8,236,499; and U.S. Ser. No. 12/413,258, now U.S. Pat. No. 8,153,375; both filed on Mar. 27, 2009, and both incorporated herein by reference in their entireties for all purposes.

As described elsewhere herein, methylcytosine has an effect on IPD over a number of neighboring positions when compared to non-methylated cytosine. Uracil compared to thymine is like unmethylated cytosine compared to methylcytosine (i.e. the only difference between U and T is that T has an additional methyl group). Thus, the invention provides methods for performing bisulfite sequencing in which the polymerase kinetics (e.g., IPD and pulse width) or the mismatch incorporation rate are monitored in addition to the actual nucleotides being incorporated. Detection of a change in either of these kinetic parameters or in the mismatch rate at the position in question, or at neighboring positions, is used to determine whether or not a position was always a T or is a U that was originally an unmethylated cytosine.

In certain embodiments, polymerase mutants are designed that are more sensitive to the difference between thymine and uracil in order to enhance the effect described above. Methods for designing polymerase variants are described in detail above and need not be repeated here.

Additionally or alternatively, PCR of uracil-containing oligonucleotides is not necessarily as efficient as PCR without uracil. This issue can bias the PCR amplification of bisulfite-converted DNA. Certain methods of sequencing-by-synthesis using bisulfite-modified templates described herein circumvent this problem by not using PCR amplification. However, the kinetics of these sequencing-by-synthesis reactions can be monitored to detect changes in kinetics due to the presence of uracil residues.

Further, the methods presented herein are useful for detecting PCR bias in the amplification of bisulfite-treated nucleic acids. For example, a few rounds of PCR can be performed on various oligos, some with uracil and some without (including controls with the same sequence but containing thymine in place of uracil). After performing sequencing-by-synthesis on all the resulting oligos, one could determine the percentage of oligos that still contain uracil. If it's different than the expected percentage given ideal (unbiased) PCR amplification, then a bias has been detected.

In yet further embodiments, a template nucleic acid is exposed to a reagent that transforms a modified nucleotide to a different nucleotide structure. For example, a bacterial cytosine methyl transferase converts 5-MeC to thymine (M. J. Yebra, et al., *Biochemistry* 1995, 34(45), 14752, incorporated herein by reference in its entirety for all purposes). Alternatively, the reagent may convert a methyl-cytosine to 5-hydroxy-methylcytosine, e.g., the hydroxylase enzyme TET1 (M. Tahiliani, et al., *Science* 2009, 324(5929), 930, incorporated herein by reference in its entirety for all purposes). In further embodiments, the reagent may include a cytidine deaminase that converts methyl-cytosine to thymine (H. D. Morgan, et al., *J Biological Chem* 2004, 279, 52353, incorporated herein by reference in its entirety for all purposes). In yet further embodiments, a restriction enzyme that specifically alters a modification of interest can be used to create a lesion at the modification site. For example, DPNI cleaves at a recognition site comprising methyladenosine. Optionally, the cleaved template could be repaired during an analytical reaction by inclusion of a ligase enzyme in the reaction mixture. As noted elsewhere herein, nucleotides other than 5-MeC can also be modified and detected by the methods provided herein. For example, adenine can be converted to inosine through deamination, and this conversion affected by methylation of adenine, allowing differential treatment and detection of adenine and MeA.

Another modified base that can be detected using the methods provided herein is 5-hydroxymethylcytosine (5-hmC). It was recently found to be abundant in human and mouse brains, as well as in embryonic stem cells (see, e.g., Kriaucionis, et al. (2009) "The nuclear DNA base 5-hydroxymethylcytosine is present in Purkinje neurons and the brain" *Science* 324 (5929): 929-30; Tahiliani M et al. (May 2009) "Conversion of 5-methylcytosine to 5-hydroxymethylcytosine in mammalian DNA by MLL partner TET1" *Science* 324 (5929): 930-35; and WO/2010/037001, incorporated herein by reference in their entireties for all purposes). In mammals, it can be generated by oxidation of 5-methylcytosine, a reaction mediated by the Tet family of enzymes. Conventional bisulfite sequencing does not effectively distinguish 5-hmC from 5-MeC because 5-hmC tends to remain unmodified like 5-MeC. As such, mass spectrometry is the typical means of detecting 5-hmC in a nucleic acid sample. The methods described herein provide a high-throughput, real-time method to distinguish between C, 5-MeC, and 5-hmC by monitoring deviations from normal polymerase kinetics, including IPD and pulse width.

In certain embodiments, bisulfite conversion can be used in methods for distinguishing 5-MeC from 5-hydroxymethylcytosine (5-hmC). As noted above, bisulfite conversion changes cytosine into uracil and does not change 5-MeC. Bisulfite conversion also changes hydroxymethyl-cytosine (5-hmC) to cytosine-5-methylenesulfonate (CMS), which contains a bulky $SO_3$ adduct in place of the OH adduct of 5-hmC. Like methyl-cytosine, CMS base-pairs with guanine. As such, simply knowing the identity of the base (G) incorporated at a position complementary to a modified base does not alone distinguish between a 5-MeC modified base and a 5-hmC modified base. Furthermore, PCR amplification of hmC-containing oligonucleotides is highly inefficient, which hinders identification of hmC in a template by methods that require PCR amplification prior to detection, at least in part because there will be fewer hmC-containing amplicons produced. The present invention provides strategies that overcome these issues by combining bisulfite conversion with detection of changes in polymerase activity during template-directed nascent strand synthesis. For example, a duplex nucleic acid suspected of containing 5-MeC and/or 5-hmC can be subjected to bisulfite conversion, which converts cytosine to uracil, does not change 5-MeC, and converts 5-hmC to CMS. The template is subsequently subjected to a single-molecule template-directed sequencing reaction. The uracils present in the template (due to bisulfite conversion) can be distinguished from thymines using polymerase behavior, e.g., interpulse duration, pulse width, frequency of cognate sampling, accuracy of pairing, etc. If a complementary strand is also subjected to sequencing, then the complementary nucleotide sequence information can also be used to identify bases, as described above. Further, the $SO_3$ adduct added during the conversion of 5-hmC to CMS will enhance the response of the polymerase to the modified base (e.g., causing increased pausing) and thereby facilitate identification of CMS versus 5-MeC in the template.

As such, in certain embodiments a nucleic acid sample is fragmented and universal primers are attached to each resulting fragment. Bisulfite conversion is performed; the nucleic acid fragments are single-stranded and comprise the primer site, which facilitates subsequent priming and sequencing of the fragments. U is discriminated from T based on polymerase kinetics and standard bisulfite sequencing algorithms, with those bases detected as U known to have originally been C. Bases detected as C based on their base-pairing with G are known to be 5-MeC or CMS (originally 5-hmC). 5-MeC and CMS are discriminated based upon their relatively different kinetics, due at least in part to the $SO_3$ adduct present in CMS and absent in 5-MeC. Further, as with other modification-detection methods, nucleic acids known to have or suspected of having one or more modifications of interest can be targeted, e.g., using antibodies or other binding agents specific to the one or more modifications, and the nucleic acids containing the one or more modifications can be selected or "captured" by various methods known in the art, e.g., immunoprecipitation, column chromatography, bead separations, etc. Once the nucleic acids that do not contain the one or more modifications are removed, e.g., by washing, buffer exchange, etc., the selected nucleic acids can be subjected to template-directed sequencing to identify and/or map the one or more modifications. For additional information on the behavior of 5-hydroxymethylcytosine in conventional bisulfite sequencing, see Huang, et al. (2010) PLoS ONE 5(1):e8888, the disclosure of which is incorporated herein by reference in its entirety for all purposes.

Although methods are described in which bisulfite conversion is used to sequence unamplified nucleic acid templates, the invention also contemplates methods for improving amplification of bisulfite converted nucleic acids. In particular, amplification of bisulfite converted DNA is challenging, at least in part because it is difficult to design primers that can anneal to the converted DNA. This leads to amplification bias and a lower yield of amplicons from certain regions of the original nucleic acid sample. Multiple displacement amplification (MDA) is an isothermal, highly branched amplification technique that utilizes random hexamer primers and strand-displacing polymerases (e.g., phi29). In certain aspects, the present invention provides a method of performing amplification of bisulfite converted nucleic acid using MDA. This avoids the need to design PCR primers since the primers used are randomly generated. In certain embodiments, the primers can be modified to bind to bisulfite converted fragments by replacing the Gs with Ts. (Such modified primers could also be used in conventional PCR.) This strategy could improve the efficiency of and reduce the bias in MDA using post-bisulfite-conversion nucleic acids. The resulting amplicons can be sequenced, e.g., using single-molecule sequencing methods described herein, and compared to sequences generated using unconverted and optionally amplified nucleic acids to identify the modified bases (e.g., 5-MeC or 5-hmC) in the original nucleic acids. Further, the amplicons could be incorporated into circular constructs (e.g., as described in U.S. Ser. Nos. 12/383,855 and 12/413,258, both filed on Mar. 27, 2009 and incorporated herein by reference in their entireties for all purposes) for iterative sequencing reactions to generate redundant sequence information.

Glucosyltransferase Modification

In certain embodiments, DNA glucosyltransferases are used to transfer a glucose group to 5-hmC. DNA glucosyltransferases found in bacteriophage-infected *E. coli* transfer glucose from uridine diphosphate glucose (UDP-glucose) to hmC nucleotides in DNA. These enzymes are similar to the glucosyltransferase in trypanosomes that converts hydroxymethyluracil to base J, as described above. The enzymes can attach the glucose to hmC through an α or β linkage, as shown here:

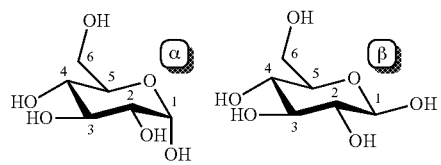

Exemplary enzymes for transferring glucose groups to hmC include, but are not limited to, T2-hmC-α-glucosyltransferase, T4-hmC-α-glucosyltransferase, T6-hmC-α-glucosyltransferase, and T2-hmC-β-glucosyltransferase. Other enzymes can be used to create diglucosylated hmC, such as T6-glucosyl-hmC-β-glucosyltransferase, which creates diglucosylated hmC with a β linkage between the two glucose groups. These enzymes are generally specific for hmC and do not typically alter other bases such as A, C, MeC, T, or G. As such, treating hmC-containing nucleic acids with such enzymes creates nucleic acids in which the hmC residues have been converted to monoglucosylated-hmC or multi-glucosylated-hmC. Glucosylated-hmC is much larger and bulkier than hmC, and therefore has a distinctive effect on polymerase activity when present in a template nucleic acid. Details on the glucosylation of 5-hmC by glucosyltransferases are known in the art, e.g., in Josse, et al. (1962) J. Biol. Chem. 237:1968-1976; and Lariviere, et al. (2004) J. Biol. Chem. 279:34715-34720.

The strategy for addition of glucose moieties to hmC described above can be modified in various ways. For example, currently known glucosylating enzymes (e.g., those that selectively glucosylate hmC or hmU) can be subjected to directed or molecular evolution to introduce mutations that improve the efficiency and/or specificity with which hmC is glucosylated, or that permit addition of adducts other than glucose to hmC. Alternatively or additionally, (a) the glucose adducts added could comprise a detectable label to provide another mode of detection, e.g., in addition to monitoring the kinetics of the reaction, and/or (b) further steps can be performed to add modifications in addition to the glucose adduct, e.g., that are linked to the nucleic acid through the glucose adduct. In yet further embodiments, a glucosyltransferase enzyme can be used that binds to the template but does not dissociate, and therefore results in a further modification (e.g., bound agent) that can be detected during single-molecule sequencing, e.g., by detection of a significant pause of nascent strand synthesis. Methods and strategies for detecting agent-nucleic acid interactions are detailed in section VI, below.

In further embodiments, both hmC and 5-MeC and be modified prior to sequencing. For example, the nucleic acid can be subjected to glucosylation to convert hmC to glucose-hmC, and subsequently the 5-MeC bases can be converted to hmC, e.g., using TET1 protein. Tet proteins used for this conversion can be from human, mouse, or another organism that expresses Tet proteins having similar activity to that of TET1. Further, Tet proteins include TET2, which is a homologue of TET1 that modifies RNA. (hmC is found in human RNA.) Detection of glucose-hmC will be indicative of an hmC in the original nucleic acid, and detection of hmC will be indicative of a 5-MeC in the original nucleic acid. Alternatively, the hmC generated by conversion of 5-MeC can be further modified to produce a greater enhancement of detection while maintaining a signal distinct from that of the glucose-hmC generated by conversion of hmC in the original nucleic acid. For example, an alpha linkage can be used to attach a glucose moiety to the original hmC, while a beta linkage is used to attach a glucose moiety to the 5-MeC-converted hmC. Alternatively or additionally, a different sugar group can be added to each, e.g., selected from glucose, maltose, sucrose, lactose, galactose, or multiples (e.g., di- or tri-glucosyl (or other sugar) groups) or combinations thereof. Yet further, the TET1 protein present in the solution can further modify the 5-MeC-converted hmC to the aldehyde (5-fC) and the carboxylic acid (5-caC) forms. These modifications have different kinetic signatures, including distinct IPDs, during sequencing. Their detection in the above-described assay is indicative of a 5-MeC in the original template nucleic acid molecule since the TET1 protein converts 5-MeC to hmC, and then converts hmC to 5-fC or 5-caC. (See, e.g., Ito, et al. (2011) Science 333: 1300-1303, incorporated herein by reference in its entirety for all purposes.) It is also contemplated that any of these modified bases can be subjected to a yet further modification to enhance detection during real time sequencing, e.g., by increasing the kinetic signal.

Yet further, in certain embodiments it may not be necessary to distinguish between 5-MeC and 5-hmC in the initial nucleic acid sample, and the nucleic acid can be treated with a Tet enzyme to convert both 5-MeC and 5-hmC to 5-caC in the sequencing template. The resulting sequencing reads are analyzed to identify locations having a 5-caC nucleotide, which indicates that the original nucleic acid contained either a 5-MeC or a 5-hmC at that position.

Further, modifications to the template can be performed at many different stages of the method. For example, they can be introduced to a genomic DNA sample before or after fragmentation or shearing; they can be introduced after a nucleic acid fragment is incorporated into a sequencing template; they can be introduced in solution or at the reaction site, e.g., where a reaction component is immobilized; and/or they can be introduced within the reaction mixture, e.g., in the presence of a polymerase or other sequencing enzyme.

In further embodiments, a nucleic acid sample can be divided into aliquots, each of which is subsequently subjected to a different treatment (including "no treatment") prior to sequencing. For example, one aliquot may be left untreated while another is subjected to glucosylation, glycosylation, chemical modification, etc. The sequence data generated from the different aliquots is analyzed and compared, and differences in the sequence reads are indicative of modifications in the original template and/or in the modified template. For example, a genomic sample suspected of comprising 5-MeC and/or hmC nucleobases can be split into two aliquots, A and B. Aliquot A is treated with a glucosyltransferase to convert all hmC nucleobases to glucose-hmC, and is subsequently sequenced. Aliquot B is subjected to TET1 treatment to convert 5-MeC nucleobases to hmC, followed by treatment with a glucosyltransferase to convert all hmC (including those in the original nucleic acid sample) to glucose-hmC. After the two conversion steps, aliquot B is sequenced. The kinetic signatures from the sequencing of the nucleic acids in aliquot A are compared to the kinetic signatures from the sequencing of the nucleic acids in aliquot B. Those loci that have glucose-hmC in both aliquots were originally hmC, and those loci that have glucose-hmC in only aliquot B were originally 5-MeC. In this way, the distinct kinetic signature associated with hmC during single-molecule sequencing can be used to identify both hmC and 5-MeC within a nucleic acid sample.

Enrichment Strategies

In certain aspects, the use of binding agents specific for modifications of interest can facilitate enrichment of a nucleic acid preparation of those modifications. A plethora of agents can specifically bind a variety of modifications within a nucleic acid molecule, and these agents can also be used as a "tag" for isolating nucleic acids having modifications from a mixture of nucleic acids. In some embodiments, an antibody specific for a modification of interest is introduced to a nucleic acid sample suspected of having the modification under conditions that promote binding of the antibody to the modification. The binding agent is typically linked to a solid support, e.g., a bead or column, such that nucleic acids that are not bound can be removed, e.g., by washing or buffer exchange. Subsequently, the nucleic acids bound to the binding agent are released and subjected to sequencing with most or all of the nucleic acids sequenced having the modification of interest. In certain embodiments, a modification-comprising nucleic acid may be further modified to facilitate capture. For example, T4 phage β-glucosyl-transferases can add a glucose moiety to 5-hydroxymethylcytosine within a nucleic acid template, and binding agents (e.g., antibodies) specific to the resulting glucosyl-5-hydroxymethylcytosine can be used to enrich for nucleic acids comprising this modified base. Other binding agents can also be used for such enrichment procedures, to the extent that they can either be immobilized themselves, or be bound by an immobilized binding agent, e.g. an antibody other binding partner. Further, where multiple different modifications are to be sequenced, multiple enrichments can be performed, e.g., within a single reaction mixture where all modifications are collected together, or in separate aliquots of the original nucleic acid sample where each modification is separately enriched.

In certain preferred embodiments, a nucleic acid sample is exposed to a binding agent that specifically binds a modification of interest, the nucleic acid sample is fragmented, and fragments comprising the modification are retained by virtue of their association with the binding agent, thereby enriching the retained nucleic acid sample for fragments of interest. This "enriched sample" is optionally divided into two aliquots, only one of which is subjected to an amplification reaction that does not maintain the modifications in the resulting amplicons. These amplicons represent the regions of the original nucleic acid sample that comprised the modifications, but since the modifications are no longer present they serve as the reference sequence to which the sequence of the unamplified fragments in the enriched sample (i.e., which still comprise the modifications) will be compared. The fragments in both the amplified unamplified aliquots are sequenced and statistically analyzed to determine positions at which they differ, which are indicative of base modifications in the original template. Although the enrichment step is preferred, it is not required. For example, the original nucleic acid sample can also be divided and only a portion amplified to remove the modifications and provide a "reference" sample. In certain embodiments, the amplified and unamplified fragments (whether enriched or not) are capped with hairpins or stem-loop structures to create closed, circular sequencing templates, which can optionally comprise different "barcode" sequences that allow sequenced-based identification of the origin of the fragment contained therein, i.e., the amplified or unamplified portion. In such embodiments, the two template preparations can be included in the same sequencing reaction, e.g., in an arrayed format, and the resulting sequence information can be analyzed to both determine whether a particular fragment is from the amplified or unamplified aliquot, and to identify modifications present in the unamplified fragments, and therefore the original nucleic acid sample. Sequencing both amplified and unamplified fragments together is particularly beneficial to ensure that sequencing reaction conditions are identical for both, thereby reducing experimental variation. Other alterations to the described methods will be recognized by those of ordinary skill in the art in light of the teachings herein. For example, the sequence determination can be carried out by other methodologies well known in the art.

IX. Data Analysis

Analysis of the data generated by the methods described herein is generally performed using software and/or statistical algorithms that perform various data conversions, e.g., conversion of signal emissions into basecalls, conversion of basecalls into consensus sequences for a nucleic acid template, and conversion of various aspects of the basecalls and/or consensus sequence to derive a reliability metric for the resulting values. Such software, statistical algorithms, and use thereof are described in detail, e.g., in U.S. Patent Publication No. 20090024331 and U.S. Ser. No. 61/116,439, the disclosures of which are incorporated herein by reference in their entireties for all purposes. Specific methods for discerning altered nucleotides in a template nucleic acid are provided in U.S. Ser. No. 61/201,551, filed Dec. 11, 2008, and incorporated herein by reference in its entirety for all purposes. These methods include use of statistical classification algorithms that analyze the signal from a single-molecule sequencing technology and detect significant changes in one or more aspects of signal morphology, variation of reaction conditions, and adjustment of data collection parameters to increase sensitivity to changes in signal due to the presence of modified or damaged nucleotides. In certain aspects, the invention provides methods for detecting changes in the kinetics (e.g., slowing or pausing, changes in pulse width or interpulse duration, or changes in the kinetics of cognate or non-cognate sampling) or other reaction data for real-time DNA sequencing. As discussed at length above, detection of a change in such sequencing applications can be indicative of secondary structure in the template, the presence of modifications in the template, the presence of an agent bound to the template, and the like. Specific methodologies, algorithms, and software implementations for detecting modifications within nucleic acids molecules is further described in PCT Application Publication No. WO 2012/065043, incorporated herein by reference in its entirety for all purposes. In particular, methods are provided to analyze the data generated in the vicinity of a kinetic change, and algorithmic methods for classifying and removing or down-weighting the occurrence of the change in the context of single-molecule sequencing. General information on algorithms for use in sequence analysis can be found, e.g., in Braun, et al. (1998) Statist Sci 13:142; and Durbin, et al. (1998) *Biological sequence analysis: Probabilistic models of proteins and nucleic acids*, Cambridge University Press: Cambridge, UK. Algorithms for the identification of regions in sequence data belong to the general category of sequence labeling or segmentation algorithms, which are generally known in the art. The mapping of this problem to sliding-window analysis, HMMs, or CRFs is natural in this context. Other algorithms that approach the same problem are multiple change-point analysis such as the Gibbs sampler (see, e.g., Lee, P. M. (2004) *Bayesian Statistics: An Introduction*, Oxford University Press: New York, N.Y., the disclosure of which is incorporated herein by reference in its entirety for all purposes), or locally weighted polynomial regression (see, e.g., Braun, et al., supra).

Figure 4:
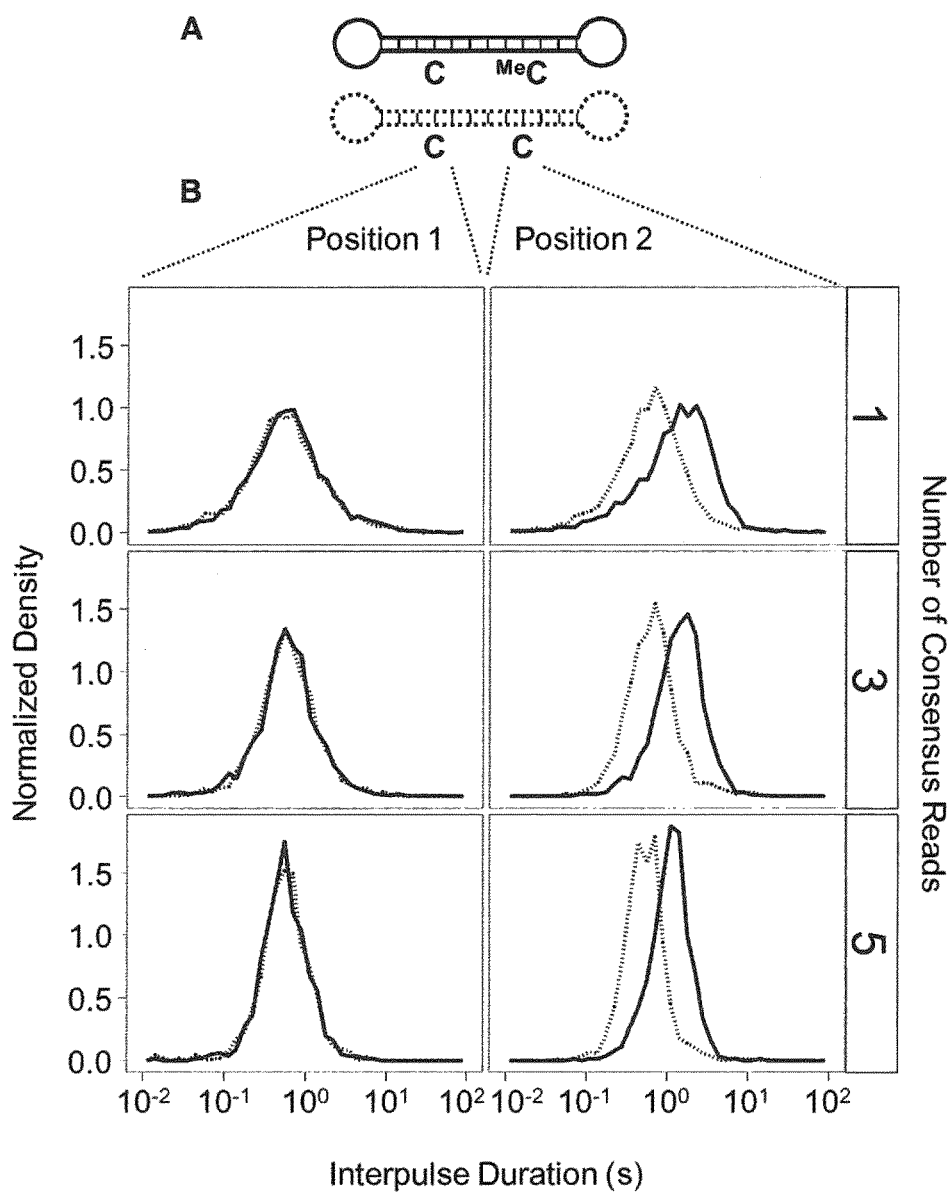
FIG. 4A provides a schematic for exemplary template nucleic acids of the invention.
FIG. 4B provides graphs plotting interpulse duration for template nucleic acids as depicted in 4A.
Figure 7:
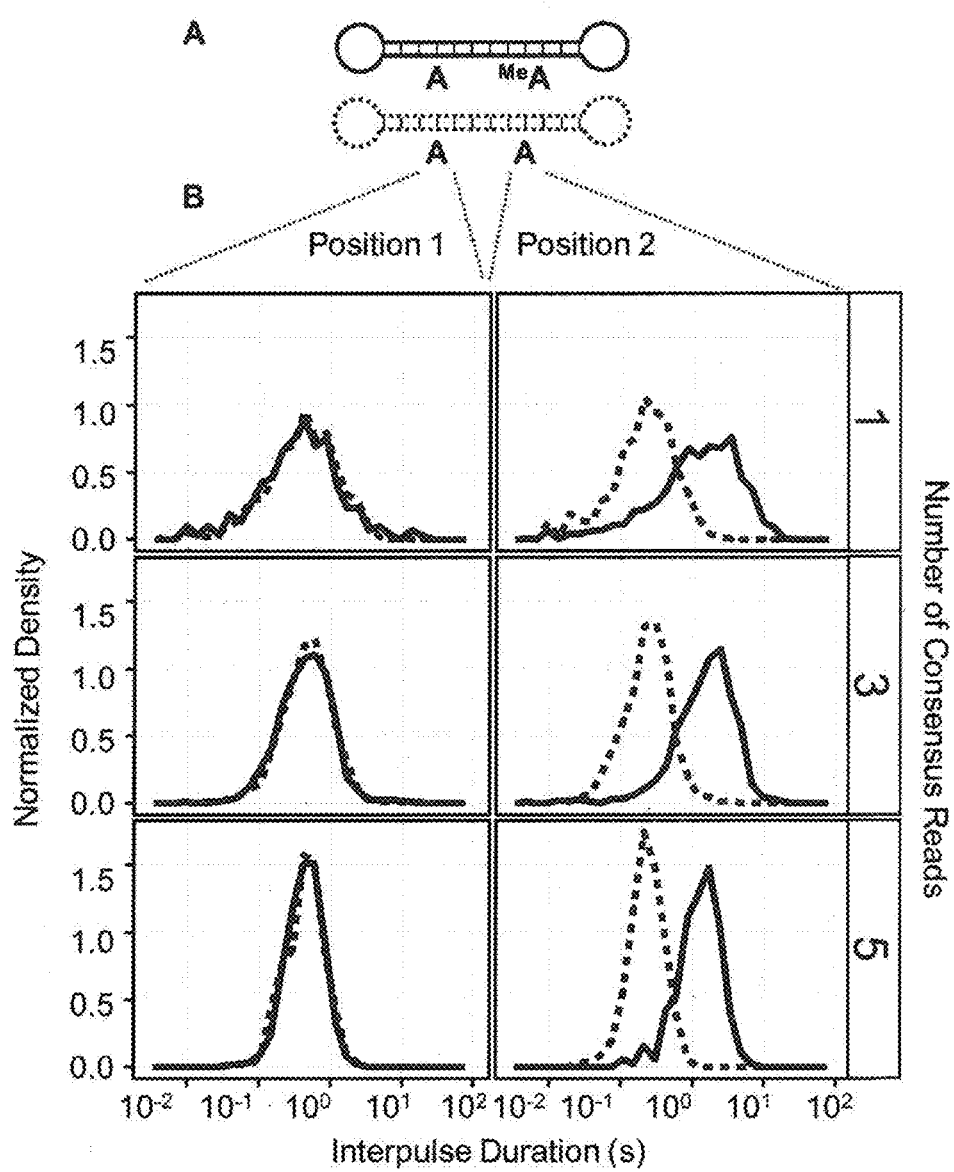
FIG. 7A provides a schematic for exemplary template nucleic acids of the invention.
FIG. 7B provides graphs plotting interpulse duration for template nucleic acids as depicted in 7A.
FIG. 7C provides a ROC curve for the data provided in 7B.

In general, data analysis methods benefit when the sequencing technology generates redundant sequence data for a given template molecule, e.g. by molecular redundant sequencing as described above. The distribution of IPDs for each read at that position is an exponential. The decay constant for the exponential of a methylated base and for that of an unmethylated base may be different. However, because of the large amount of overlap between two exponentials, it is still challenging to use one read to distinguish between the two populations. However, if one takes the mean of multiple reads at a single position, the distribution of this mean is a gamma function (convolution of several exponentials), which is more Gaussian-like and better separated than exponentials. This enables better distinguishability of the two populations. For example, FIG. 7 provides actual data showing that for two different positions in a single circular template, one always unmethylated, and one differentially methylated, an increase in the number of reads for the template corresponds to an increased resolution between IPDs for methylated vs. unmethylated adenosines. If the underlying distributions are exponential, as just discussed, then the mean value is the only metric that can be used for making the distinction (the standard deviation is the same as the mean). If the distribution is non-exponential for each read position, as it would be for the methylcytosine IPD' that is weighted over numerous neighboring positions and thus itself has a gamma-like distribution, then when doing consensus reads of the same position, one can take into account the mean of the gamma-like weighted IPD' distributions along with other information, e.g. its standard deviation, its skewness, or other characteristics of the distribution. FIG. 4 shows actual molecular consensus distributions for methylcytosine, given the underlying gamma-like weighted IPD' distributions of individual reads, but in this figure only the means of these underlying distributions were utilized. The plotted distributions could become even more well-separated if other characteristics had been taken into account. The data used to generate FIGS. 7 and 4 is more fully described in the Examples herein.

Figure 8:
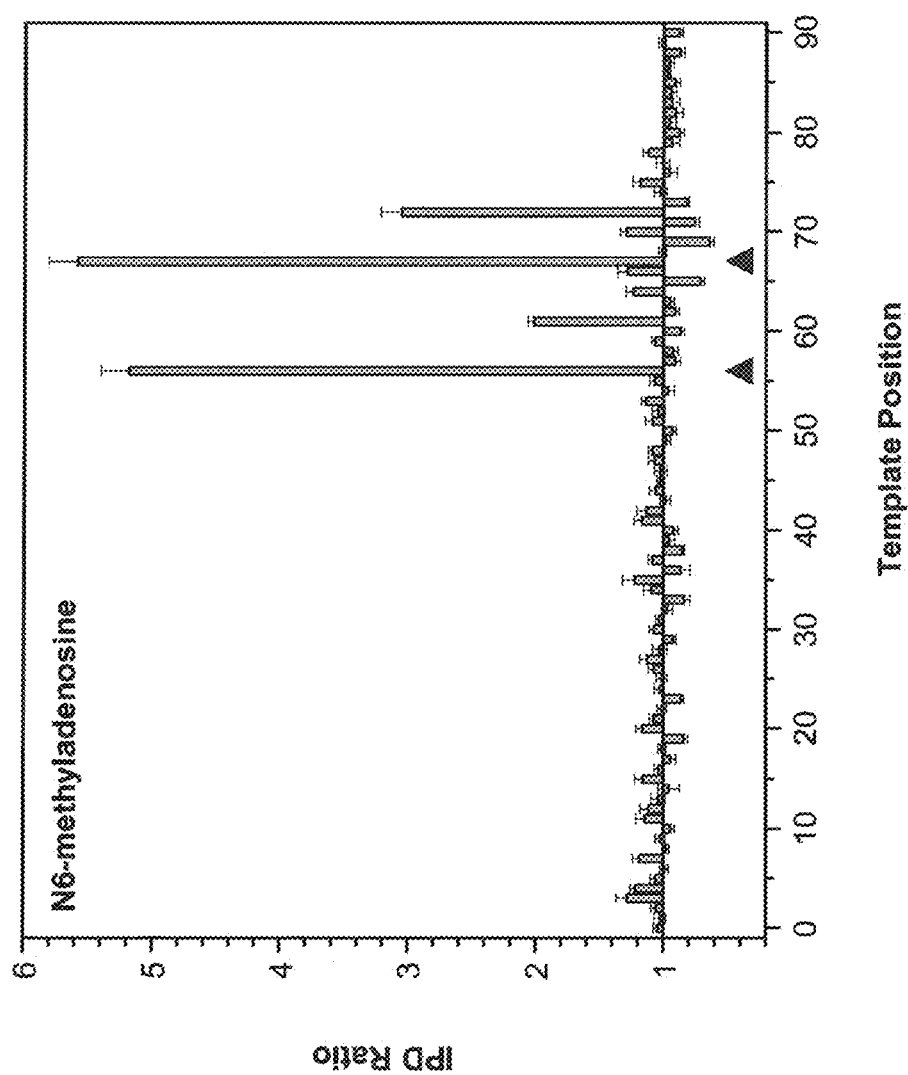
FIG. 8 provides a graph plotting IPD ratio against template position for a template nucleic acid comprising $N^6$-methyladenosine modifications.

Although described primarily in the context of detection of methyl cytosine, these methods are also applicable to methyladenosine or any other base modification for which IPDs are used as a metric for detection. FIG. 8 provides data showing differences between ratios of IPDs for methylated adenosines and unmethylated adenosines in a template nucleic acid, and the data used to generate FIG. 8 is further described in the Examples herein. This data also shows that $N^6$-methyladenosine, like methylcytosine, has an effect on IPD not only at the methylated base but also at multiple, neighboring positions, as well. Further, in light of the above teachings it will be clear to one of ordinary skill that the approach can be extended to pulse metrics other than IPD, such as pulse width, branch rate, mismatch rate, deletion rate, etc. In addition, the general classifier approach suggested in steps 2+3 can be implemented with many standard statistical classification algorithms, i.e. linear discriminant analysis, multi-dimensional regression, kernel methods, classification and regression trees, neural networks, and support vector machines. The approach can also incorporate data from multiple strands of a duplex template. For example, because the CG sequence for cytosine methylation and the GATC sequence for adenosine methylation is the same on the reverse complement strand, these bases can be methylated on both complementary strands. If the general statistical distribution for the fraction of sites that are hemi-methylated vs. fully methylated is known, then information regarding IPD or other metrics gained from the complementary strand can be used to increase the accuracy with which a call is made on a particular strand. For example, if after analyzing each strand separately it is concluded that there is a 95% chance that stand A is methylated and a 55% chance that complementary strand B is methylated, but it is known that there is a 80% chance that if one strand is methylated then so is the other, then the confidence in calling strand B as methylated is increased.

Further, the incorporation of a double-stranded nucleic acid fragment into a closed circular single-stranded template (e.g., as described in U.S. Patent Publication No. 20090298075) elegantly allows comparison of the polymerase kinetics on the forward and reverse strand. Since the forward and reverse strands are reverse complements of each other, one must construct the expectation of the ratios of the parameters of interest (e.g., pulse width, IPD, etc.) from an entirely unmodified sample, e.g., using amplification to produce amplicons that do not comprise the modification(s). The subsequent analysis on the sample comprising the modifications comprises performing a likelihood analysis that the ratio observed is sufficiently different from the expected ratio. This means that all other aspects of the experiment are normalized out since they are identical for sequencing on the forward and reverse strands. For example, in SMRT® sequencing, such aspects of the experiment include, but are not limited to, the specific polymerase, its position in the reaction site (e.g., within a ZMW), the illumination (e.g., beamlet alignment, power, wavelengths, etc.), temperature at that reaction site, local concentrations of reactants (e.g., polymerase, nucleotides, etc.), and the like. Each time the modification is sequenced as the polymerase repeatedly translocates around the template, the sequence data generated directly adds to the confidence in the ration and informs the p-value confidence in whether a modification is present at a specific position within the template.

X. Systems

The invention also provides systems that are used in conjunction with the compositions and methods of the invention in order to provide for real-time single-molecule detection of analytical reactions. In particular, such systems typically include the reagent systems described herein, in conjunction with an analytical system, e.g., for detecting data from those reagent systems. In certain preferred embodiments, analytical reactions are monitored using an optical system capable of detecting and/or monitoring interactions between reactants at the single-molecule level. For example, such an optical system can achieve these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously (e.g., multiple types of differentially labeled reaction components). A wide variety of photon detectors or detector arrays are available in the art. Representative detectors include but are not limited to an optical reader, a high-efficiency photon detection system, a photodiode (e.g. avalanche photo diodes (APD)), a camera, a charge-coupled device (CCD), an electron-multiplying charge-coupled device (EMCCD), an intensified charge coupled device (ICCD), and a confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. Illustrative examples of such optical transmission or reflection elements are diffraction gratings, arrayed waveguide gratings (AWG), optical fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provides a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g., zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g., in U.S. Patent Pub. No. 20060063264, filed Sep. 16, 2005, which is incorporated herein by reference in its entirety for all purposes.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (see, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007, now abandoned; and U.S. patent application Ser. No. 12/134,186, filed Jun. 5, 2008, now U.S. Pat. No. 8,182,993, the full disclosures of which are incorporated herein by reference in their entirety for all purposes.

Further, the invention provides data processing systems for transforming raw data generated in an analytical reaction into analytical data that provides a measure of one or more aspects of the reaction under investigation, e.g., transforming signals from a sequencing-by-synthesis reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis. For clarity of description, details of known techniques are not provided herein. These techniques are discussed in a number of available reference works, such as those provided in U.S. Patent Publication No. 20090024331 and U.S. Ser. No. 61/116,439, filed Nov. 20, 2008, the disclosures of which are incorporated herein by reference in their entireties for all purposes.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data; c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed, a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

Figure 3:
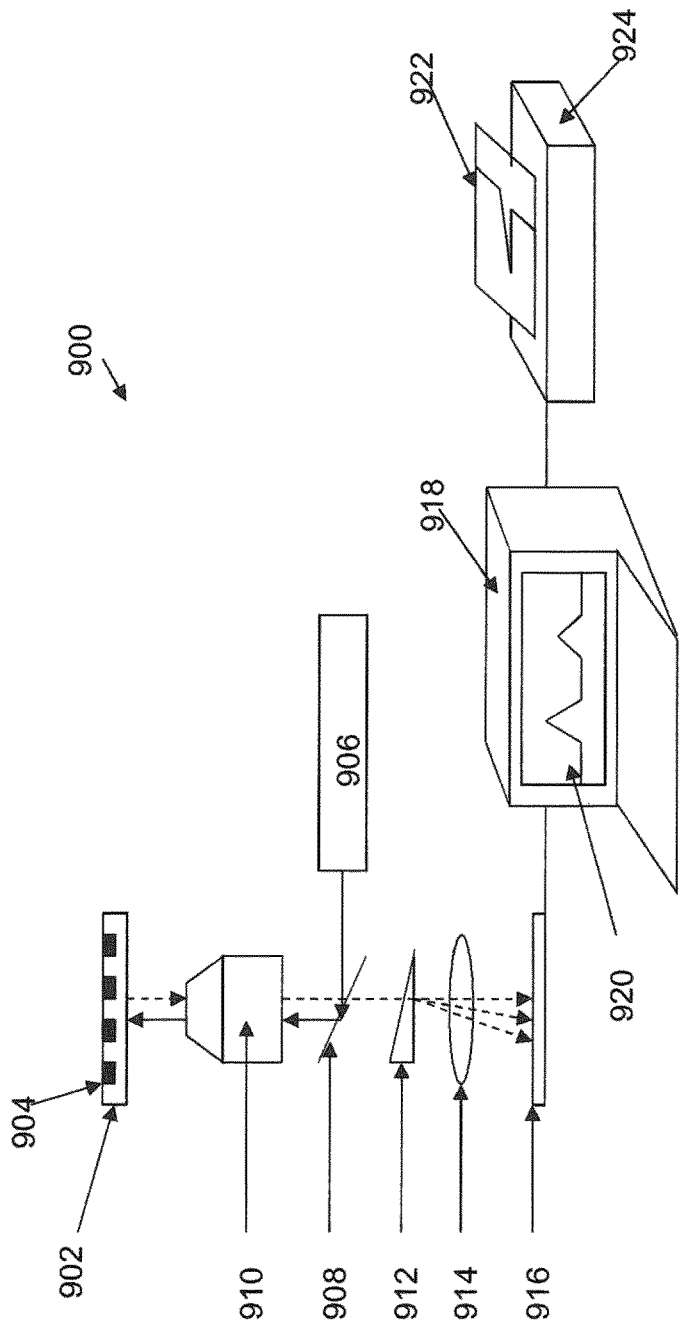
FIG. 3 provides an illustrative example of a system of the invention.

As shown in FIG. 3, the system 900 includes a substrate 902 that includes a plurality of discrete sources of chromophore emission signals, e.g., an array of zero mode waveguides 904. An excitation illumination source, e.g., laser 906, is provided in the system and is positioned to direct excitation radiation at the various signal sources. This is typically done by directing excitation radiation at or through appropriate optical components, e.g., dichroic 908 and objective lens 910, that direct the excitation radiation at the substrate 902, and particularly the signal sources 904. Emitted signals from the sources 904 are then collected by the optical components, e.g., objective 910, and passed through additional optical elements, e.g., dichroic 908, prism 912 and lens 914, until they are directed to and impinge upon an optical detection system, e.g., detector array 916. The signals are then detected by detector array 916, and the data from that detection is transmitted to an appropriate data processing system, e.g., computer 918, where the data is subjected to interpretation, analysis, and ultimately presented in a user ready format, e.g., on display 920, or printout 922, from printer 924. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901, 273, all of which are incorporated herein by reference in their entireties for all purposes.)

XI. Bar Coding Applications

Many genomic applications use unique non-natural DNA sequences ("bar codes") to provide sequence-encoded sample tracking. DNA bar codes are designed to be highly detectable against the dominant sequence composition expected for a particular genomic sample. Current methods rely exclusively on the differences in the base sequence composition of the bar codes. However, these base-sequence-based bar-coding methods can fail due to base-calling errors that are inherent to in single-molecule sequencing methods, thereby limiting the ability to experimentally distinguish the bar codes from each other and from the biological nucleic acid under investigation.

In certain aspects, the present invention provides methods for improving the ability to distinguish between different bar codes, as well as between bar code sequence reads and template sequence reads. For example, modifications to be used in bar codes can be selected based upon their prevalence in the organism providing the genetic material to be analyzed, e.g., to avoid modified bases that might be present in the sample nucleic acids. This provides an additional way to distinguish between bar code sequences and sample nucleic acids being sequenced. In certain embodiments, the methods comprise addition of modifications to a bar code sequence in order to facilitate detection during single-molecule sequencing. For example, a bar code sequence can be subjected to methylation, hydroxymethylation, glycosylation, or addition of other moieties that cause a distinct change in polymerase kinetics. In some embodiments, modified nucleotides can be incorporated into a bar code sequence by known synthesis methods, e.g., phosphoramidite synthesis. In other embodiments, a bar code sequence can be modified to contain non-natural bases. (See, e.g., Krueger, et al. (2009) Chem. Biol. 16(3):242-248, incorporated herein by reference in its entirety for all purposes.) Alternatively, a bar code sequence can comprise a binding site for a binding agent that, when bound to the template, detectably alters polymerase activity. Other methods for modifying nucleic acids to alter the kinetic signature of a polymerase during nascent strand synthesis described elsewhere herein can also be used. Adaptors comprising these bar codes can be linked to sample nucleic acids prior to sequencing. In certain preferred embodiments, the adaptors comprising these bar codes are stem-loop adaptors as described elsewhere herein and in U.S. Ser. No. 12/383,855, now U.S. Pat. No. 8,236,499; and Ser. No. 12/413,258, now U.S. Pat. No. 8,153,375; both filed on Mar. 27, 2009 and incorporated herein by reference in their entireties for all purposes. During a sequencing reaction, the resulting barcode sequence read is identifiable not only on the basis of the base sequence information generated, but also on the basis of the activity (e.g., kinetics, etc.) of the polymerase enzyme as it processes the template molecule.

XIII. Examples

Detection of 5-methylcytosine (5-MeC)

Methylation sequencing on a SMRT® Sequencing platform (see, e.g., P. M. Lundquist, et al., supra) was performed on short, synthetic DNA oligos with contrived patterns of methylated and unmethlyated bases, along with control sequences having the same primary sequence but without any methylation. These templates provided unequivocal fluorescence pulse patterns and tempos that demonstrated how the combination of sequence context and methylation status affected interpulse duration. For example, SMRT® sequencing experiments were performed using synthetic DNA templates that only differed by a single methylated vs. unmethylated cytosine. The difference in average interpulse durations between the two templates was visible both at the 5-MeC position and in the vicinity of the 5-MeC position.

Because the interpulse duration between any two successive incorporation events is stochastic in nature and has an exponential distribution (Eid, et al., supra), a single sequencing measurement may not always yield enough information to determine methylation status with certainty. Therefore, in certain embodiments a highly processive, strand-displacing polymerase is used, and this polymerase carries out multiple laps of synthesis around a circular DNA template (J. Korlach, et al., *Proc Natl Acad Sci USA* 2008, supra). This mode of operation provides repeated sequencing of the same DNA molecule to generate multiple sequence reads, e.g., by rolling circle replication. The statistical distribution of interpulse durations obtained at a particular template site will thus indicate its methylation state.

In particular, FIG. 4A shows a schematic of two templates for use in SMRT® sequencing. Both comprise a double-stranded region flanked by two single-stranded hairpins or stem-loop structures (also referred to as a "SMRTbell™ template"). A polymerase binds to a primed location on the template, e.g., via a primer hybridized to one of the single-stranded hairpins, and commences processing the template to generate a nascent strand complementary to the strand upon which the polymerase is translocating. The strand displacement activity of the polymerase permits passage through the double-stranded region which is unwound to transform the template into a circular form. The polymerase then proceeds around the other single-stranded hairpin and on through the previously displaced strand of the double-stranded region. The polymerase can continue to process the template in a "rolling-circle" fashion to generate a concatemer comprising multiple copies of complements to both strands of the double-stranded region, as well as the hairpins. The two templates are identical except at position 2, where the top template comprises a methylated cytosine (5-MeC) and the bottom template comprises a non-methylated cytosine. (Position 1 is a non-methylated cytosine in both templates.) FIG. 4B provides an illustrative depiction of the difference in IPD for the methylated template as compared to the unmethylated template. For each row, the histograms depict the distributions of mean weighted IPD (averaged over the labeled number of circular consensus sequencing subreads (in this context, a sequence read generated from a single pass of the polymerase around the template). Specifically, "1" indicates the sequencing data was derived from a sequence read generated in a single pass around the template; "3" indicates the data was derived from a sequence read generated in three passes around the template; and "5" indicates the data was derived from a sequence read generated in five passes around the template. The data from the methylated template is shown as a solid line, and the data from the unmethylated template is shown as a dotted line. At Position 1, the distributions of weighted IPD for the two templates are very similar. At Position 2, the average weighted IPD after a single subread (top histogram) is longer in the methylated template than in the unmethylated template. After 3 and 5 circular subreads, the distributions overlap even less. The interpulse duration (IPD) was clearly lengthened by the presence of 5-MeC. These results demonstrated the ability to use SMRT® sequencing technology to perform methylation sequencing of DNA. Weighted IPDs are described elsewhere herein.

Figure 5:
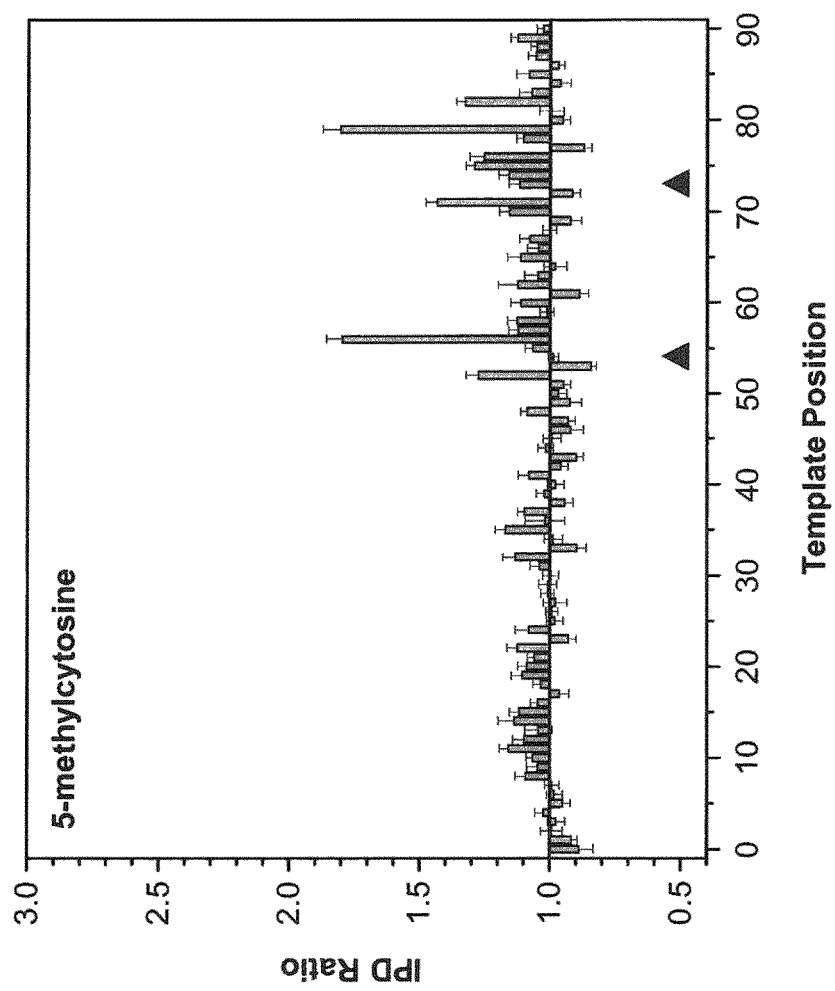
FIG. 5 provides a graph plotting IPD ratio against template position for a template nucleic acid comprising 5-methylcytosine modifications.

Further, methylcytosine was shown to have an effect on interpulse duration (IPD) not only at the methylated base, but over a range of several bases upstream and downstream of the position of the methylcytosine. Specifically, an increase in IPD was observed at some positions in the presence of methylcytosine relative to the same position in the absence of methylcytosine. FIG. 5 provides a plot depicting the ratio of the average IPD in the methylated template to the average IPD in the unmethylated template, plotted versus DNA template position. The two templates are identical except for the methylated bases in the methylated template, which are indicated by arrowheads in FIG. 5.

Figure 6:
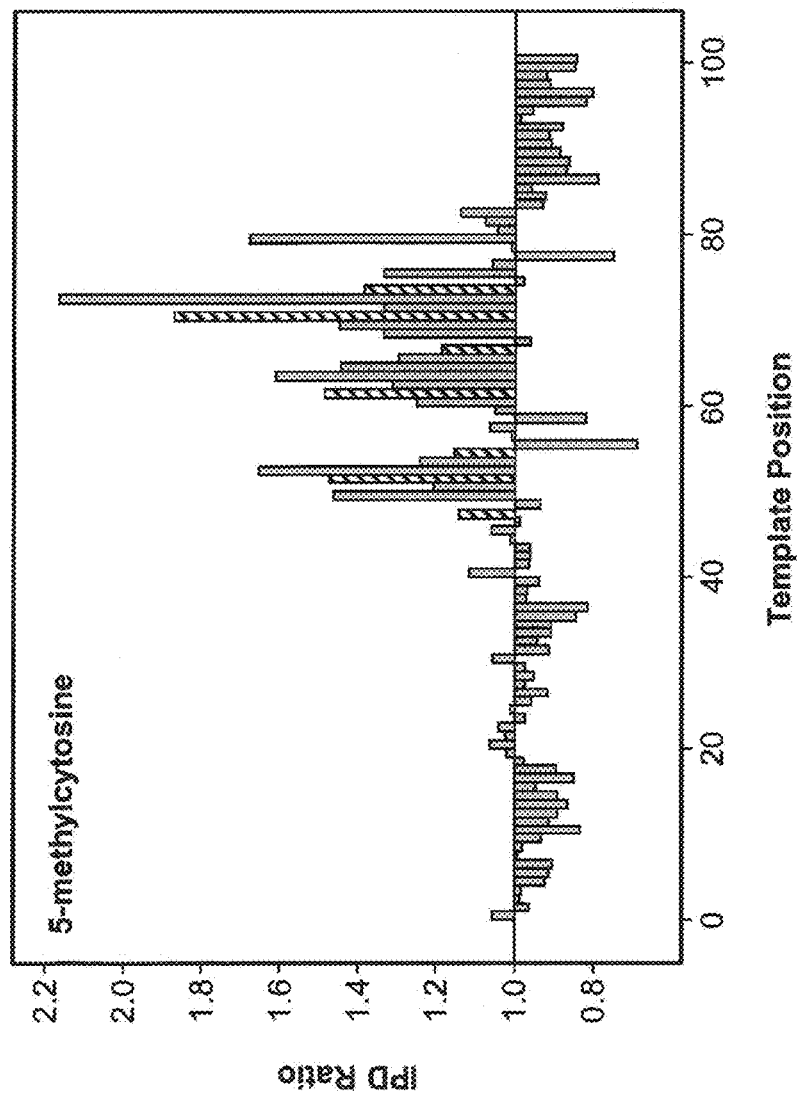
FIG. 6 provides a graph plotting IPD ratio against template position for a template nucleic acid comprising 5-methylcytosine modifications.

FIG. 6 provides another data set illustrating the ratio of IPD for a different methylated template vs. an identical but unmethylated template as a function of position. Seven cytosines (shown with crosshatching) were differentially methylated (5-MeC) between the two templates. That data clearly showed that IPD was increased in the region comprising the methylated bases. Interestingly, the effect on IPD occurred mostly downstream of the methylated positions. As such, data from nascent strand synthesis at positions in the template that are near the differentially methylated site, in addition to the differentially methylated site itself, is useful for methylation detection during real-time nascent strand synthesis.

Detection of $N^6$-methyladenosine ($N^6$-MeA)

Similar methods as those used to detect 5-MeC were used to detect $N^6$-MeA in similarly constructed template nucleic acids. FIG. 7A shows a schematic of two templates, both of which comprise a double-stranded region flanked by two single-stranded hairpins or stem-loop structures (also referred to as "SMRTbell™ templates"). The methylated template has an A within a GATC context at Position 1 and a $^m$A within a GATC context at Position 2, whereas the unmethylated template has an A at both positions. Otherwise, the two templates are identical. As described above, a polymerase binds to a primed location on the template and commences processing the template to generate a nascent strand, using its strand displacement activity to unwind the double-stranded region and proceed around the template. FIG. 7B shows plots of mean IPD generated from sequencing data using these two templates for varying numbers of consensus reads, as described above. The data from the methylated template is shown as a solid line, and the data from the unmethylated template is shown as a dotted line. For each row in FIG. 7B, the histograms depict the distributions of mean IPD (averaged over the labeled number of consensus sequencing subreads, i.e. the number of times the polymerase made one complete pass around the template to generate a complementary nascent strand). At Position 1, the distributions of IPD for the two templates are very similar. At Position 2, the average IPD after a single subread (top histogram) is ~5× longer in the methylated template than in the unmethylated template. After 3 and 5 circular subreads, the distributions overlap even less. The interpulse duration (IPD) was clearly lengthened by the presence of $N^6$-MeA, demonstrating that the SMRT® sequencing technology can be used to perform methylation sequencing of DNA comprising a methylated base other than 5-MeC. Further details on the detection of $N^6$-MeA, as well as other modifications within a template nucleic acid, are provided in Flusberg, et al. (2010) Nature Methods 7(6):461-465, incorporated herein by reference in its entirety for all purposes.

Receiver operating characteristic (ROC) curves, parameterized by IPD threshold, for assigning a methylation status to an adenosine nucleotide are provided in FIG. 7C. True positive means that an $^m$A is correctly called as $^m$A, whereas a false positive means that an A is mistakenly called as $^m$A. These ROC curves, based on the IPD distributions from Position 2 in FIG. 7B, are shown for a single read (solid line), and for 3 (long-dashed line) or 5 (short-dashed line) molecular redundant sequencing reads produced by the polymerase processing the template one, three, or five times, respectively. The dotted horizonal line bisecting the graph depicts the ROC curve for randomly guessing the methylation status. The normalized area under the ROC curve is 0.80 after the first circular subread but increases to 0.92 and 0.96 after three and five circular subreads, respectively. In fact, after five subreads, >85% of $^m$A bases can be detected at this template position with a false positive rate of only ~5%.

Like methylcytosine, methyladenosine was also shown to have an effect on IPD over a range of several bases upstream and downstream of the position of the methyladenosine. Specifically, an increase in IPD was observed at some positions in the presence of methyladenosine relative to the same position in the absence of methyladenosine. FIG. 8 provides a plot depicting the ratio of the average IPD in the methylated template to the average IPD in the unmethylated template, plotted versus DNA template position. The two templates are identical except for the methylated bases in the methylated template, which are indicated by arrowheads in FIG. 8.

Detection of 5-hydroxymethylcytosine

Figure 9:
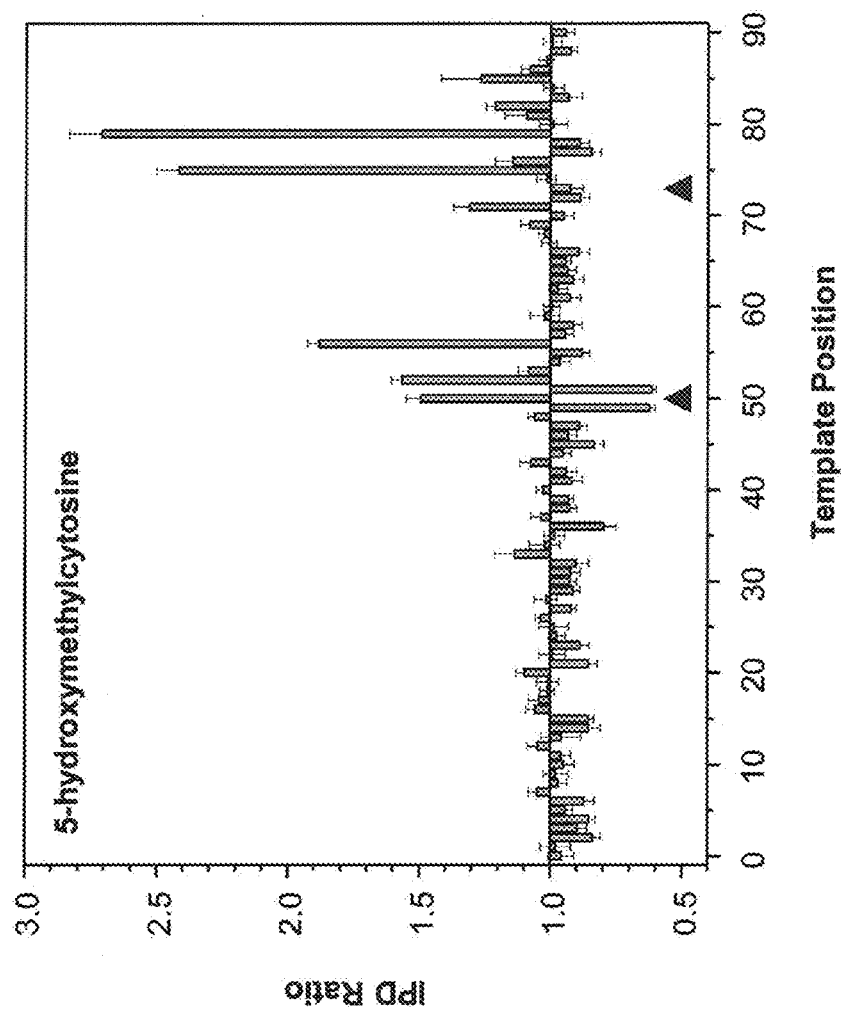
FIG. 9 provides a graph plotting IPD ratio against template position for a template nucleic acid comprising 5-hydroxymethylcytosine modifications.
Figure 10:
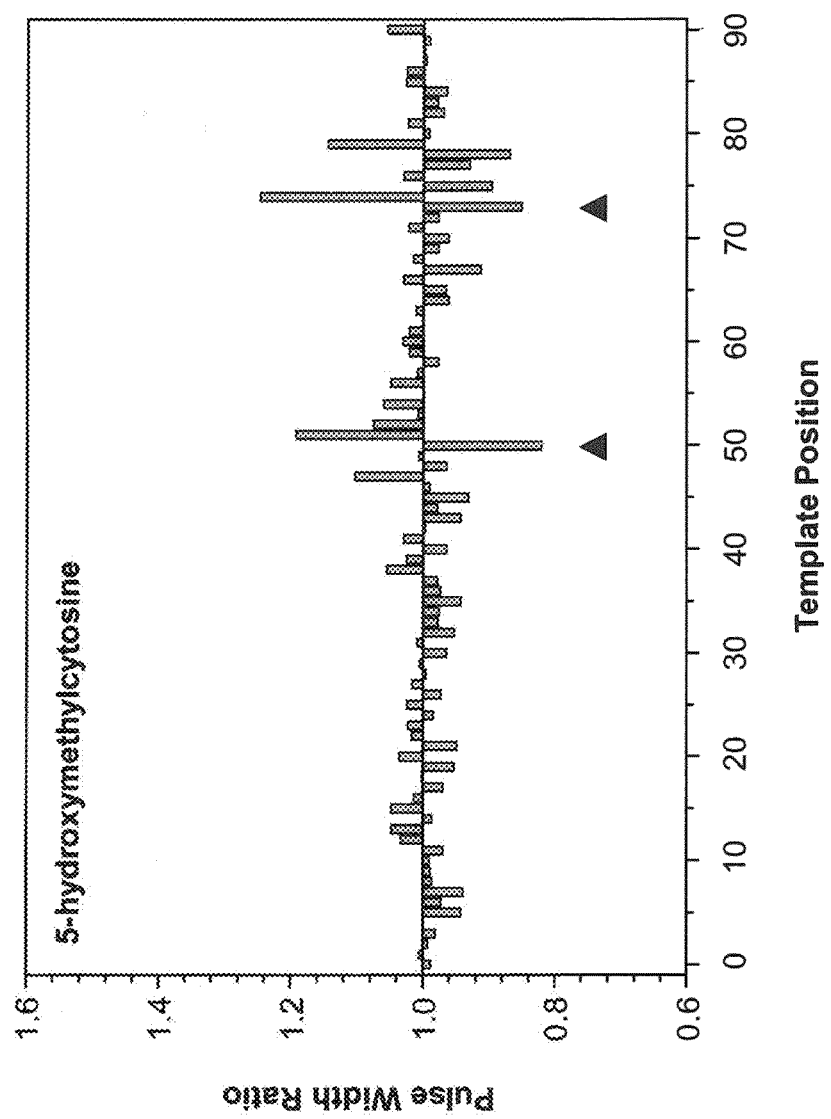
FIG. 10 provides a graph plotting pulse width ratio against template position for a template nucleic acid comprising 5-hydroxymethylcytosine modifications.

Similar to 5-MeC and N$^6$-MeA, 5-hydroxymethylcytosine was also tested and shown to have an effect on IPD over a range of several bases upstream and downstream of the position of the 5-hydroxymethylcytosine. Specifically, an increase in IPD was observed at some positions in the presence of 5-hydroxymethylcytosine relative to the same position in the absence of 5-hydroxymethylcytosine. FIG. 9 provides a plot depicting the ratio of the average IPD in the hydroxymethylated template to the average IPD in the unmethylated template, plotted versus DNA template position. The two templates are identical except for the hydroxymethylcytosine in the hydroxymethylated template, which are indicated by arrowheads in FIG. 9. Templates comprising 5-hydroxymethylcytosine bases were also tested and the presence of these modifications was shown to have an effect on pulse width. FIG. 10 provides a plot of pulse width ratio (pulse width for methylated template divided by pulse width for unmethylated template) vs. template position where the modified positions comprise 5-hydroxymethylcytosine bases. Variably hydroxymethylated positions are indicated by the arrowheads.

Detection of glucose-modified 5-hydroxymethylcytosine

Figure 11:
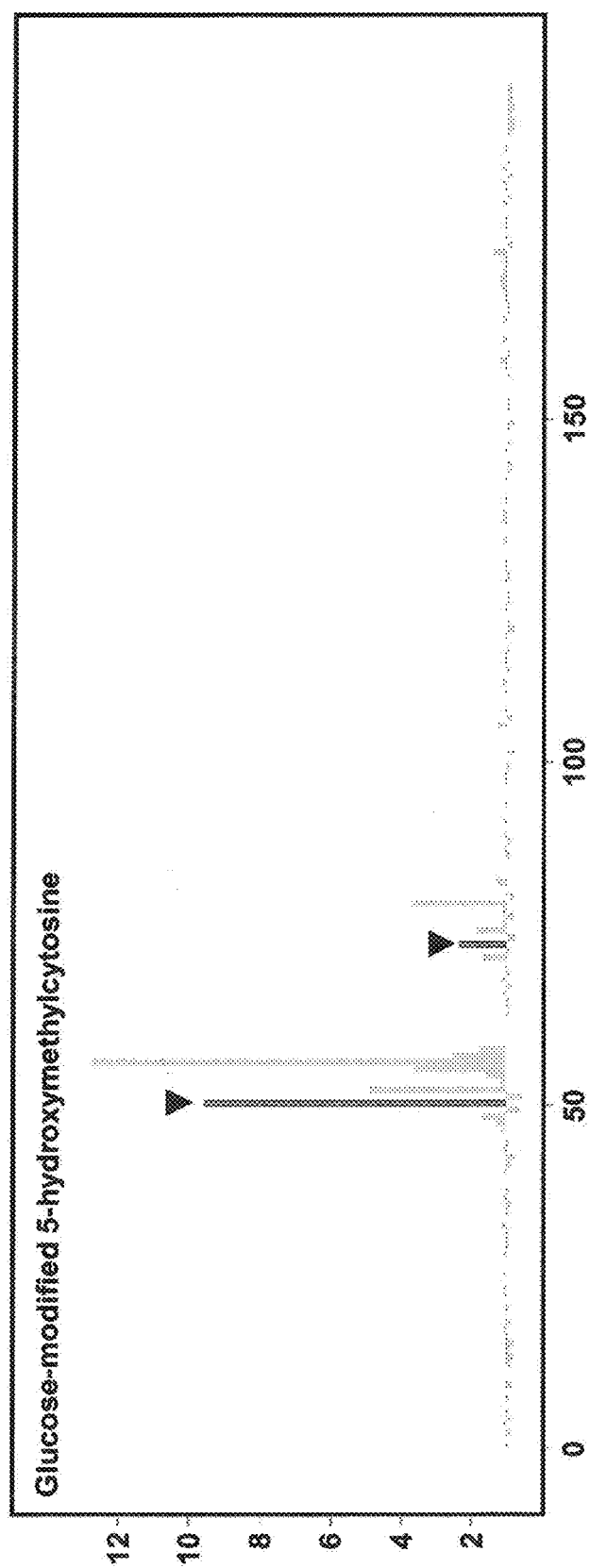
FIG. 11 provides a graph plotting IPD ratio against template position for a template deoxyribonucleic acid comprising glucose-modified 5-hydroxymethylcytosine.

Glucose-modified 5-hydroxymethylcytosine was also tested and shown to have an effect on IPD over a range of several bases upstream and downstream of the position of the glucose-modified 5-hydroxymethylcytosine. Closed, circular single-stranded templates were constructed containing a synthetic template containing two hmC residues in a duplex region flanked by single stranded linkers. Two micrograms of this template was labeled with a glucose moiety using T4 phage β-glucosyltransferase (New England Biolabs, Inc.). The samples were incubated at 37° C. for 60 minutes in the presence of 40 μM UDP-glucose following the manufacturer's recommendation. The resulting samples were cleaned up using a QIAGEN PCR Purification column and sequenced using previously described methods (Flusberg, et al. (2010) Nature Methods 7:461-465). An increase in IPD was observed at some positions in the presence of glucose-modified 5-hydroxymethylcytosine relative to the same positions in the absence of glucose-modified 5-hydroxymethylcytosine. FIG. 11 provides a plot depicting the ratio of the average IPD in the glucose-modified template to the average IPD in the unmodified template, plotted versus DNA template position. The two templates are identical except for the glucose-modified hydroxymethylcytosines in the modified template, which are indicated by arrowheads in FIG. 11. Average IPD ratios for glucose-modified hydroxymethylcytosine increased by as much as five-fold relative to detection of unmodified hydroxymethylcytosine (FIG. 9.)

Detection of Modified Bases in RNA Templates

Figure 12:
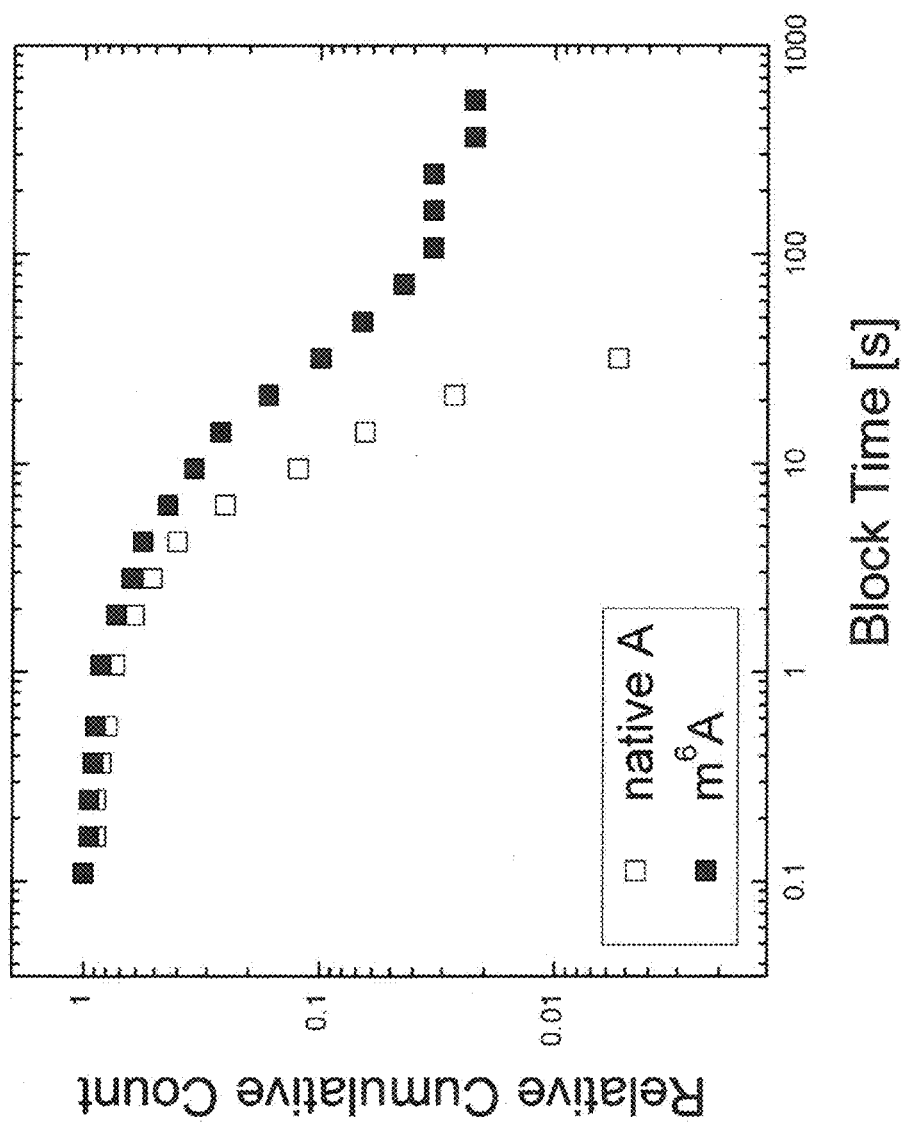
FIG. 12 provides a graph plotting block times for a template ribonucleic acid comprising $N^6$-methyladenosine and a template ribonucleic acid lacking $N^6$-methyladenosine.
Figure 13:
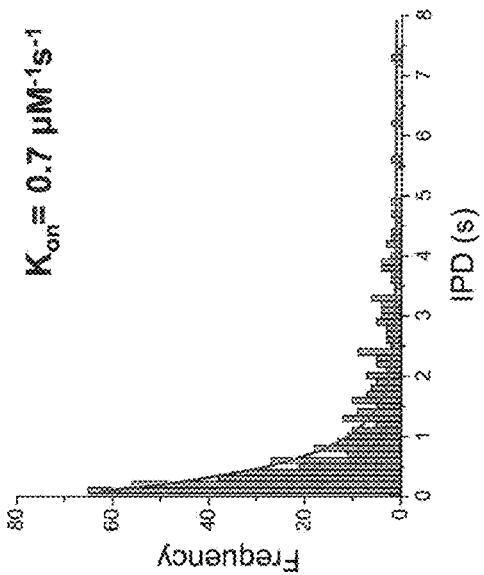
FIG. 13 provides graphs plotting IPDs in the presence and absence of $N^6$-methyladenosine modifications in RNA templates.
Figure 13:
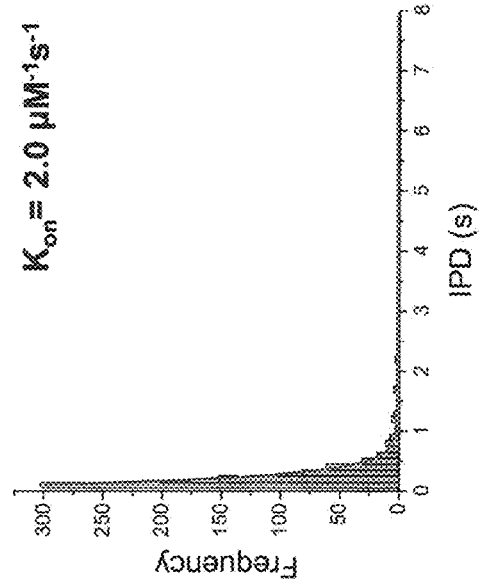

As noted elsewhere herein, the methods described herein can also be used for detection of modified nucleotides in RNA templates during template-dependent RNA sequencing. N$^6$-methyladenosine is a common post-translational modification of cellular and viral RNAs. RNA templates containing N$^6$-methyladenosine modifications at defined positions were produced by solid-phase nucleic acid synthesis. In addition, control RNA templates with identical sequences were synthesized without the above-mentioned modification. All RNA oligomers were hybridized to a complementary DNA primer that had been previously biotinylated at its 5'-end. Each DNA primer-RNA template hybrid was then immobilized via a biotin-streptavidin linkage in a ZMW. Single-molecule real-time RNA sequencing (as described in U.S. patent application Ser. No. 12/767,673, filed Apr. 26, 2010, and incorporated herein by reference in its entirety for all purposes) was initiated by the addition of reverse transcriptase under the following reaction conditions: 50 mM Tris pH 8.25, 10 mM KCl, 5 mM DDT, 0.1 mM CaCl$_2$, 2.5 mM MgCl$_2$, and 0.05 mM EGTA at 25° C. The kinetics of incorporation of complementary bases across from the modified site was evaluated and compared to the same sequence context lacking the modification. In these RNA sequencing reactions, base incorporations are detected as a combination of pulses of cognate sampling and incorporation. A "block" is defined as part of a sequencing trace containing pulses of the same base, indicating at least one of that base was incorporated into the nascent strand. "Block time" is defined as the time from the start of the first pulse of a block to the end of the last pulse of that block. FIG. 12 provides a plot depicting the relative cumulative count of events relative to observed block time in the N$^6$-methyladenosine modified template (filled squares) and the unmodified template (open squares). This plot clearly shows that the N$^6$-methyladenosine bases generally exhibit substantially longer block times than do the unmodified adenosine bases, and they can be distinguished from one another during single-molecule, real-time RNA sequencing. Further, the pulses within each block are characterized by standard parameters, including interpulse duration. For example, the values for IPD are sensitive to the presence of N$^6$-methyladenosine modifications, e.g., the distances between individual pulses increase in the presence of this modification. These increased IPDs are reflected in a higher K$_{off}$ obtained from the distributions of IPDs shown in FIG. 13.

Detection of 5-MeC Enhanced by Conversion to 5-caC

Figure 14:
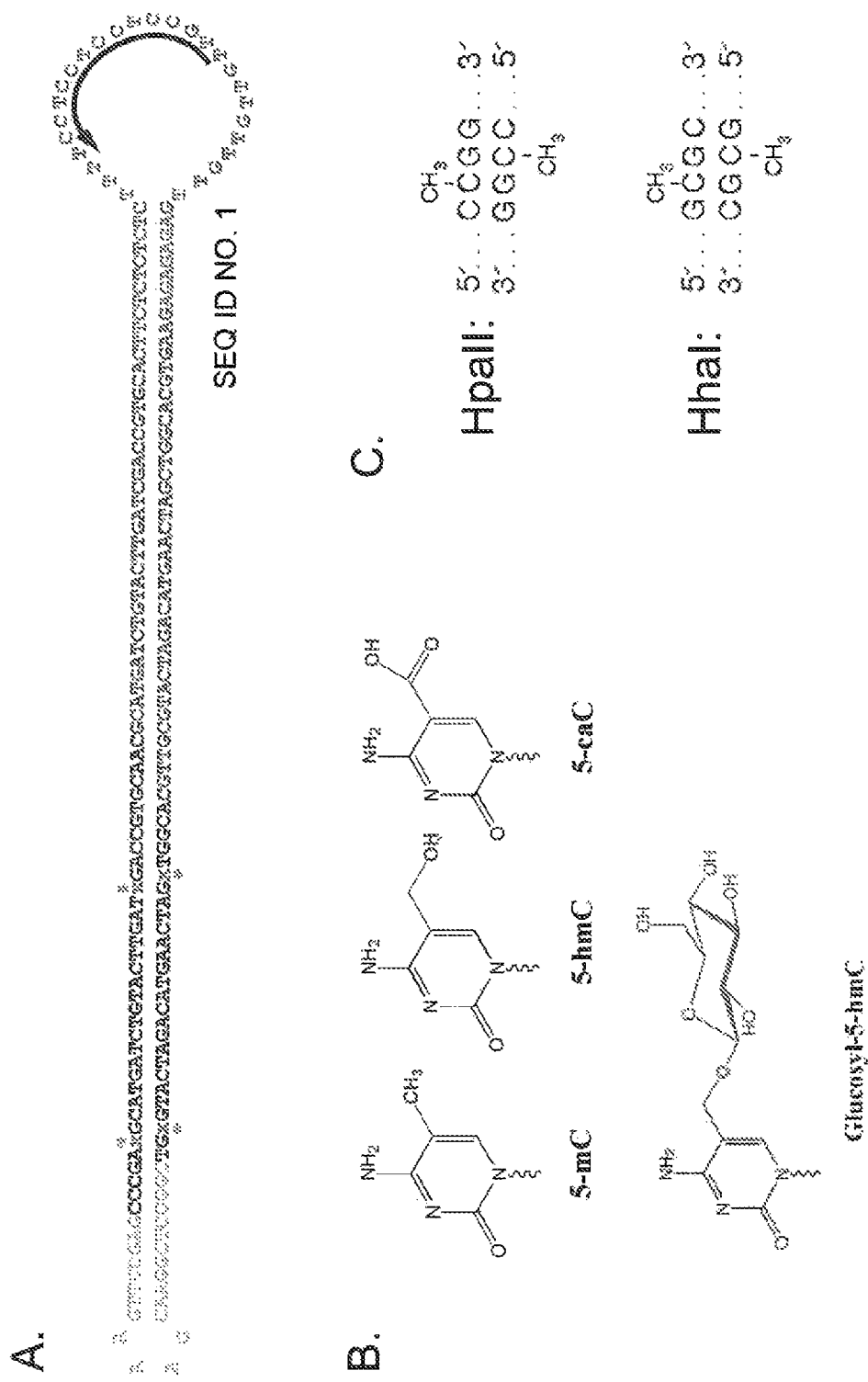
FIG. 14A shows a sequencing template containing 5-MeC nucleotides.
FIG. 14B provides chemical structures for several modified bases.
FIG. 14C illustrates two different motifs that were subject to the modifications.

Closed, circular, single-stranded sequencing templates were constructed containing 5-MeC nucleotides (FIG. 14A) were subjected to treatment to convert the 5-MeC to either 5-hmC or 5-caC. Both hemi-methylated and fully-methylated sequencing templates were constructed. Further, two different motifs were subject to the modifications, as shown in FIG. 14C. The conversion to 5-hmC used mTET1 (mouse enzyme) to first convert 5-MeC to 5-hmC, which was then subjected to glucosylation to generate glucosyl-5-hmC. The conversion to 5-caC also used mTET1 but did not involve glucosylation. Rather, mTET1 converted the 5-MeC to 5-hmC, and then converted the 5-hmC to 5-caC. The chemical structures of these modified bases are depicted in FIG. 14B.

Figure 15:
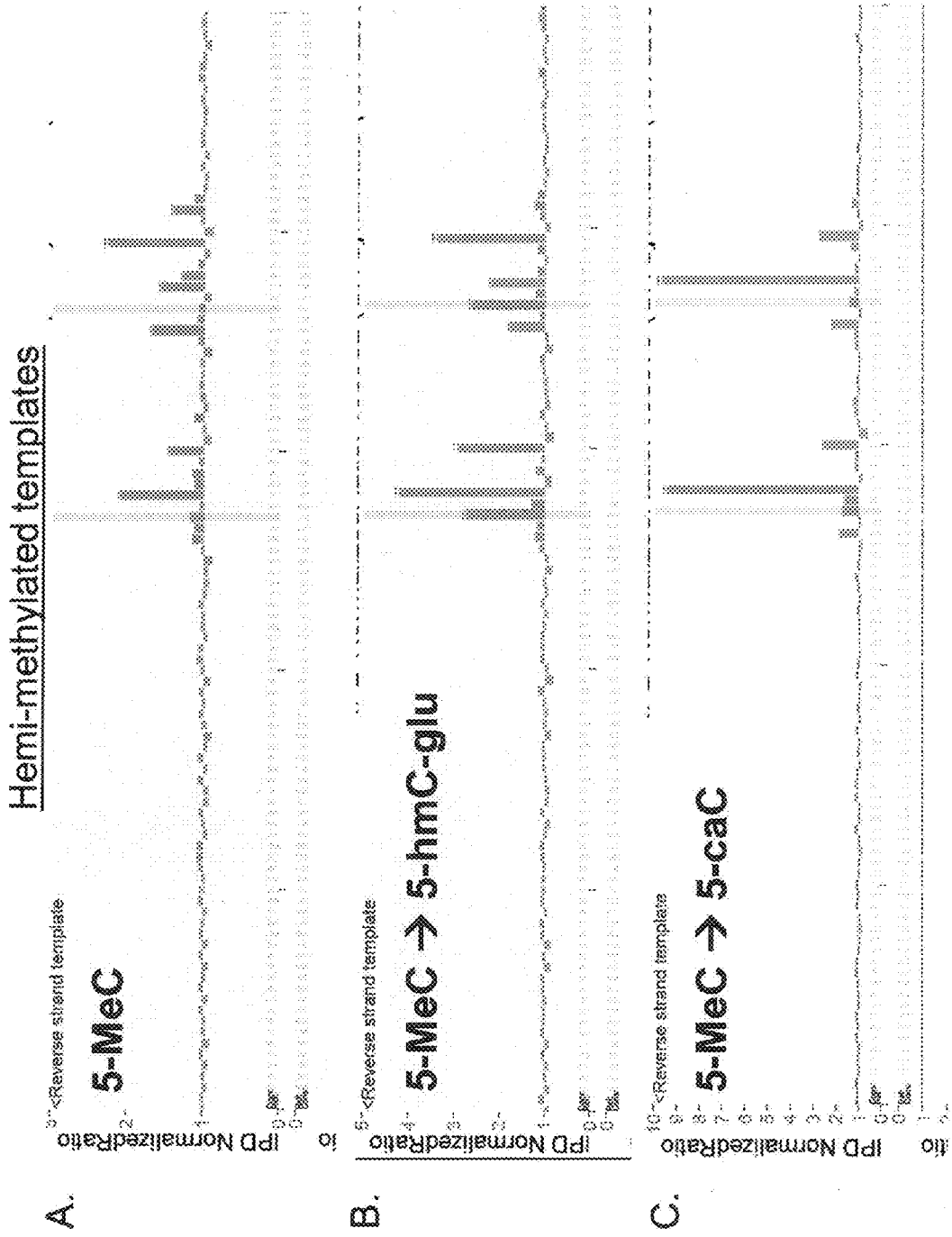
FIGS. 15A, 15B, and 15C provide graphical illustrations of normalized IPD ratios for hemi-methylated templates having 5-MeC, 5-hmC-glu, and 5-caC base modifications, respectively.
Figure 16:
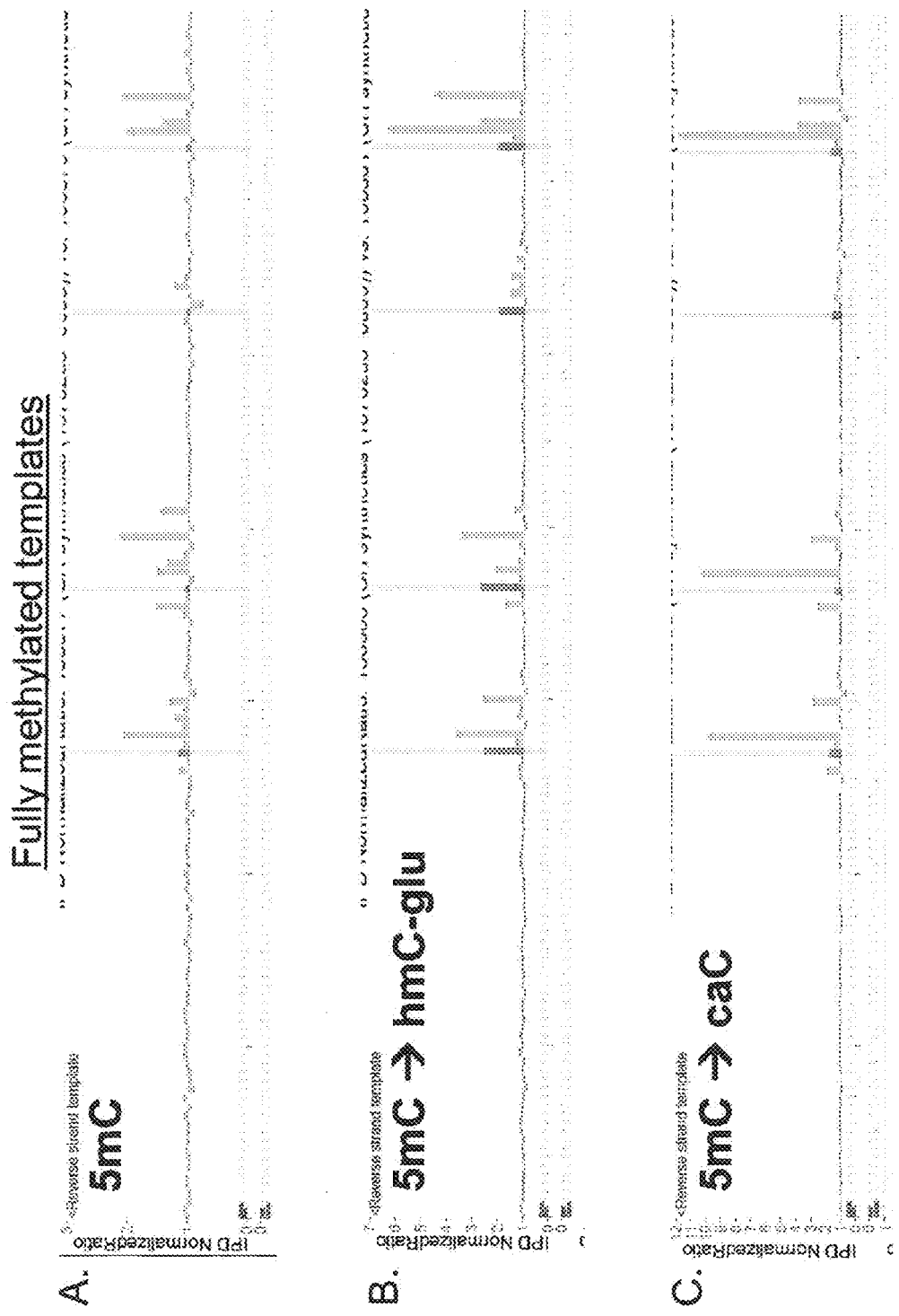
FIGS. 16A, 16B, and 16C provide graphical illustrations of normalized IPD ratios for fully methylated templates having 5-MeC, 5-hmC-glu, and 5-caC base modifications, respectively.
Figure 17:
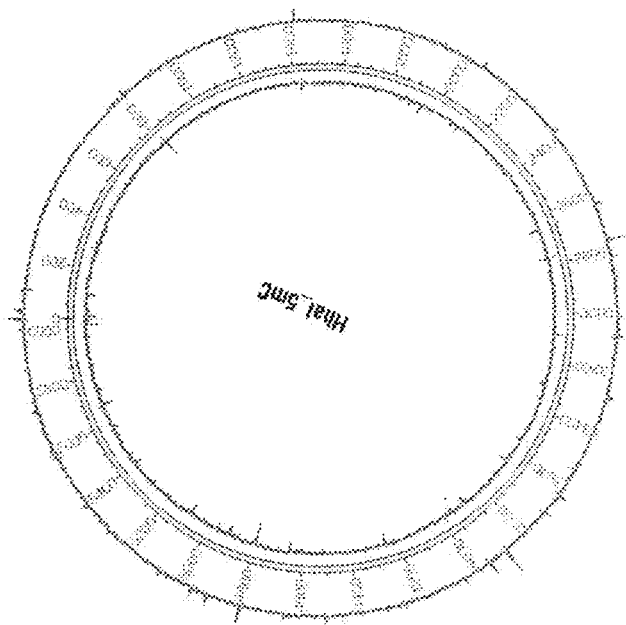
FIG. 17 provides circos plots for templates having 5-MeC base modifications at the HpaII methyltransferase recognition site (A) or the HhaI methyltransferase recognition site (B).
Figure 17:
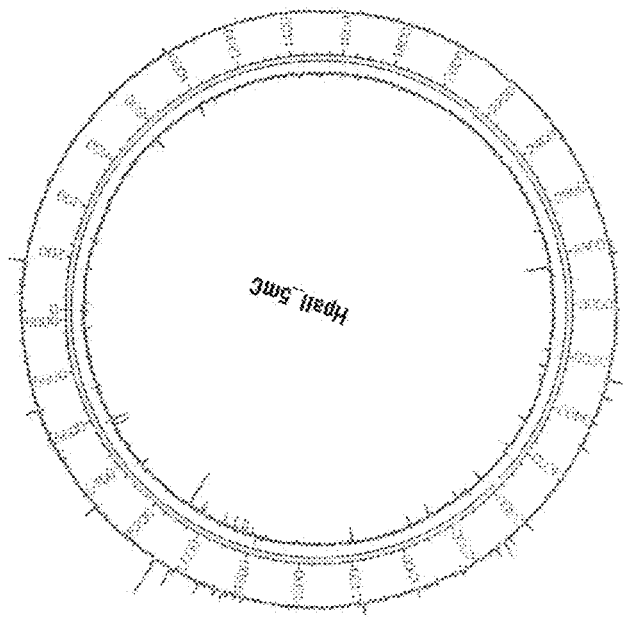
Figure 18:
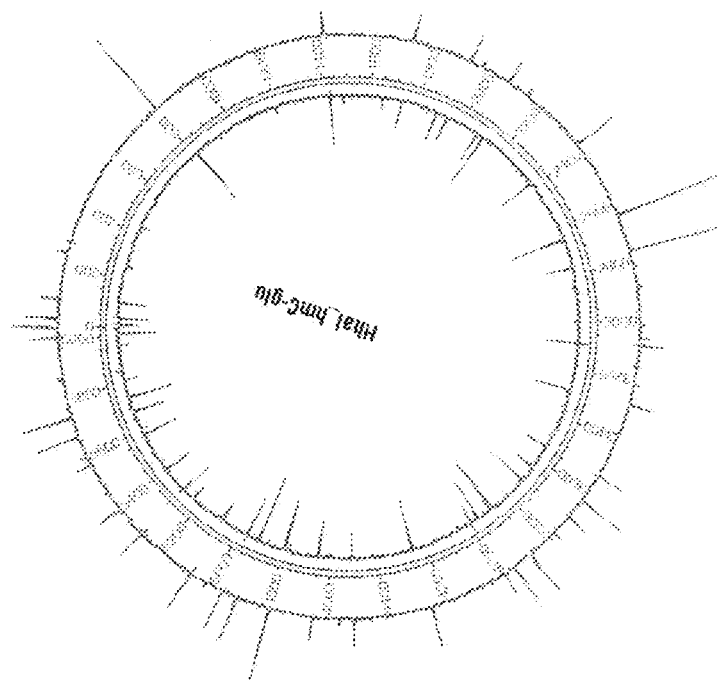
FIG. 18 provides circos plots for templates having 5-hmC-glu base modifications at the HpaII methyltransferase recognition site (A) or the HhaI methyltransferase recognition site (B).
Figure 18:
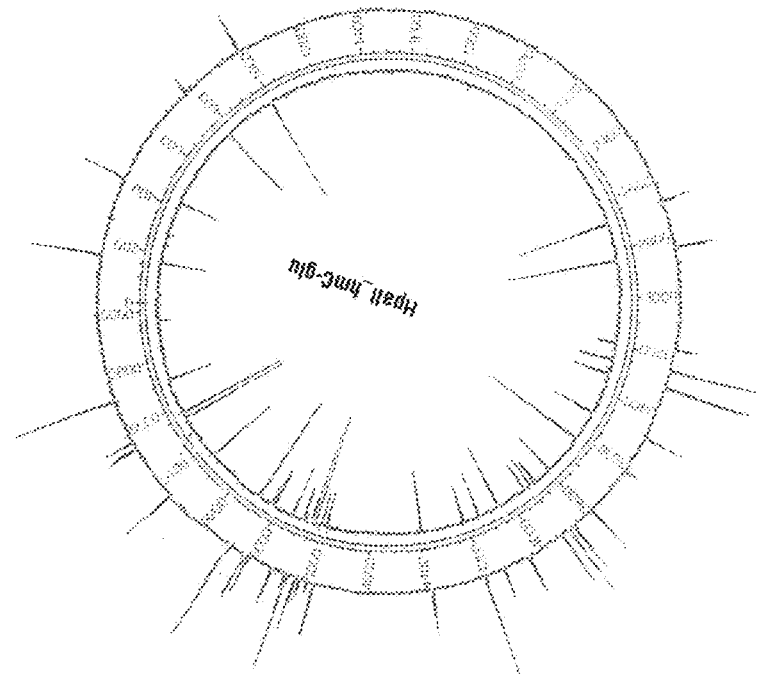
Figure 19:
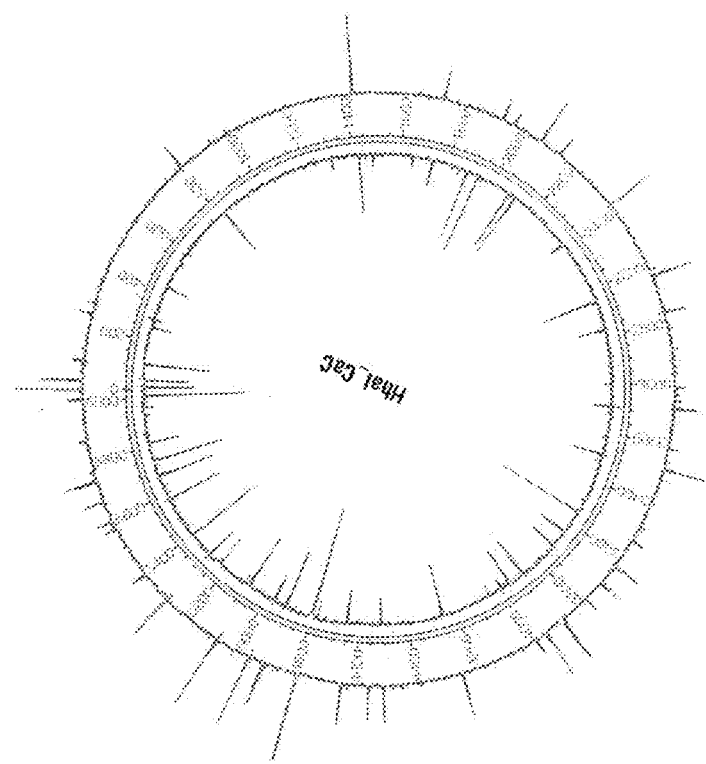
FIG. 19 provides circos plots for templates having 5-caC base modifications at the HpaII methyltransferase recognition site (A) or the HhaI methyltransferase recognition site (B).
Figure 19:
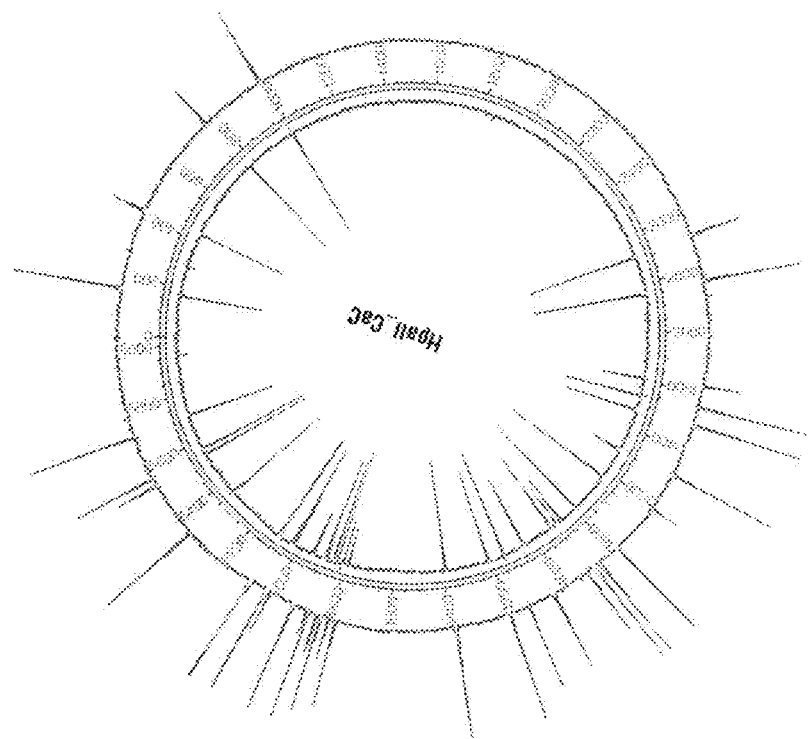

The 5-MeC, glucose-modified 5-hmC, and the 5-caC were shown to have an effect on IPD over a polynucleotide region of the nucleic acid template during template-directed nascent strand synthesis (previously described in Flusberg, et al. (2010) Nature Methods 7:461-465). The results from sequencing both the hemi-methylated templates (FIG. 15) and the fully methylated templates (FIG. 16) show increases in IPD for all modifications, with the 5-caC modifications producing the largest increase in IPD, and the glucose-modified 5-hmC showing the second-greatest increase in IPD. FIGS. 17-19 show results from the two different sequence contexts for 5-MeC, glucose-modified 5-hmC ("5-hmC-glu"), and 5-caC, respectively, with the scale of the observed IPD the same for each figure. Once again, the 5-caC caused the largest increase in IPD and the glucose-modified 5-hmC caused the second-largest increase in IPD during template-directed nascent strand synthesis. The increases in IPD were not limited to the specific base at which the modification occurred, but were also observed in flanking positions for all the different modifications, with the pattern of flanking positions that were affected being different for each modification tested.

Varying Signatures for Different Cytosine Modifications

To determine the kinetic signatures for the four naturally occurring forms of cytosine with a modification on the $5^{th}$ carbon atom, synthetic SMRTbell™ templates made from oligonucleotides with modified cytosines at specific template positions were designed and constructed as previously described through ligation of several synthetic oligonucleotides (Clark, et al. (2011) Genome Integrity 2:10). For plasmid and genomic DNA samples, an aliquot of approximately 25 ng of DNA was subjected to whole-genome amplification (WGA) using the REPLI-g® Midi Kit (Qiagen, Valencia, Calif.). WGA and native DNA was sheared to an average size of ~500 base pairs via adaptive focused acoustics (Covaris, Woburn, Mass.). SMRTbell™ template sequencing libraries were prepared as previously described (Clark, et al. (2012) Nucleic Acids Res. 40:e29; and Travers, et al. (2010) Nucleic Acids Res. 38:e 159). SMRTbell™ libraries made from whole-genome-amplified pCRBlunt-6K plasmid were in vitro methylated using the HpaII methyltransferase (recognition sequence: 5'-$C^{5m}$CGG-3', from New England Biolabs, Ipswich, Mass.) per the manufacturer's instructions. Complete methylation was assessed by modifying lambda DNA in parallel and subjecting to methylation-sensitive restriction using the HpaII restriction enzyme (New England Biolabs).

Figure 20:
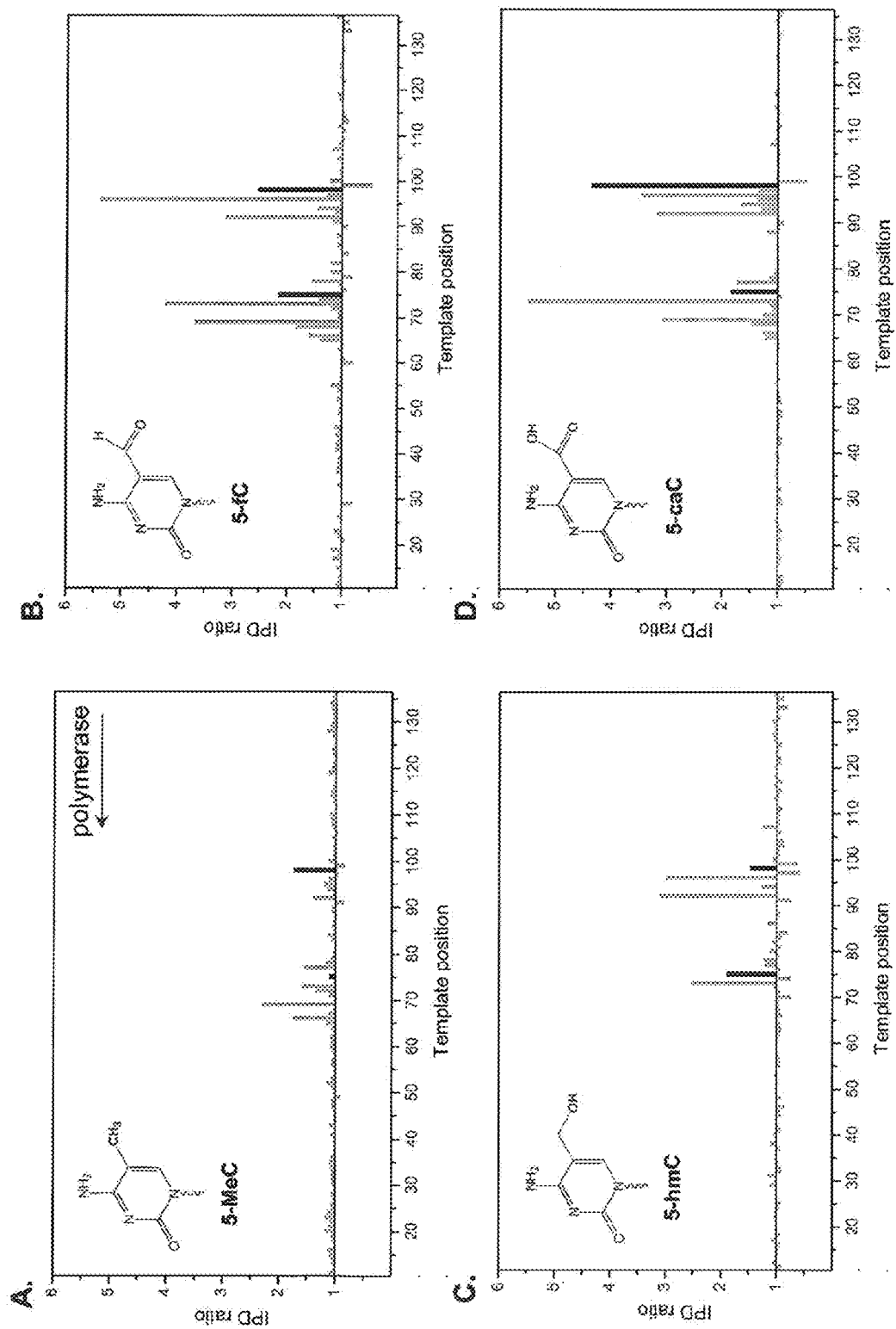
FIG. 20 provides graphical illustrations of kinetic signals from SMRT® Sequencing of four epigenetic markers: 5-MeC (FIG. 20A), 5-fC (FIG. 20B), 5-hmC (FIG. 20C), and 5-caC (FIG. 20D).

Four modified synthetic SMRTbell™ templates were made from synthetic oligonucleotides, each containing two 5-MeC, 5-hmC, 5-fC, or 5-caC modifications. The polymerase dynamics of each was measured during SMRT® Sequencing by plotting the ratio of interpulse durations (IPDs) for each template position against a control template of identical sequence but lacking the modifications. The kinetic signatures for each cytosine modification type are shown in FIG. 20 as ratios of the average IPD value at each template position of the modified template relative to the unmodified control. The template is shown in the 5' to 3' direction from left to right, the polymerase movement is right to left across the template as indicated by the arrow, and positions of the modified bases are highlighted as black bars. As observed previously (Flusberg, et al. (2010) Nat. Methods 7:461-465), the kinetic signature for 5-MeC is distinct from the background, but the magnitudes of the IPD ratios are small, translating to relatively high sequencing coverage for detection of the modified positions with high confidence. Furthermore, the kinetic signature is spread out over multiple positions on the DNA template, likely due to effects of base modifications on the polymerization rate extending across the entire footprint of the polymerase (Kamtekar, et al. (2004) Molecular Cell 16:609-618).

As the size of the chemical structure of the modification increases, the magnitude of the kinetic signature also increases. The IPD ratio peaks range from ~2-fold for 5-MeC (FIG. 20A) and ~3-fold to higher than 5-fold for 5-fC (FIG. 20B) and 5-caC (FIG. 20D). The IPD ratio peaks for 5-hmC were more modest, ranging from about 2- to 3-fold (FIG. 20C). For each modification type, an extended signature consisting of multiple IPD ratio peaks was observed, with the most prominent signals at positions 0, +2, and +6 relative to the polymerase movement, with 0 being the position of the modification in the template. In most instances investigated here, the +2 peak was the most pronounced. As previously observed (Clark, et al. (2012) Nucleic Acids Res. 40:e29; and Flusberg, et al. (2010) Nat. Methods 7:461-465), the kinetic signatures for a given modification varied slightly depending on the surrounding sequence context. These differences in the pattern and magnitudes of the kinetic signatures for each of the four different modifications are a parameter that can be used to discriminate between different modifications on the same DNA template. To further explore the effects of local sequence context on the kinetic signatures of 5-MeC and 5-caC, a synthetic SMRTbell™ template that contained a modified base in a 5'-CG-3' sequence context, surrounded by two random bases on each side, was used. As observed previously (Flusberg, et al. (2010) Nat. Methods 7:461-465; and Clark, et al. (2011) Genome Integrity 2:10), the magnitude and position of the kinetic signals for both 5-MeC and 5-caC are dependent upon the surrounding sequence context. The conversion of 5-MeC to 5-caC enhances the magnitude of the IPD ratio at each position where ratios above 1.0 are observed for 5-MeC, i.e. positions 0, +2, and +6, and brings out an additional detectable signal at the −2 position for some sequence contexts. Tet conversion enhances the kinetic signals relatively evenly across all sequence contexts which is apparent from the good preservation of the overall sequence context profiles.

Enhanced Detection of 5-MeC Following Conversion to 5-caC by mTet1

The large kinetic signature of 5-caC significantly improved the ability to detect 5-MeC in SMRT® sequencing following conversion of 5-MeC to 5-caC. The TET family of proteins has been shown to convert 5-MeC to 5-caC in mammalian genomes (He, et al. (2011) Science 333:1303-1307; and Ito, et al. (2011) Science 333:1300-1303). This conversion can be over 97% for sequencing purposes and does not exhibit significant sequence context bias (Yu, et al. (2012) Cell 149: 1368-1380). The enhancement of detection of 5-MeC following Tet1-mediated oxidation to 5-caC on in vitro methylated DNA templates was tested. Briefly, a ~6 kb plasmid was generated by inserting a lambda DNA fragment into the pCR-Blunt vector (Life Technologies, Carlsbad, Calif.) and subjected it to whole genome amplification (WGA) to erase all modifications. Then, a ~500 base pair (bp) randomly sheared shotgun SMRTbell™ template library was generated from the WGA material, followed by in vitro methylation using the HpaII methyltransferase that modifies the internal cytosine in 5'-CCGG-3' sequence contexts. Considering both the forward and reverse DNA strands, the plasmid sequence contains 70 instances of the 5'-CCGG-3' sequence motif.

Methylated positions within the SMRTbell™ templates were converted to 5-caC by treatment with the Tet1 enzyme. Briefly, the 5-MeC modifications in SMRTbell template libraries were converted to 5-caC using the 5-MeC mouse mTet1 Oxidation Kit from Wisegene (Chicago, Ill.) per the manufacturer's instructions. Approximately 500 ng of SMRTbell™ templates were treated with the mTet1 enzyme at 37° C. for 60 minutes followed by proteinase K treatment at 50° C. for 60 minutes. Converted SMRTbell™ templates were purified using Micro Bio-Spin® 30 Columns (BioRad, Hercules, Calif.) with additional purification and concentration using MinElute® PCR Purification Columns (Qiagen, Valencia, Calif.). In vitro methylated (5-MeC), Tet1-converted (5-caC), and WGA control (no modification) libraries were then subjected to SMRT® Sequencing.

Figure 21:
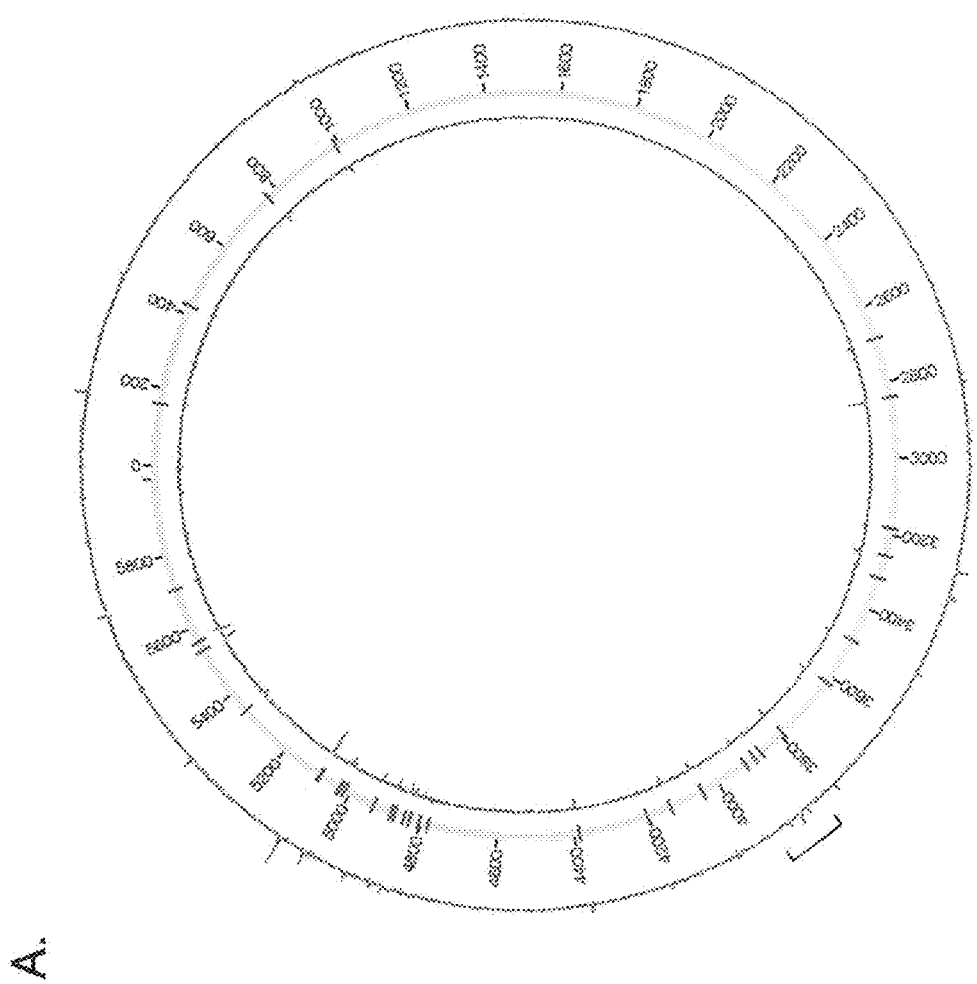
FIG. 21 provides graphical illustrations of enhanced detection of 5-MeC through Tet1 oxidation using in vitro methylated plasmid samples. Results for an untreated sample are shown in FIGS. 21A (circos plot) and 21C (graph of IPD ratios). Results for an Tet1-treated sample are shown in FIGS. 21B (circus plot) and 21D (graph of IPD ratios).

FIG. 21 illustrates the enhanced detection of 5-MeC through mTet1 oxidation using the in vitro methylated plasmid samples. FIGS. 21A and 21B are a circos plots showing the plasmid-wide view of IPD ratio data for the untreated and the mTet1-converted templates, respectively, relative to the unmodified control. The outer circles denote the forward strands, and the inner circles denote the reverse strands. The tick marks along the middle circles denote all positions of the targeted M. HpaII in vitro methylated sequence motif of 5'-C CGG-3' (methylated base underlined). The bracket in FIG. 21A denotes a section of the plasmid that is shown at base resolution in FIG. 21C; and the bracket in FIG. 21B denotes a section of the plasmid that is shown at base resolution in FIG. 21D. The section shown in FIGS. 21C and 21D contains three instances of the methylated motif (grey boxes), and the methylated positions are indicated with black bars. The IPD ratios for the 5-MeC modified templates are visible as small excursions from the background (FIGS. 21A, C). Following mTet1-mediated oxidation to 5-caC, the kinetic signature was enhanced by an average of ~4.6-fold, making all 35 instances of the methyltransferase recognition motif recognizable as large excursions in the IPD ratio (FIGS. 21B, D). The primary IPD ratio peaks for the 5-caC sample again fell at the +2 position relative to the modification, consistent with the results obtained from the synthetically derived samples. Similar results were obtained with synthetic SMRTbell™ templates that were made with oligonucleotides containing 5-MeC modifications and subjected to conversion by mTet1 (data not shown).

Genome-Wide Analysis of 5-MeC DNA Methyltransferase Specificities in Bacterial Strains Most bacterial and archeal genomes contain DNA methyltransferases (MTases). Many of these MTases are paired with restriction endonucleases as part of a restriction-modification system that protects the organism from foreign DNA (Wilson, et al. (1991) Annual Review of Genetics 25:585-627). These MTases typically methylate a specific sequence context that blocks the activity of the restriction enzyme that recognizes the same site. The three most common types of methylation found in bacteria and archea are 6-mA, 4-mC, and 5-MeC. To test the ability of the mTet1-enhanced signal to detect 5-MeC in genomic DNA, two bacterial strains that are known to express a 5-MeC MTase (Roberts, et al. (2010) Nucleic Acids Res. 38:D234-236) were selected for analysis. Bacterial strains and/or genomic DNA from bacterial strains were purchased from the American Type Culture Collection (Manassas, Va.). The following strains were used in this study: *Escherichia coli* K12 MG1655, and *Bacillus halodurans* C-125 (JCM 9153).

*E. coli* K12 MG 1655 is a well-studied, common laboratory strain that is known to express three different methyltransferases. EcoKdam is a 6-mA MTase that modifies the adenosine in a 5'-GATC-3' sequence context (methylated base underlined). EcoKI is a type I MTase that modifies the sequence context 5'-GCAC(N6)GTT-3' and reverse complement 5'-AAC(N6)GTGC-3'. The 5-MeC MTase is EcoKdcm which modifies the internal cytosine in a 5'-CCWGG-3', where W is either an A or a T. SMRTbell™ templates were constructed from randomly sheared *E. coli* K12 MG1655 genomic DNA, a portion of which was sequenced in its native form and another portion that was subjected to the mTet1 treatment. Both samples were sequenced to approximately 150× per-DNA strand fold coverage.

Figure 22:
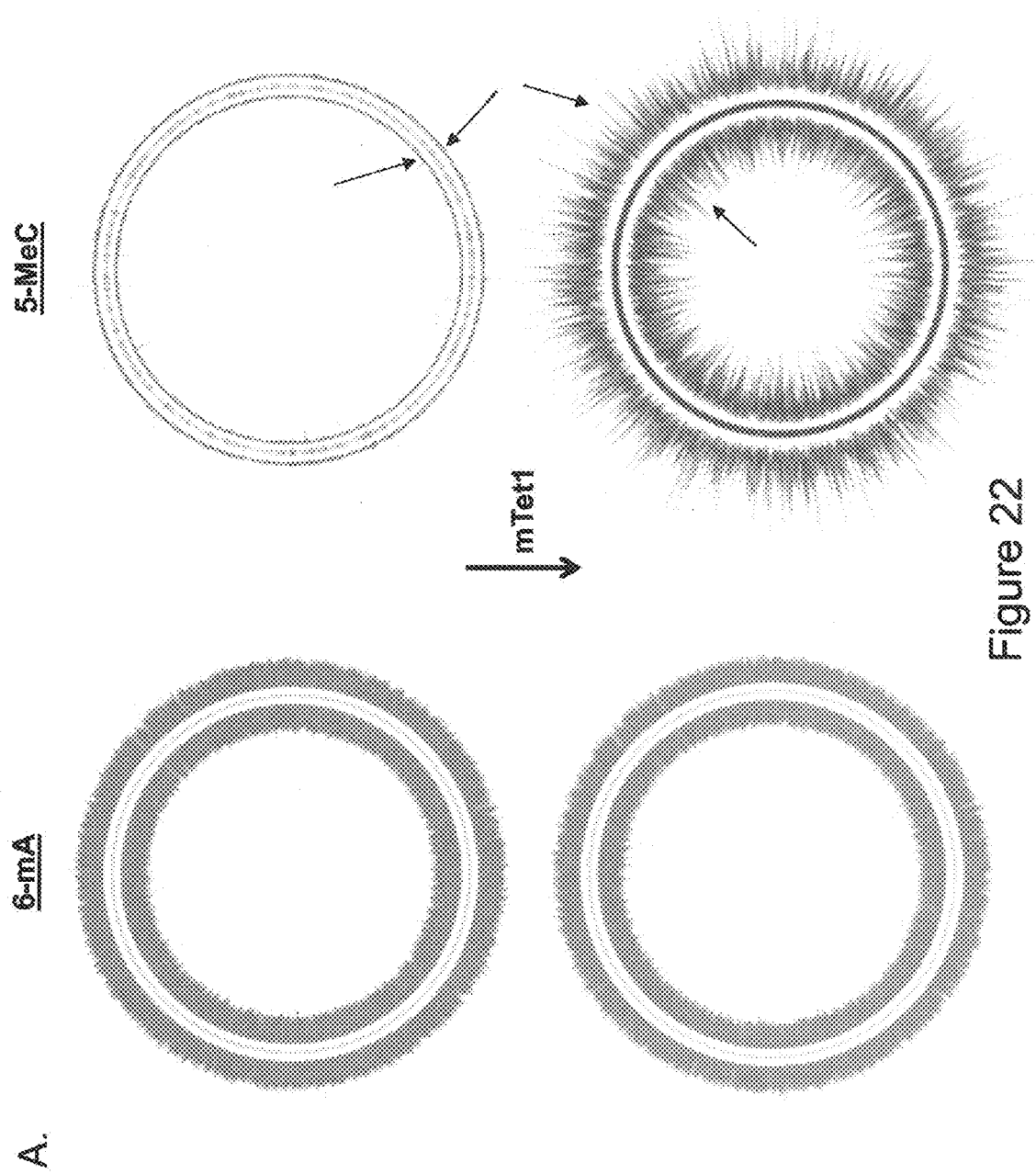
FIG. 22 provides graphical illustrations of genome-wide methyltransferase specificity in *E. coli* K12 MG1655.

An unbiased search was performed to identify sequence motifs that were enriched in proximity to genomic positions with large excursions from the expected IPD values. For the native sample the expected 5'-GATC-3' and the 5'-GC AC(N6)GTT-3'/5'-AAC(N6)GTGC-3' sequence motifs were identified, but low signal levels for the 5'-CCWGG-3' motif were observed. However, following the mTet1 conversion, the majority of 5'-CCWGG-3' motifs in the genome could be identified as modified. FIG. 22 compares IPD ratio data over the entire *E. coli* genome before and after mTet1 treatment. As expected, IPD ratio data for sites methylated with 6-mA did not change between the native (FIG. 22A, top, leftmost circos plot) and Tet1-converted (FIG. 22A, bottom, leftmost circos plot) samples. In contrast, IPD ratio data for the +2 position of the 5'-CCWGG-3' sites (lines indicated by arrows in rightmost circos plots of FIG. 22A) were significantly increased in the mTet1-treated sample (bottom) relative to the untreated sample (top), thereby improving detection of dcm-mediated methylated positions, with IPD ratio magnitudes now similar to 6-mA signals. The outer circles denote the forward strands, and the inner circles denote the reverse strands.

FIGS. 22B and 22C show base-resolution IPD ratio views of a section of the genome containing one target site for adenine methylation by dam (5'-GATC-3') and one target site for cytosine methylation by dcm (5'-CCWGG-3'). Kinetic score distributions for both on-target and off-target sequence motifs before and after mTet1 conversion for all +2 positions of 5'-CCWGG-3' in the genome are plotted in FIG. 22D. An orthogonal off-target motif (5'-GGWCC-3') is also shown; it was used to set a 1% false discovery rate threshold (dashed line) for tabulation of detected methylated positions (Table 1). The tick marks in the circos plots in FIG. 22A denote 5'-C CWGG-3' genomic positions detected as methylated using that threshold.

To estimate the degree of enhancement in 5-MeC detection by mTet1 treatment (Table 1), the $99^{th}$ percentile kinetic score of an off-target motif (5'-GGWCC-3') was selected as the threshold for calling a genomic position as methylated (FIG. 22D). Any kinetic score that was greater than this value was considered modified. In the native sample, only 455 (1.9%) of all genomic 5'-CCWGG-3' positions were detected above this background value. Upon conversion of 5-MeC to 5-caC in the mTet1-treated sample, 22,913 (95.2%) genomic 5'-C CWGG-3' positions were detected as methylated. The off-target site was unaffected by the mTet1 treatment, highlighting the specificity of the mTet1 conversion to methylated DNA sites.

TABLE 1

Detection of 5-MeC in native vs. mTet1-enhanced SMRT® Sequencing for the bacterial genomes. Unassigned is the percentage of genomic positions that have kinetic scores above the cutoff but are not in a methylated motif or a secondary peak.

| Sample | | Methylation motif | # in genome | # detected | % detected | % unassigned |
|---|---|---|---|---|---|---|
| E. coli | native | C$^m$CWGG | 24,079 | 455 | 1.9% | 0.4% |
| MG1655 | Tet1 | C$^m$CWGG | 24,079 | 22,913 | 95.2% | 0.3% |
| B. halodurans | native | GG$^m$CC | 15,207 | 660 | 4.3% | 0.6% |
| C-125 | Tet1 | GG$^m$CC | 15,207 | 11,663 | 76.7% | 0.5% |

The same procedure was performed for *B. halodurans* C-125, a bacteriocin producing soil bacterium. The *B. halodurans* genome is predicted to have three different methyltransferases (Roberts, et al. (2010) Nucleic Acids Res. 38:D234-236), including one MTase that has the hallmarks of a 5-MeC modifying enzyme. However, unlike for the *E. coli* sample, the exact sequence motifs and positions of the modifications are not known. SMRT® sequencing provided the ability to identify two methylated sequence motifs: 5'-GCATC-3'/5'-GATGC-3' and 5'-GGCC-3'.

Figure 23:
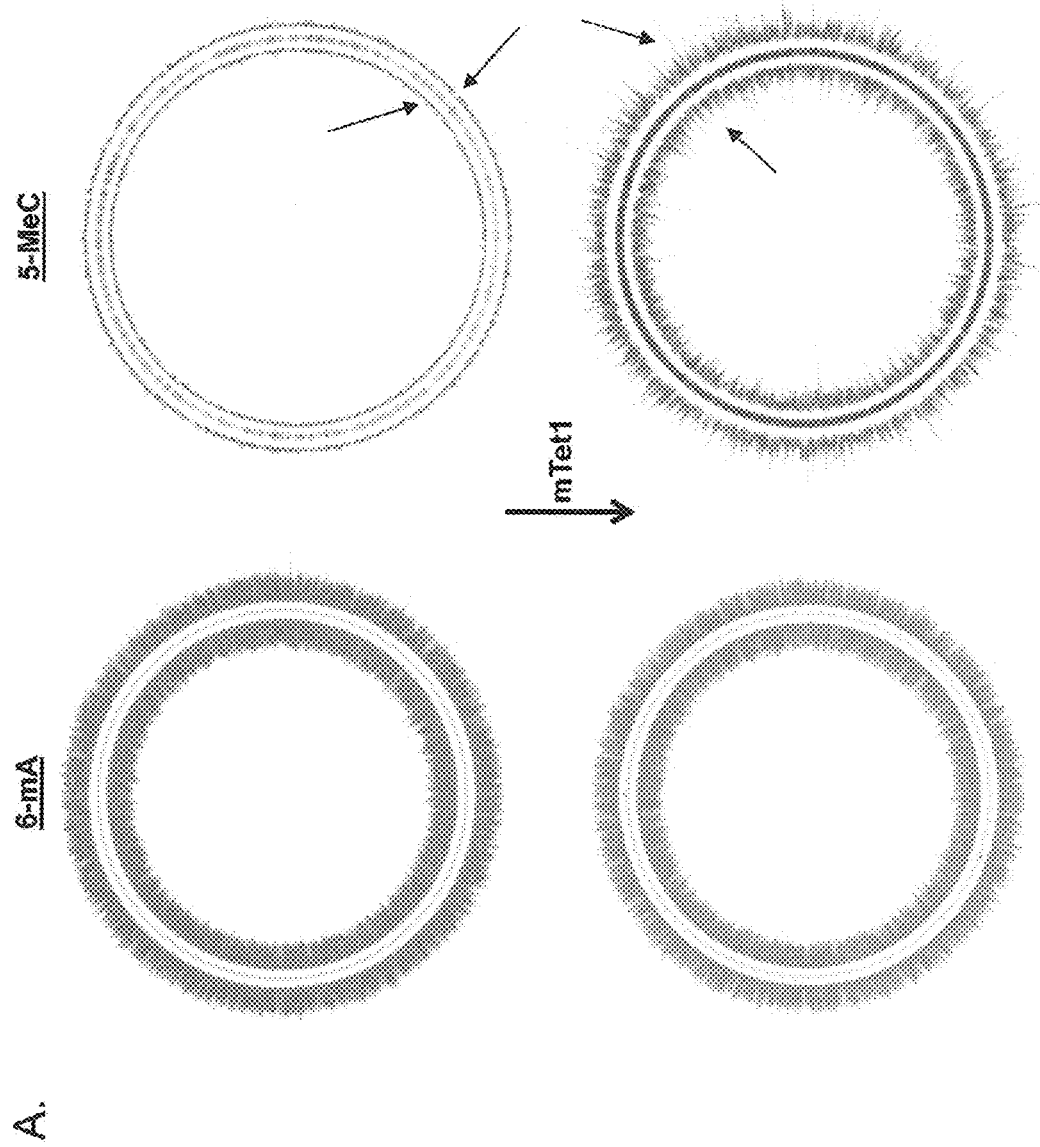
FIG. 23 provides graphical illustrations of genome-wide methyltransferase specificity in *B. halodurans*.

The circos plots in FIG. 23A show the genome-wide view of IPD ratios before and after mTet1 treatment, with the outer circles denoting the forward strands, and the inner circles denoting the reverse strands. As for the *E. coli* sample, IPD ratio data for sites methylated with 6-mA did not change between the native (FIG. 23A, top, leftmost circos plot) and Tet1-converted (FIG. 23A, bottom, leftmost circos plot) samples. The first motif (5'-GCATC-3'/5'-GATGC-3') had high IPD ratio values on the A position on both forward and reverse strands, which is indicative of 6-mA, and this signal was present in both native and mTet1-treated samples. In contrast, IPD ratio data for the +2 position of the 5'-GGCC-3' sites (lines indicated by arrows in rightmost circos plots of FIG. 23A) was significantly stronger in the mTet1-treated sample (bottom) relative to the untreated sample (top), with the strongest peak on the first G in the motif (FIG. 23C). Using the +2 pattern of the converted 5-caC signature, the most likely modified base is the inner C in the 5'-GGCC-3' motif. We detected 4.3% of 5'-GGCC-3' motifs without mTet1-treatment, increasing to 76.7% following the enhancement of the 5-MeC signal by mTet1 conversion (Table 1). Kinetic score distributions are shown in FIG. 23D for both on-target and off-target sequence motifs before and after mTet1 conversion for all +2 positions of 5'-GGCC-3' in the genome. An orthogonal off-target motif (5'-CCGG-3') is also shown. This motif was used to set a 1% false discovery rate threshold (dashed line) for tabulation of detected methylated positions (Table 1). The tick marks in the circos plots in FIG. 23A denote 5'-GGCC-3' genomic positions detected as methylated using that threshold.

Sequencing and Data Acquisition

SMRTbell™ templates were subjected to standard SMRT® sequencing, as described previously (Eid, et al. (2009) Science 323:133-138; and Korlach, et al. (2010) Methods Enzymology 472:431-455). Reads were processed and mapped to the respective reference sequences using the BLASR mapper (http://www[dot]pacbiodevnet[dot]com/SMRT-Analysis/Algorithms/BLASR) and Pacific Biosciences' SMRT® Analysis pipeline (http://www[dot]pacbiodevnet[dot]com/SMRT-Analysis/Software/SMRT-Pipe) using the standard mapping protocol. IPDs were measured as previously described (Flusberg, et al. (2010) Nature Methods 7(6):461-465) and processed as described (Clark, et al. (2012) Nucleic Acids Res. 40:e29) for all pulses aligned to each position in the reference sequence.

For the bacterial methylome analysis (Murray, et al. (2012) Nucleic Acids Res. 40(22):11450-11462), Pacific Biosciences' SMRT® Portal analysis platform v. 1.3.1 was used. This platform uses an in silico kinetic reference, and a t-test based detection of modified base positions (details are available at http://www[dot]pacb[dot]com/pdf/TN_Detecting_DNA_Base_Modifications.pdf). The following Genbank reference sequences were used: U00096.2 for *E. coli* K-12 MG1655 and BA000004.3 for *B. halodurans* C-125. Methyltransferase target sequence motifs were identified by selecting the top one thousand kinetic hits and subjecting a +/−20 base window around the detected base to MEME-ChIP (Machanick, et al. (2011) Bioinformatics 27:1696-1697), and compared to the predictions in REBASE (Roberts, et al. (2010) Nucleic Acids Res. 38:D234-236). To estimate the enhancement of detection of methylated 5-MeC positions (Table 1), an orthogonal off-target motif of similar sequence content was first selected, and the kinetic score representing the 99$^{th}$ percentile of all genomic positions of that motif (5'-GGWCC-3' for *E. coli* (score threshold=35.6); 5'-CCGG-3' for *B. halodurans* (30.4)) was calculated. This 1% false positive detection threshold was then used for determining the number of genomic positions of the on-target methylation sites detected as methylated (FIGS. 22D and 23D; Table 1). IPD ratio plots were visualized using Circos software (Krzywinski, et al. (2009) Genome Research 19:1639-1345).

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications, and publications are referenced. To the extent not already expressly incorporated herein, all published references and patent documents referred to in this disclosure are incorporated herein by reference in their entirety for all purposes.

What is claimed is:

1. A method for identifying a 5-methylcytosine (5-MeC) in a template nucleic acid, the method comprising:
   a) providing a template nucleic acid comprising the 5-MeC;
   b) converting the 5-MeC into a modified base by treating the template nucleic acid with a Tet protein, wherein the modified base is selected from 5-carboxylcytosine (5-caC) and 5-formylcytosine (5-fC), thereby generating a modified template nucleic acid;
   c) sequencing the modified template nucleic acid in the presence of fluorescently labeled nucleotides in a single-molecule sequencing reaction;
   d) monitoring said single-molecule sequencing reaction, wherein said monitoring comprises measuring inter-pulse duration, which is the length of time between fluorescent pulses, and pulse width, which is the width of fluorescent pulses, during said single-molecule sequencing reaction, and the fluorescent pulses are generated during incorporation of single bases of said fluorescently labeled nucleotides into a nascent nucleic acid strand synthesized during said single molecule sequencing reaction; and e) identifying the 5-methylcytosine (5-MeC) in the template nucleic acid by detecting a kinetic change during said sequencing the modified template nucleic acid, wherein said kinetic change is a kinetic change relative to a control template nucleic acid and comprises at least one change selected from the group consisting of a change in the interpulse duration and a change in the pulse width, wherein the presence of said kinetic change indicates the presence of the 5-MeC in the template nucleic acid.

2. The method of claim 1, wherein the template nucleic acid is a circular nucleic acid.

3. The method of claim 2, wherein said single-molecule sequencing reaction comprises rolling-circle synthesis of said nascent nucleic acid strand.

4. The method of claim 1, wherein the template nucleic acid is an RNA or DNA molecule.

5. The method of claim 1, wherein said single-molecule sequencing reaction comprises a polymerase.

6. The method of claim 1, wherein said monitoring said single-molecule sequencing reaction detects incorporation of said single bases of said fluorescently labeled nucleotides into the nascent nucleic acid strand and generates a sequence read.

7. The method of claim 6, wherein the kinetic change occurs at the modified base.

8. The method of claim 6, wherein the kinetic change occurs at one or more positions upstream or downstream of the modified base.

9. The method of claim 6, wherein said fluorescently labeled nucleotides are differentially labeled to be distinguishable from one another during said monitoring of said single-molecule sequencing reaction.

10. The method of claim 9, wherein each of said fluorescently labeled nucleotides comprises a fluorescent label linked to a phosphate group and the phosphate group is removed during said incorporation.

11. The method of claim 6, further comprising mapping the 5-MeC within the template nucleic acid, the mapping step comprising:

f) analyzing a portion of the sequence read to determine a sequence complementary to the template nucleic acid;

g) determining a sequence of the complement of the sequence complementary to the template nucleic acid; and h) mapping the 5-MeC at a position in the template nucleic acid.

12. The method of claim 1, wherein the template nucleic acid further comprises a glucose-modified 5-hydroxymethylcytosine (5-hmC).

13. The method of claim 12, further comprising identifying the glucose-modified 5-hmC in the template nucleic acid by detecting a further kinetic change in said single-molecule sequencing reaction.

* * * * *